(12) United States Patent
Jarjour et al.

(10) Patent No.: US 12,421,315 B2
(45) Date of Patent: Sep. 23, 2025

(54) CLL-1 TARGETED IMMUNOTHERAPIES

(71) Applicants: Regeneron Pharmaceuticals, Inc., Tarrytown, NY (US); Inhibrx Biosciences, Inc., La Jolla, CA (US)

(72) Inventors: Jordan Jarjour, Cambridge, MA (US); Mark Pogson, Cambridge, MA (US); Wai-Hang Leung, Cambridge, MA (US); Lucas Rascon, La Jolla, CA (US); Angelica Sanabria, La Jolla, CA (US); John C. Timmer, La Jolla, CA (US); Brendan P. Eckelman, La Jolla, CA (US)

(73) Assignees: Regeneron Pharmaceuticals, Inc., Tarrytown, NY (US); Inhibrx Biosciences, Inc., La Jolla, CA (US)

( * ) Notice: Subject to any disclaimer, the term of this patent is extended or adjusted under 35 U.S.C. 154(b) by 990 days.

(21) Appl. No.: 17/608,738

(22) PCT Filed: May 7, 2020

(86) PCT No.: PCT/US2020/031781
§ 371 (c)(1),
(2) Date: Nov. 3, 2021

(87) PCT Pub. No.: WO2020/227475
PCT Pub. Date: Nov. 12, 2020

(65) Prior Publication Data
US 2022/0323496 A1 Oct. 13, 2022

Related U.S. Application Data

(60) Provisional application No. 62/845,306, filed on May 8, 2019.

(51) Int. Cl.
| | |
|---|---|
| *C07K 16/28* | (2006.01) |
| *A61K 40/11* | (2025.01) |
| *A61K 40/31* | (2025.01) |
| *A61K 40/42* | (2025.01) |
| *A61P 35/00* | (2006.01) |
| *C07K 14/705* | (2006.01) |
| *C07K 14/725* | (2006.01) |
| *C07K 14/73* | (2006.01) |
| *C12N 5/0783* | (2010.01) |
| *C12N 15/62* | (2006.01) |

(52) U.S. Cl.
CPC .......... *C07K 16/2851* (2013.01); *A61K 40/11* (2025.01); *A61K 40/31* (2025.01); *A61K 40/4202* (2025.01); *A61P 35/00* (2018.01); *C07K 14/7051* (2013.01); *C07K 14/70514* (2013.01); *C07K 14/70517* (2013.01); *C07K 14/70578* (2013.01); *C12N 5/0636* (2013.01); *C12N 15/625* (2013.01); *C12N 2510/00* (2013.01); *C12N 2740/16043* (2013.01)

(58) Field of Classification Search
CPC ...... C07K 16/2851; A61K 40/31; A61P 35/00
See application file for complete search history.

(56) References Cited

U.S. PATENT DOCUMENTS

| | | |
|---|---|---|
| 5,871,753 A | 2/1999 | Crabtree et al. |
| 5,910,573 A | 6/1999 | Pluckthun et al. |
| 6,291,158 B1 | 9/2001 | Winter et al. |
| 6,291,161 B1 | 9/2001 | Lerner et al. |
| 6,423,498 B1 | 7/2002 | Markland et al. |
| 6,649,595 B2 | 11/2003 | Clackson et al. |
| 6,972,193 B1 | 12/2005 | Crabtree et al. |
| 9,587,020 B2 | 3/2017 | Wu et al. |
| 10,196,444 B2 | 2/2019 | Jarjour et al. |
| 10,287,354 B2 | 5/2019 | Brogdon et al. |
| 10,428,142 B2 | 10/2019 | Clackson et al. |
| 10,457,731 B2 | 10/2019 | Jarjour et al. |
| 11,530,265 B2 | 12/2022 | Jarjour et al. |
| 12,043,667 B2 * | 7/2024 | Rascon ............... C07K 16/2851 |
| 2007/0065431 A1 | 3/2007 | Coia et al. |
| 2011/0286980 A1 | 11/2011 | Brenner |
| 2012/0100160 A1 | 4/2012 | Lucas et al. |
| 2013/0287752 A1 | 10/2013 | Davila et al. |
| 2015/0266973 A1 | 9/2015 | Jarjour et al. |
| 2016/0017302 A1 | 1/2016 | Dotti et al. |
| 2016/0051651 A1 | 2/2016 | Brogdon et al. |
| 2016/0185862 A1 | 6/2016 | Wu et al. |

(Continued)

FOREIGN PATENT DOCUMENTS

| | | |
|---|---|---|
| CN | 109311963 A | 2/2019 |
| JP | 2002-503667 A | 2/2002 |

(Continued)

OTHER PUBLICATIONS

Morsink, L. M., Walter, R. B., & Ossenkoppele, G. J. (2019). Prognostic and therapeutic role of CLEC12A in acute myeloid leukemia. Blood reviews, 34, 26-33. (Year: 2019).*

Roy, J. P., Chua, E. J., Anderson, G. S., Uttenthal, B., & Chapman, M. A. (2024). Development and Optimisation of a CLEC12A-Targeting Inhibitory CAR to Improve the Safety Profile of SEMA4A CAR-T Cells in Multiple Myeloma. Blood, 144, 1891. (Year: 2024).*

Abate-Daga et al., CAR models: next-generation CAR modifications for enhanced T-cell function. Mol Ther Oncolytics. May 18, 2016;3:16014, 7 pages.

Alder et al., Antibody responses of variable lymphocyte receptors in the lamprey. Nat Immunol. Mar. 2008;9(3):319-27.

Banaszynski et al., Characterization of the FKBP. Rapamycin•FRB Ternary Complex. J Am Chem Soc. 2005;127(13):4715-4721.

(Continued)

Primary Examiner — Julie Wu
Assistant Examiner — Bryan William Heck
(74) Attorney, Agent, or Firm — McCarter & English, LLP; Marcie B. Clarke; Dylan M. Blumenthal

(57) ABSTRACT

The present disclosure provides improved CLL-1 targeting polypeptides and compositions for adoptive T cell therapies for treating, preventing, or ameliorating at least one symptom of a cancer, infectious disease, autoimmune disease, inflammatory disease, and immunodeficiency, or condition associated therewith.

20 Claims, 7 Drawing Sheets

Specification includes a Sequence Listing.

(56) References Cited

U.S. PATENT DOCUMENTS

| | | |
|---|---|---|
| 2016/0311901 A1 | 10/2016 | Jarjour et al. |
| 2016/0311907 A1* | 10/2016 | Brogdon ................ A61P 35/00 |
| 2016/0318996 A1 | 11/2016 | Hollands et al. |
| 2018/0230193 A1 | 8/2018 | Loew et al. |
| 2018/0237533 A1 | 8/2018 | Juillerat et al. |
| 2020/0071399 A1 | 3/2020 | Jarjour et al. |
| 2020/0347139 A1 | 11/2020 | Rascon et al. |
| 2023/0287111 A1 | 9/2023 | Jarjour et al. |
| 2024/0342215 A1 | 10/2024 | Jarjour |

FOREIGN PATENT DOCUMENTS

| | | |
|---|---|---|
| JP | 2002-508971 A | 3/2002 |
| JP | 2016-531567 A | 10/2016 |
| JP | 2017-522879 | 8/2017 |
| WO | WO-1999/036553 A2 | 7/1999 |
| WO | WO-1999/041258 A1 | 8/1999 |
| WO | WO-2006/072620 A1 | 7/2006 |
| WO | WO-2006/095164 A1 | 9/2006 |
| WO | WO-2007/098934 A1 | 9/2007 |
| WO | WO-2012/082841 A2 | 6/2012 |
| WO | WO-2014/051433 A1 | 4/2014 |
| WO | WO-2014/127261 A1 | 8/2014 |
| WO | WO-2015/017214 A1 | 2/2015 |
| WO | WO-2015/150771 A1 | 10/2015 |
| WO | 2016/014535 A1 | 1/2016 |
| WO | WO-2016/014553 A1 | 1/2016 |
| WO | WO-2017/125897 A1 | 7/2017 |
| WO | WO-2017/180993 A1 | 10/2017 |
| WO | WO-2019/118895 A1 | 6/2019 |
| WO | WO-2019/188885 A1 | 10/2019 |
| WO | WO-2020/052543 A1 | 3/2020 |
| WO | WO-2020/113063 A1 | 6/2020 |
| WO | WO-2020/123933 A1 | 6/2020 |
| WO | WO-2020/123936 A1 | 6/2020 |
| WO | WO-2020/123938 A1 | 6/2020 |
| WO | WO-2020/123947 A1 | 6/2020 |
| WO | WO-2020/227073 A1 | 11/2020 |
| WO | WO-2020/227475 A1 | 11/2020 |
| WO | WO-2020/227481 A1 | 11/2020 |
| WO | WO-2021/067347 A1 | 4/2021 |
| WO | WO-2021/207613 A1 | 10/2021 |

OTHER PUBLICATIONS

Bannas et al., Nanobodies and Nanobody-Based Human Heavy Chain Antibodies As Antitumor Therapeutics. Front Immunol. Nov. 22, 2017;8:1603, 13 pages.

Baral et al., Experimental therapy of African trypanosomiasis with a nanobody-conjugated human trypanolytic factor. Nat Med. May 2006;12(5):580-4.

Barthelemy et al., Comprehensive analysis of the factors contributing to the stability and solubility of autonomous human VH domains. J Biol Chem. Feb. 8, 2008;283(6):3639-3654.

Bayle et al., Rapamycin analogs with differential binding specificity permit orthogonal control of protein activity. Chem Biol. Jan. 2006;13(1):99-107.

Beavil et al., Alpha-helical coiled-coil stalks in the low-affinity receptor for IgE (Fc epsilon RII/CD23) and related C-type lectins. Proc Natl Acad Sci U S A. Jan. 15, 1992;89(2):753-7.

Belshaw et al., Controlling protein association and subcellular localization with a synthetic ligand that induces heterodimerization of proteins. Proc Natl Acad Sci U S A. May 14, 1996;93(10):4604-7.

Beste et al., Small antibody-like proteins with prescribed ligand specificities derived from the lipocalin fold. Proc Natl Acad Sci U S A. Mar. 2, 1999;96(5):1898-903.

Binz et al., Designing repeat proteins: well-expressed, soluble and stable proteins from combinatorial libraries of consensus ankyrin repeat proteins. J Mol Biol. Sep. 12, 2003;332(2):489-503.

Binz et al., Engineering novel binding proteins from nonimmunoglobulin domains. Nat Biotechnol. Oct. 2005;23(10):1257-68.

Brentjens et al., CD19-targeted T cells rapidly induce molecular remissions in adults with chemotherapy-refractory acute lymphoblastic leukemia. Sci Transl Med. Mar. 20, 2013;5(177):177ra38.

Brentjens et al., Safety and persistence of adoptively transferred autologous CD19-targeted T cells in patients with relapsed or chemotherapy refractory B-cell leukemias. Blood. Nov. 3, 2011;118(18):4817-28.

Brown et al., A mammalian protein targeted by G1-arresting rapamycin-receptor complex. Nature. Jun. 30, 1994;369(6483):756-8.

Capon et al. Designing CD4 immunoadhesins for AIDS therapy. Nature. Feb. 9, 1989;337(6207):525-31.

Carpenito et al., Control of large, established tumor xenografts with genetically retargeted human T cells containing CD28 and CD137 domains. Proc Natl Acad Sci U S A. Mar. 3, 2009;106(9):3360-5.

Challita et al., Multiple modifications in cis elements of the long terminal repeat of retroviral vectors lead to increased expression and decreased DNA methylation in embryonic carcinoma cells. J Virol. Feb. 1995;69(2):748-55.

Cortez-Retamozo et al., Efficient cancer therapy with a nanobody-based conjugate. Cancer Res. Apr. 15, 2004;64(8):2853-7.

Craik et al., Plant cyclotides: A unique family of cyclic and knotted proteins that defines the cyclic cystine knot structural motif. J Mol Biol. Dec. 17, 1999;294(5):1327-36.

Curran et al., Chimeric antigen receptors for T cell immunotherapy: current understanding and future directions. J Gene Med. Jun. 2012;14(6):405-15.

Dahlen et al., Bispecific antibodies in cancer immunotherapy. Ther Adv Vaccines Immunother. Feb. 2018;6(1):3-17.

Donnelly et al., The 'cleavage' activities of foot-and-mouth disease virus 2A site-directed mutants and naturally occurring '2A-like' sequences. J Gen Virol. May 2001;82(Pt 5):1027-1041.

Dotti et al., Design and development of therapies using chimeric antigen receptor-expressing T cells. Immunol Rev. Jan. 2014;257(1):107-26.

Duong et al., Enhancing the specificity of T-cell cultures for adoptive immunotherapy of cancer. Immunotherapy. Jan. 2011;3(1):33-48.

Fegan et al., Chemically controlled protein assembly: techniques and applications. Chem Rev. Jun. 9, 2010;110(6):3315-36.

Ghahroudi et al., Selection and identification of single domain antibody fragments from camel heavy-chain antibodies. FEBS Lett. Sep. 15, 1997;414(3):521-6.

Grunberg et al., Building blocks for protein interaction devices. Nucleic Acids Res. May 2010;38(8):2645-62.

Grupp et al., Chimeric antigen receptor-modified T cells for acute lymphoid leukemia. N Engl J Med. Apr. 18, 2013;368(16):1509-1518.

Hackel et al., Picomolar affinity fibronectin domains engineered utilizing loop length diversity, recursive mutagenesis, and loop shuffling. J Mol Biol. Sep. 19, 2008;381(5):1238-52.

Hamers-Casterman et al., Naturally occurring antibodies devoid of light chains. Nature. Jun. 3, 1993;363(6428):446-8.

Herrin et al., Structure and specificity of lamprey monoclonal antibodies. Proc Natl Acad Sci USA. Feb. 12, 2008;105(6):2040-5.

Hoet et al., Generation of high-affinity human antibodies by combining donor-derived and synthetic complementarity-determining-region diversity. Nat Biotechnol. Mar. 2005;23(3):344-8.

Hsu et al., Primary human T lymphocytes engineered with a codon-optimized IL-15 gene resist cytokine withdrawal-induced apoptosis and persist long-term in the absence of exogenous cytokine. J Immunol. Dec. 1, 2005;175(11):7226-34.

Hu et al., Minibody: A novel engineered anti-carcinoembryonic antigen antibody fragment (single-chain Fv-CH3) which exhibits rapid, high-level targeting of xenografts. Cancer Res. Jul. 1, 1996;56(13):3055-61.

Huang et al., Scorpion-toxin mimics of CD4 in complex with human immunodeficiency virus gp120 crystal structures, molecular mimicry, and neutralization breadth. Structure. May 2005; 13(5):755-68.

Irion et al., Identification and targeting of the ROSA26 locus in human embryonic stem cells. Nat Biotechnol. Dec. 2007;25(12):1477-82.

(56) References Cited

OTHER PUBLICATIONS

Janeway et al., Immunobiology: The Immune System in Health and Disease, 4th Edition. Current Biology Publications. pp. 148, 149 and 172, (1999).
Jespers et al., Aggregation-resistant domain antibodies selected on phage by heat denaturation. Nat Biotechnol. Sep. 2004;22(9):1161-5.
June et al., T-cell therapy at the threshold. Nat Biotechnol. Jul. 10, 2012;30(7):611-4.
Kalos et al., T cells with chimeric antigen receptors have potent antitumor effects and can establish memory in patients with advanced leukemia. Sci Transl Med. Aug. 10, 2011;3(95):95ra73.
Kay. Structure-function relationships in the FK506-binding protein (FKBP) family of peptidylprolyl cis-trans isomerases. Biochem J. Mar. 1, 1996;314 ( Pt 2)(Pt 2):361-85.
Klemm et al., Dimerization as a regulatory mechanism in signal transduction. Annu Rev Immunol. 1998;16:569-92.
Kochenderfer et al., B-cell depletion and remissions of malignancy along with cytokine-associated toxicity in a clinical trial of anti-CD19 chimeric-antigen-receptor-transduced T cells. Blood. Mar. 22, 2012;119(12):2709-20.
Kochenderfer et al., Treating B-cell cancer with T cells expressing anti-CD19 chimeric antigen receptors. Nat Rev Clin Oncol. May 2013;10(5):267-76.
Kowolik et al., D28 costimulation provided through a CD19-specific chimeric antigen receptor enhances in vivo persistence and antitumor efficacy of adoptively transferred T cells. Cancer Res. Nov. 15, 2006;66(22):10995-1004.
Lee et al., Design of a binding scaffold based on variable lymphocyte receptors of jawless vertebrates by module engineering. Proc Natl Acad Sci U S A. Feb. 28, 2012;109(9):3299-304.
Leung et al., Small Molecule-Regulated Antigen Recognition System for Inducible T Cell Targeting of CAncer Cells. Mol Ther. 2016;24:S110, Abstract No. 277.
Ma et al., Targeting CLL-1 for acute myeloid leukemia therapy. J Hematol Oncol. Apr. 24, 2019;12(1):41, 11 pages.
Main et al., Design of stable alpha-helical arrays from an idealized TPR motif. Structure. May 2003;11(5):497-508.
Manzke et al., CD3X anti-nitrophenyl bispecific diabodies: universal immunotherapeutic tools for retargeting T cells to tumors. Int J Cancer. Aug. 27, 1999;82(5):700-8.
Martin et al., Rational design of a CD4 mimic that inhibits HIV-1 entry and exposes cryptic neutralization epitopes. Nat Biotechnol. Jan. 2003;21(1):71-6.
Milone et al., Chimeric receptors containing CD137 signal transduction domains mediate enhanced survival of T cells and increased antileukemic efficacy in vivo. Mol Ther. Aug. 2009;17(8):1453-64.
Nguyen et al., Heavy-chain antibodies in Camelidae; a case of evolutionary innovation. Immunogenetics. Apr. 2002;54(1):39-47.
Nguyen et al., The specific variable domain of camel heavy-chain antibodies is encoded in the germline. J Mol Biol. Jan. 23, 1998;275(3):413-8.
Nord et al., A combinatorial library of an alpha-helical bacterial receptor domain. Protein Eng. Jun. 1995;8(6):601-8.
Nord et al., Binding proteins selected from combinatorial libraries of an alpha-helical bacterial receptor domain. Nat Biotechnol. Aug. 1997;15(8):772-7.
Nord et al., Recombinant human factor VIII-specific affinity ligands selected from phage-displayed combinatorial libraries of protein A. Eur J Biochem. Aug. 2001;268(15):4269-77.
Parker et al., Antibody mimics based on human fibronectin type three domain engineered for thermostability and high-affinity binding to vascular endothelial growth factor receptor two. Protein Eng Des Sel. Sep. 2005;18(9):435-44.
Pule et al., A chimeric T cell antigen receptor that augments cytokine release and supports clonal expansion of primary human T cells. Mol Ther. Nov. 2005;12(5):933-41.
Quintarelli et al., Co-expression of cytokine and suicide genes to enhance the activity and safety of tumor-specific cytotoxic T lymphocytes. Blood. Oct. 15, 2007;110(8):2793-802.
Restifo et al., Adoptive immunotherapy for cancer: harnessing the T cell response. Nat Rev Immunol. Mar. 22, 2012;12(4):269-81.
Richards et al., Engineered fibronectin type III domain with a RGDWXE sequence binds with enhanced affinity and specificity to human alphavbeta3 integrin. J Mol Biol. Mar. 7, 2003;326(5):1475-88.
Roux et al., Structural analysis of the nurse shark (new) antigen receptor (NAR): molecular convergence of NAR and unusual mammalian immunoglobulins. Proc Natl Acad Sci U S A Sep. 29, 1998;95(20):11804-9.
Ryan et al., Virus-encoded proteinases of the picornavirus supergroup. J Gen Virol. Apr. 1997;78 ( Pt 4):699-723.
Sato et al., Genes encoding putative natural killer cell C-type lectin receptors in teleostean fishes. Proc Natl Acad Sci U S A. Jun. 24, 2003;100(13):7779-84.
Schlessinger. Cell signaling by receptor tyrosine kinases. Cell. Oct. 13, 2000;103(2):211-25.
Schonfeld et al., An engineered lipocalin specific for CTLA-4 reveals a combining site with structural and conformational features similar to antibodies. Proc Natl Acad Sci U S A. May 19, 2009;106(20):8198-203.
Skerra, Alternative binding proteins: anticalins—harnessing the structural plasticity of the lipocalin ligand pocket to engineer novel binding activities. Febs J. Jun. 2008;275(11):2677- 83.
Spencer et al., Controlling signal transduction with synthetic ligands. Science. Nov. 12, 1993;262(5136):1019-24.
Standaert et al., Molecular cloning and overexpression of the human FK506-binding protein FKBP. Nature. Aug. 16, 1990;346(6285):671-4.
Stephan et al., T cell-encoded CD80 and 4-1BBL induce auto- and transcostimulation, resulting in potent tumor rejection. Nat Med. Dec. 2007;13(12):1440-9.
Stumpp et al., Designing repeat proteins: modular leucine-rich repeat protein libraries based on the mammalian ribonuclease inhibitor family. J Mol Biol. Sep. 12, 2003;332(2):471-87.
Tal et al., An NCR1-based chimeric receptor endows T-cells with multiple anti-tumor specificities. Oncotarget. Nov. 15, 2014;5(21):10949-58.
Till et al., CD20-specific adoptive immunotherapy for lymphoma using a chimeric antigen receptor with both CD28 and 4-1BB domains: pilot clinical trial results. Blood. Apr. 26, 2012;119(17):3940-50.
Varadamsetty et al., Designed Armadillo repeat proteins: library generation, characterization and selection of peptide binders with high specificity. J Mol Biol. Nov. 23, 2012;424(1-2):68-87.
Vincke et al., General strategy to humanize a camelid single-domain antibody and identification of a universal humanized nanobody scaffold. J Biol Chem. Jan. 30, 2009;284(5):3273-3284.
Vita et al., Scorpion toxins as natural scaffolds for protein engineering. Proc Natl Acad Sci U S A. Jul. 3, 1995;92(14):6404-8.
Weisel et al., A model for fibrinogen: domains and sequence. Science. Dec. 20, 1985;230(4732):1388-91.
White et al., Comparison of the glycosyl-phosphatidylinositol cleavage/attachment site between mammalian cells and parasitic protozoa. J Cell Sci. Feb. 2000;113 ( Pt 4):721-7.
Wilkie et al., Dual targeting of ErbB2 and MUC1 in breast cancer using chimeric antigen receptors engineered to provide complementary signaling. J Clin Immunol. Oct. 2012;32(5):1059-70.
Zelensky et al., The C-type lectin-like domain superfamily. FEBS J. Dec. 2005;272(24):6179-217.
Atilla et al., Optimizing C-Type Lectin-like Molecule 1 (CLL-1) Directed CAR T Cell Therapy of Acute Myeloid Leukemia Pinar Ataca Atilla. Biol Blood Marrow Transplant. 2019;25:S167-S168, Abstract 230.
Tashiro et al., Treatment of Acute Myeloid Leukemia with T Cells Expressing Chimeric Antigen Receptors Directed to C-type Lectin-like Molecule 1. Mol Ther. Sep. 6, 2017;25(9):2202-2213.
U.S. Appl. No. 14/908,734, now U.S. Pat. No. 10,196,444, filed Jan. 29, 2016, Issued.
U.S. Appl. No. 14/608,098, now U.S. Pat. No. 10,428,142, filed Jan. 28, 2015, Issued.
U.S. Appl. No. 16/219,640, now U.S. Pat. No. 10,457,371, filed Dec. 13, 2018, Issued.

(56) References Cited

OTHER PUBLICATIONS

U.S. Appl. No. 16/540,673, 2020-0071399, filed Aug. 14, 2019, Abandoned.
U.S. Appl. No. 16/573,254, now U.S. Pat. No. 11,530,265, filed Sep. 17, 2019, Issued.
U.S. Appl. No. 17/675,246, filed Feb. 18, 2022, Abandoned.
U.S. Appl. No. 18/054,223, 2023-0287111, filed Nov. 10, 2022, Published.
U.S. Appl. No. 17/312,120, 2022-0031750, filed Jun. 9, 2021, Published.
U.S. Appl. No. 17/312,116, 2022-0025014, filed Jun. 9, 2021, Published.
U.S. Appl. No. 17/764,365, 2023-0031838, filed Mar. 28, 2022, Published.
U.S. Appl. No. 18/578,367, filed Jan. 11, 2024, Pending.

\* cited by examiner

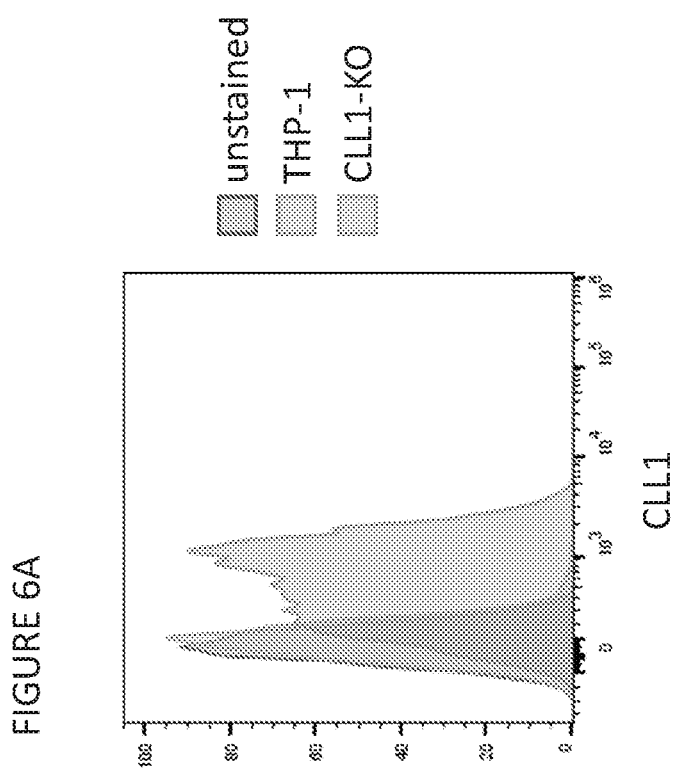

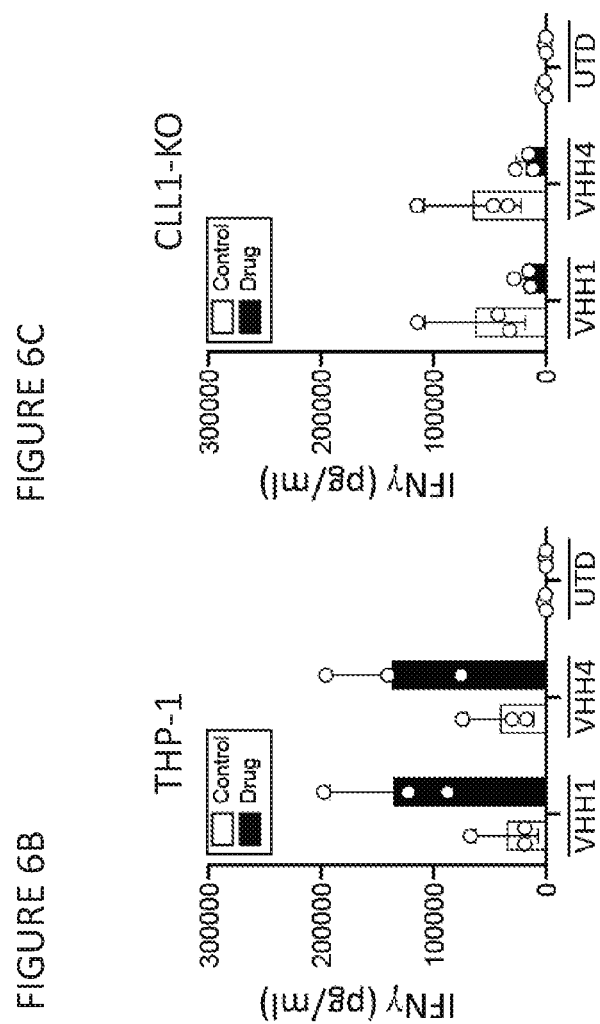

SEQUENCE LISTING

<160> NUMBER OF SEQ ID NOS: 87

<210> SEQ ID NO 1
<211> LENGTH: 265
<212> TYPE: PRT
<213> ORGANISM: Homo sapiens

<400> SEQUENCE: 1

```
Met Ser Glu Glu Val Thr Tyr Ala Asp Leu Gln Phe Gln Asn Ser Ser
1               5                   10                  15

Glu Met Glu Lys Ile Pro Glu Ile Gly Lys Phe Gly Glu Lys Ala Pro
            20                  25                  30

Pro Ala Pro Ser His Val Trp Arg Pro Ala Ala Leu Phe Leu Thr Leu
        35                  40                  45

Leu Cys Leu Leu Leu Leu Ile Gly Leu Gly Val Leu Ala Ser Met Phe
    50                  55                  60

His Val Thr Leu Lys Ile Glu Met Lys Lys Met Asn Lys Leu Gln Asn
65                  70                  75                  80

Ile Ser Glu Glu Leu Gln Arg Asn Ile Ser Leu Gln Leu Met Ser Asn
                85                  90                  95

Met Asn Ile Ser Asn Lys Ile Arg Asn Leu Ser Thr Thr Leu Gln Thr
            100                 105                 110

Ile Ala Thr Lys Leu Cys Arg Glu Leu Tyr Ser Lys Glu Gln Glu His
        115                 120                 125

Lys Cys Lys Pro Cys Pro Arg Arg Trp Ile Trp His Lys Asp Ser Cys
    130                 135                 140

Tyr Phe Leu Ser Asp Asp Val Gln Thr Trp Gln Glu Ser Lys Met Ala
145                 150                 155                 160

Cys Ala Ala Gln Asn Ala Ser Leu Leu Lys Ile Asn Asn Lys Asn Ala
                165                 170                 175

Leu Glu Phe Ile Lys Ser Gln Ser Arg Ser Tyr Asp Tyr Trp Leu Gly
            180                 185                 190

Leu Ser Pro Glu Glu Asp Ser Thr Arg Gly Met Arg Val Asp Asn Ile
        195                 200                 205

Ile Asn Ser Ser Ala Trp Val Ile Arg Asn Ala Pro Asp Leu Asn Asn
    210                 215                 220

Met Tyr Cys Gly Tyr Ile Asn Arg Leu Tyr Val Gln Tyr Tyr His Cys
225                 230                 235                 240

Thr Tyr Lys Lys Arg Met Ile Cys Glu Lys Met Ala Asn Pro Val Gln
                245                 250                 255

Leu Gly Ser Thr Tyr Phe Arg Glu Ala
            260                 265
```

<210> SEQ ID NO 2
<211> LENGTH: 120
<212> TYPE: PRT
<213> ORGANISM: Artificial Sequence
<220> FEATURE:
<223> OTHER INFORMATION: Made in Lab - anti-CLL-1 VHH domain

<400> SEQUENCE: 2

```
Glu Val Gln Leu Val Glu Ser Gly Gly Gly Val Gln Pro Gly Gly
 1               5                  10                  15

Ser Leu Arg Leu Ser Cys Ala Ala Ser Gly Phe Leu Phe Ser Ile Tyr
            20                  25                  30

Asp Met Asn Trp Tyr Arg Gln Ala Pro Gly Lys Glu Arg Glu Trp Val
        35                  40                  45

Ala Gly Ile Thr Asn Asn Gly Tyr Ser Thr Ala Tyr Ala Glu Ser Val
    50                  55                  60

Lys Gly Arg Phe Thr Ile Ser Arg Asp Asn Ala Lys Asn Thr Ile Tyr
65                  70                  75                  80

Leu Gln Met Ser Ser Leu Arg Ala Glu Asp Thr Ala Val Tyr Tyr Cys
                85                  90                  95

His Ala Asp Leu Thr Lys Ala Tyr Asp Val Glu Tyr Ala Trp Gly Gln
            100                 105                 110

Gly Thr Leu Val Thr Val Lys Pro
        115                 120
```

<210> SEQ ID NO 3
<211> LENGTH: 121
<212> TYPE: PRT
<213> ORGANISM: Artificial Sequence
<220> FEATURE:
<223> OTHER INFORMATION: Made in Lab - anti-CLL-1 VHH domain

<400> SEQUENCE: 3

```
Glu Val Gln Leu Val Glu Ser Gly Gly Gly Val Gln Pro Gly Gly
 1               5                  10                  15

Ser Leu Arg Leu Ser Cys Ala Ala Ser Gly Phe Thr Phe Ser Val Tyr
            20                  25                  30

Asp Met Asn Trp Tyr Arg Gln Ala Pro Gly Lys Glu Arg Glu Trp Val
        35                  40                  45

Ser Gly Ile Ser Asn Asn Gly Phe Ser Thr Ala Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Asn Leu Asp Val His Gly Arg Val Gly Ala Gln Gly Asp Tyr Trp Gly
            100                 105                 110

Gln Gly Thr Leu Val Thr Val Lys Pro
        115                 120
```

<210> SEQ ID NO 4
<211> LENGTH: 129
<212> TYPE: PRT
<213> ORGANISM: Artificial Sequence
<220> FEATURE:
<223> OTHER INFORMATION: Made in Lab - anti-CLL-1 VHH domain

<400> SEQUENCE: 4

Glu Val Gln Leu Val Glu Ser Gly Gly Gly Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Glu Gly Val
        35                  40                  45

Ser Thr Ile Ser Ser Asp Gly Ser Thr Tyr Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Ala Leu Arg Glu Gly Leu Pro Leu Leu Leu Asp Thr Leu Trp Arg Gln
            100                 105                 110

Pro Val Glu Tyr Asp Tyr Trp Gly Gln Gly Thr Gln Val Thr Val Lys
            115                 120                 125

Pro

<210> SEQ ID NO 5
<211> LENGTH: 116
<212> TYPE: PRT
<213> ORGANISM: Artificial Sequence
<220> FEATURE:
<223> OTHER INFORMATION: Made in Lab - anti-CLL-1 VHH domain

<400> SEQUENCE: 5

Glu Val Gln Leu Val Glu Ser Gly Gly Gly Glu Val Gln Pro Gly Gly
1               5                   10                  15

Ser Leu Arg Leu Ser Cys Ala Ala Ser Gly Leu Leu Phe Ser Ile Tyr
            20                  25                  30

Asp Met Asn Trp Tyr Arg Gln Ala Pro Gly Lys Glu Arg Glu Trp Val
        35                  40                  45

Ala Gly Ile Thr Asn Asn Gly Tyr Ser Thr Ala Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

His Thr Asp Glu Trp Gly Arg Glu Tyr Trp Gly Gln Gly Thr Leu Val
            100                 105                 110

Thr Val Lys Pro
        115

<210> SEQ ID NO 6
<211> LENGTH: 112
<212> TYPE: PRT
<213> ORGANISM: Artificial Sequence
<220> FEATURE:
<223> OTHER INFORMATION: Made in Lab - anti-CLL-1 VHH domain

<400> SEQUENCE: 6

Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Thr Phe Glu Tyr Asp
            20                  25                  30

Asp Met Val Trp Phe Arg Gln Ala Pro Gly Lys Glu Arg Glu Glu Val
        35                  40                  45

```
Ala Gly Ile Ser Trp Ser Gly Gly Ser Ile Tyr Tyr Ala Glu Ser Val
 50                  55                  60

Lys Gly Arg Phe Ser Ile Ser Arg Asp Asn Ala Lys Asn Thr Val Tyr
 65                  70                  75                  80

Leu Glu Met Asn Arg Leu Lys Pro Glu Asp Thr Ala Val Tyr Tyr Cys
                 85                  90                  95

Asn Val Gly Ser Tyr Trp Gly Gln Gly Thr Leu Val Thr Val Lys Pro
            100                 105                 110
```

<210> SEQ ID NO 7
<211> LENGTH: 119
<212> TYPE: PRT
<213> ORGANISM: Artificial Sequence
<220> FEATURE:
<223> OTHER INFORMATION: Made in Lab - anti-CLL-1 VHH domain

<400> SEQUENCE: 7

```
Glu Val Gln Leu Val Glu Ser Gly Gly Gly Glu Val Gln Pro Gly Gly
 1               5                   10                  15

Ser Leu Arg Leu Ser Cys Ala Ala Ser Gly Phe Thr Phe Arg Ile Asn
                 20                  25                  30

Asp Met Gly Trp Tyr Arg Gln Ala Pro Gly Lys Glu Cys Glu Met Val
             35                  40                  45

Ala Gly Ile Ser Asn Asn Gly Phe Ser Thr Ala Tyr Ala Glu Ser Val
 50                  55                  60

Lys Gly Arg Phe Thr Ile Ser Arg Asp Asn Ala Lys Asn Thr Val Tyr
 65                  70                  75                  80

Leu Gln Met Ser Ser Leu Arg Ala Glu Asp Thr Ala Val Tyr Tyr Cys
                 85                  90                  95

His Arg Thr Asp Glu Gly Ala Ala His Ala Cys Ser Arg Gly Gln Gly
            100                 105                 110

Thr Leu Val Thr Val Lys Pro
        115
```

<210> SEQ ID NO 8
<211> LENGTH: 120
<212> TYPE: PRT
<213> ORGANISM: Artificial Sequence
<220> FEATURE:
<223> OTHER INFORMATION: Made in Lab - anti-CLL-1 VHH domain
<220> FEATURE:
<221> NAME/KEY: MOD_RES
<222> LOCATION: (119)..(120)
<223> OTHER INFORMATION: Xaa is any amino acid or absent

<400> SEQUENCE: 8

```
Glu Val Gln Leu Val Glu Ser Gly Gly Gly Glu Val Gln Pro Gly Gly
 1               5                   10                  15

Ser Leu Arg Leu Ser Cys Ala Ala Ser Gly Phe Leu Phe Ser Ile Tyr
                 20                  25                  30

Asp Met Asn Trp Tyr Arg Gln Ala Pro Gly Lys Glu Arg Glu Trp Val
             35                  40                  45

Ala Gly Ile Thr Asn Asn Gly Tyr Ser Thr Ala Tyr Ala Glu Ser Val
 50                  55                  60

Lys Gly Arg Phe Thr Ile Ser Arg Asp Asn Ala Lys Asn Thr Ile Tyr
 65                  70                  75                  80

Leu Gln Met Ser Ser Leu Arg Ala Glu Asp Thr Ala Val Tyr Tyr Cys
                 85                  90                  95

His Ala Asp Leu Thr Lys Ala Tyr Asp Val Glu Tyr Ala Trp Gly Gln
```

```
                100             105             110
Gly Thr Leu Val Thr Val Xaa Xaa
            115             120

<210> SEQ ID NO 9
<211> LENGTH: 121
<212> TYPE: PRT
<213> ORGANISM: Artificial Sequence
<220> FEATURE:
<223> OTHER INFORMATION: Made in Lab - anti-CLL-1 VHH domain
<220> FEATURE:
<221> NAME/KEY: MOD_RES
<222> LOCATION: (120)..(121)
<223> OTHER INFORMATION: Xaa is any amino acid or absent

<400> SEQUENCE: 9

Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Val Tyr
            20                  25                  30

Asp Met Asn Trp Tyr Arg Gln Ala Pro Gly Lys Glu Arg Glu Trp Val
        35                  40                  45

Ser Gly Ile Ser Asn Asn Gly Phe Ser Thr Ala Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Asn Leu Asp Val His Gly Arg Val Gly Ala Gln Gly Asp Tyr Trp Gly
            100                 105                 110

Gln Gly Thr Leu Val Thr Val Xaa Xaa
            115             120

<210> SEQ ID NO 10
<211> LENGTH: 129
<212> TYPE: PRT
<213> ORGANISM: Artificial Sequence
<220> FEATURE:
<223> OTHER INFORMATION: Made in Lab - anti-CLL-1 VHH domain
<220> FEATURE:
<221> NAME/KEY: MOD_RES
<222> LOCATION: (128)..(129)
<223> OTHER INFORMATION: Xaa is any amino acid or absent

<400> SEQUENCE: 10

Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Glu Gly Val
        35                  40                  45

Ser Thr Ile Ser Ser Ser Asp Gly Ser Thr Tyr Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Ala Leu Arg Glu Gly Leu Pro Leu Leu Leu Asp Thr Leu Trp Arg Gln
            100                 105                 110

Pro Val Glu Tyr Asp Tyr Trp Gly Gln Gly Thr Gln Val Thr Val Xaa
```

```
            115                 120                 125
Xaa

<210> SEQ ID NO 11
<211> LENGTH: 116
<212> TYPE: PRT
<213> ORGANISM: Artificial Sequence
<220> FEATURE:
<223> OTHER INFORMATION: Made in Lab - anti-CLL-1 VHH domain
<220> FEATURE:
<221> NAME/KEY: MOD_RES
<222> LOCATION: (115)..(116)
<223> OTHER INFORMATION: Xaa is any amino acid or absent

<400> SEQUENCE: 11
```

Glu Val Gln Leu Val Glu Ser Gly Gly Gly Glu Val Gln Pro Gly Gly
1               5                   10                  15

Ser Leu Arg Leu Ser Cys Ala Ala Ser Gly Leu Leu Phe Ser Ile Tyr
            20                  25                  30

Asp Met Asn Trp Tyr Arg Gln Ala Pro Gly Lys Glu Arg Glu Trp Val
        35                  40                  45

Ala Gly Ile Thr Asn Asn Gly Tyr Ser Thr Ala Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

His Thr Asp Glu Trp Gly Arg Gly Tyr Trp Gly Gln Gly Thr Leu Val
            100                 105                 110

Thr Val Xaa Xaa
        115

```
<210> SEQ ID NO 12
<211> LENGTH: 112
<212> TYPE: PRT
<213> ORGANISM: Artificial Sequence
<220> FEATURE:
<223> OTHER INFORMATION: Made in Lab - anti-CLL-1 VHH domain
<220> FEATURE:
<221> NAME/KEY: MOD_RES
<222> LOCATION: (111)..(112)
<223> OTHER INFORMATION: Xaa is any amino acid or absent

<400> SEQUENCE: 12
```

Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Thr Phe Glu Tyr Asp
            20                  25                  30

Asp Met Val Trp Phe Arg Gln Ala Pro Gly Lys Glu Arg Glu Val
        35                  40                  45

Ala Gly Ile Ser Trp Ser Gly Gly Ser Ile Tyr Tyr Ala Glu Ser Val
    50                  55                  60

Lys Gly Arg Phe Ser Ile Ser Arg Asp Asn Ala Lys Asn Thr Val Tyr
65                  70                  75                  80

Leu Glu Met Asn Arg Leu Lys Pro Glu Asp Thr Ala Val Tyr Tyr Cys
                85                  90                  95

Asn Val Gly Ser Tyr Trp Gly Gln Gly Thr Leu Val Thr Val Xaa Xaa
            100                 105                 110

```
<210> SEQ ID NO 13
```

```
<211> LENGTH: 119
<212> TYPE: PRT
<213> ORGANISM: Artificial Sequence
<220> FEATURE:
<223> OTHER INFORMATION: Made in Lab - anti-CLL-1 VHH domain
<220> FEATURE:
<221> NAME/KEY: MOD_RES
<222> LOCATION: (118)..(119)
<223> OTHER INFORMATION: Xaa is any amino acid or absent

<400> SEQUENCE: 13

Glu Val Gln Leu Val Glu Ser Gly Gly Gly Val Gln Pro Gly Gly
1               5                   10                  15

Ser Leu Arg Leu Ser Cys Ala Ala Ser Gly Phe Thr Phe Arg Ile Asn
            20                  25                  30

Asp Met Gly Trp Tyr Arg Gln Ala Pro Gly Lys Glu Cys Glu Met Val
        35                  40                  45

Ala Gly Ile Ser Asn Asn Gly Phe Ser Thr Ala Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

His Arg Thr Asp Glu Gly Ala Ala His Ala Cys Ser Arg Gly Gln Gly
            100                 105                 110

Thr Leu Val Thr Val Xaa Xaa
            115

<210> SEQ ID NO 14
<211> LENGTH: 287
<212> TYPE: PRT
<213> ORGANISM: Artificial Sequence
<220> FEATURE:
<223> OTHER INFORMATION: Made in Lab - anti-CLL-1 VHH DARIC binding
    component

<400> SEQUENCE: 14

Met Glu Thr Asp Thr Leu Leu Leu Trp Val Leu Leu Leu Trp Val Pro
1               5                   10                  15

Gly Ser Thr Gly Glu Val Gln Leu Val Glu Ser Gly Gly Gly Glu Val
            20                  25                  30

Gln Pro Gly Gly Ser Leu Arg Leu Ser Cys Ala Ala Ser Gly Phe Leu
        35                  40                  45

Phe Ser Ile Tyr Asp Met Asn Trp Tyr Arg Gln Ala Pro Gly Lys Glu
    50                  55                  60

Arg Glu Trp Val Ala Gly Ile Thr Asn Asn Gly Tyr Ser Thr Ala Tyr
65                  70                  75                  80

Ala Glu Ser Val Lys Gly Arg Phe Thr Ile Ser Arg Asp Asn Ala Lys
                85                  90                  95

Asn Thr Ile Tyr Leu Gln Met Ser Ser Leu Arg Ala Glu Asp Thr Ala
            100                 105                 110

Val Tyr Tyr Cys His Ala Asp Leu Thr Lys Ala Tyr Asp Val Glu Tyr
        115                 120                 125

Ala Trp Gly Gln Gly Thr Leu Val Thr Val Lys Pro Gly Gly Gly Gly
    130                 135                 140

Ser Gly Val Gln Val Glu Thr Ile Ser Pro Gly Asp Gly Arg Thr Phe
145                 150                 155                 160

Pro Lys Arg Gly Gln Thr Cys Val Val His Tyr Thr Gly Met Leu Glu
                165                 170                 175
```

```
Asp Gly Lys Lys Phe Asp Ser Ser Arg Asp Arg Asn Lys Pro Phe Lys
            180                 185                 190

Phe Met Leu Gly Lys Gln Glu Val Ile Arg Gly Trp Glu Glu Gly Val
        195                 200                 205

Ala Gln Met Ser Val Gly Gln Arg Ala Lys Leu Thr Ile Ser Pro Asp
    210                 215                 220

Tyr Ala Tyr Gly Ala Thr Gly His Pro Gly Ile Ile Pro Pro His Ala
225                 230                 235                 240

Thr Leu Val Phe Asp Val Glu Leu Leu Lys Leu Glu Gly Gly Arg Met
                245                 250                 255

Ala Leu Ile Val Leu Gly Val Ala Gly Leu Leu Phe Ile Gly
            260                 265                 270

Leu Gly Ile Phe Phe Cys Val Arg Cys Arg His Arg Arg Gln
            275                 280                 285
```

<210> SEQ ID NO 15
<211> LENGTH: 288
<212> TYPE: PRT
<213> ORGANISM: Artificial Sequence
<220> FEATURE:
<223> OTHER INFORMATION: Made in Lab - anti-CLL-1 VHH DARIC binding
      component

<400> SEQUENCE: 15

```
Met Glu Thr Asp Thr Leu Leu Leu Trp Val Leu Leu Leu Trp Val Pro
1               5                   10                  15

Gly Ser Thr Gly Glu Val Gln Leu Val Glu Ser Gly Gly Gly Glu Val
            20                  25                  30

Gln Pro Gly Gly Ser Leu Arg Leu Ser Cys Ala Ala Ser Gly Phe Thr
        35                  40                  45

Phe Ser Val Tyr Asp Met Asn Trp Tyr Arg Gln Ala Pro Gly Lys Glu
    50                  55                  60

Arg Glu Trp Val Ser Gly Ile Ser Asn Asn Gly Phe Ser Thr Ala Tyr
65                  70                  75                  80

Ala Glu Ser Val Lys Gly Arg Phe Thr Ile Ser Arg Asp Asn Ala Lys
                85                  90                  95

Asn Thr Leu Tyr Leu Gln Met Ser Ser Leu Arg Ala Glu Asp Thr Ala
            100                 105                 110

Val Tyr Tyr Cys Asn Leu Asp Val His Gly Arg Val Gly Ala Gln Gly
        115                 120                 125

Asp Tyr Trp Gly Gln Gly Thr Leu Val Thr Val Lys Pro Gly Gly Gly
    130                 135                 140

Gly Ser Gly Val Gln Val Glu Thr Ile Ser Pro Gly Asp Gly Arg Thr
145                 150                 155                 160

Phe Pro Lys Arg Gly Gln Thr Cys Val Val His Tyr Thr Gly Met Leu
                165                 170                 175

Glu Asp Gly Lys Lys Phe Asp Ser Ser Arg Asp Arg Asn Lys Pro Phe
            180                 185                 190

Lys Phe Met Leu Gly Lys Gln Glu Val Ile Arg Gly Trp Glu Glu Gly
        195                 200                 205

Val Ala Gln Met Ser Val Gly Gln Arg Ala Lys Leu Thr Ile Ser Pro
    210                 215                 220

Asp Tyr Ala Tyr Gly Ala Thr Gly His Pro Gly Ile Ile Pro Pro His
225                 230                 235                 240

Ala Thr Leu Val Phe Asp Val Glu Leu Leu Lys Leu Glu Gly Gly Arg
```

```
                    245                 250                 255
Met Ala Leu Ile Val Leu Gly Gly Val Ala Gly Leu Leu Phe Ile
                260                 265                 270
Gly Leu Gly Ile Phe Phe Cys Val Arg Cys Arg His Arg Arg Gln
            275                 280                 285
```

<210> SEQ ID NO 16
<211> LENGTH: 296
<212> TYPE: PRT
<213> ORGANISM: Artificial Sequence
<220> FEATURE:
<223> OTHER INFORMATION: Made in Lab - anti-CLL-1 VHH DARIC binding
      component

<400> SEQUENCE: 16

```
Met Glu Thr Asp Thr Leu Leu Leu Trp Val Leu Leu Leu Trp Val Pro
1               5                   10                  15
Gly Ser Thr Gly Glu Val Gln Leu Val Glu Ser Gly Gly Gly Glu Val
                20                  25                  30
Gln Pro Gly Gly Ser Leu Arg Leu Ser Cys Ala Ala Ser Gly Phe Thr
            35                  40                  45
Phe Asp Asp Tyr Ala Ile Gly Trp Phe Arg Gln Ala Pro Gly Lys Glu
        50                  55                  60
Arg Glu Gly Val Ser Thr Ile Ser Ser Asp Gly Ser Thr Tyr Tyr
65                  70                  75                  80
Ala Glu Ser Val Lys Gly Arg Phe Thr Ile Ser Arg Asp Asn Ala Lys
                85                  90                  95
Asn Thr Val Tyr Leu Gln Met Ser Ser Leu Arg Ala Glu Asp Thr Ala
            100                 105                 110
Val Tyr Tyr Cys Ala Leu Arg Glu Gly Leu Pro Leu Leu Leu Asp Thr
        115                 120                 125
Leu Trp Arg Gln Pro Val Glu Tyr Asp Tyr Trp Gly Gln Gly Thr Gln
130                 135                 140
Val Thr Val Lys Pro Gly Gly Gly Ser Gly Val Gln Val Glu Thr
145                 150                 155                 160
Ile Ser Pro Gly Asp Gly Arg Thr Phe Pro Lys Arg Gly Gln Thr Cys
                165                 170                 175
Val Val His Tyr Thr Gly Met Leu Glu Asp Gly Lys Lys Phe Asp Ser
            180                 185                 190
Ser Arg Asp Arg Asn Lys Pro Phe Lys Phe Met Leu Gly Lys Gln Glu
        195                 200                 205
Val Ile Arg Gly Trp Glu Glu Gly Val Ala Gln Met Ser Val Gly Gln
        210                 215                 220
Arg Ala Lys Leu Thr Ile Ser Pro Asp Tyr Ala Tyr Gly Ala Thr Gly
225                 230                 235                 240
His Pro Gly Ile Ile Pro Pro His Ala Thr Leu Val Phe Asp Val Glu
                245                 250                 255
Leu Leu Lys Leu Glu Gly Gly Arg Met Ala Leu Ile Val Leu Gly Gly
            260                 265                 270
Val Ala Gly Leu Leu Leu Phe Ile Gly Leu Gly Ile Phe Phe Cys Val
        275                 280                 285
Arg Cys Arg His Arg Arg Gln
290                 295
```

<210> SEQ ID NO 17
<211> LENGTH: 283

```
<212> TYPE: PRT
<213> ORGANISM: Artificial Sequence
<220> FEATURE:
<223> OTHER INFORMATION: Made in Lab - anti-CLL-1 VHH DARIC binding
      component

<400> SEQUENCE: 17

Met Glu Thr Asp Thr Leu Leu Leu Trp Val Leu Leu Leu Trp Val Pro
1               5                   10                  15

Gly Ser Thr Gly Glu Val Gln Leu Val Glu Ser Gly Gly Gly Glu Val
            20                  25                  30

Gln Pro Gly Gly Ser Leu Arg Leu Ser Cys Ala Ala Ser Gly Leu Leu
        35                  40                  45

Phe Ser Ile Tyr Asp Met Asn Trp Tyr Arg Gln Ala Pro Gly Lys Glu
    50                  55                  60

Arg Glu Trp Val Ala Gly Ile Thr Asn Asn Gly Tyr Ser Thr Ala Tyr
65                  70                  75                  80

Ala Glu Ser Val Lys Gly Arg Phe Thr Ile Ser Arg Asp Asn Ala Lys
                85                  90                  95

Asn Thr Val Tyr Leu Gln Met Ser Ser Leu Arg Ala Glu Asp Thr Ala
            100                 105                 110

Val Tyr Tyr Cys His Thr Asp Glu Trp Gly Arg Glu Tyr Trp Gly Gln
        115                 120                 125

Gly Thr Leu Val Thr Val Lys Pro Gly Gly Gly Ser Gly Val Gln
    130                 135                 140

Val Glu Thr Ile Ser Pro Gly Asp Gly Arg Thr Phe Pro Lys Arg Gly
145                 150                 155                 160

Gln Thr Cys Val Val His Tyr Thr Gly Met Leu Glu Asp Gly Lys Lys
                165                 170                 175

Phe Asp Ser Ser Arg Asp Arg Asn Lys Pro Phe Lys Phe Met Leu Gly
            180                 185                 190

Lys Gln Glu Val Ile Arg Gly Trp Glu Glu Gly Val Ala Gln Met Ser
        195                 200                 205

Val Gly Gln Arg Ala Lys Leu Thr Ile Ser Pro Asp Tyr Ala Tyr Gly
    210                 215                 220

Ala Thr Gly His Pro Gly Ile Ile Pro Pro His Ala Thr Leu Val Phe
225                 230                 235                 240

Asp Val Glu Leu Leu Lys Leu Glu Gly Arg Met Ala Leu Ile Val
                245                 250                 255

Leu Gly Gly Val Ala Gly Leu Leu Phe Ile Gly Leu Gly Ile Phe
            260                 265                 270

Phe Cys Val Arg Cys Arg His Arg Arg Gln
        275                 280

<210> SEQ ID NO 18
<211> LENGTH: 279
<212> TYPE: PRT
<213> ORGANISM: Artificial Sequence
<220> FEATURE:
<223> OTHER INFORMATION: Made in Lab - anti-CLL-1 VHH DARIC binding
      component

<400> SEQUENCE: 18

Met Glu Thr Asp Thr Leu Leu Leu Trp Val Leu Leu Leu Trp Val Pro
1               5                   10                  15

Gly Ser Thr Gly Glu Val Gln Leu Val Glu Ser Gly Gly Gly Glu Val
            20                  25                  30
```

-continued

Gln Pro Gly Gly Ser Leu Arg Leu Ser Cys Ala Ala Ser Gly Arg Thr
            35                  40                  45

Phe Glu Tyr Asp Asp Met Val Trp Phe Arg Gln Ala Pro Gly Lys Glu
 50                  55                  60

Arg Glu Glu Val Ala Gly Ile Ser Trp Ser Gly Ser Ile Tyr Tyr
 65                  70                  75                  80

Ala Glu Ser Val Lys Gly Arg Phe Ser Ile Ser Arg Asp Asn Ala Lys
                85                  90                  95

Asn Thr Val Tyr Leu Glu Met Asn Arg Leu Lys Pro Glu Asp Thr Ala
                100                 105                 110

Val Tyr Tyr Cys Asn Val Gly Ser Tyr Trp Gly Gln Gly Thr Leu Val
                115                 120                 125

Thr Val Lys Pro Gly Gly Gly Ser Gly Val Gln Val Glu Thr Ile
 130                 135                 140

Ser Pro Gly Asp Gly Arg Thr Phe Pro Lys Arg Gly Gln Thr Cys Val
 145                 150                 155                 160

Val His Tyr Thr Gly Met Leu Glu Asp Gly Lys Lys Phe Asp Ser Ser
                165                 170                 175

Arg Asp Arg Asn Lys Pro Phe Lys Phe Met Leu Gly Lys Gln Glu Val
                180                 185                 190

Ile Arg Gly Trp Glu Glu Gly Val Ala Gln Met Ser Val Gly Gln Arg
            195                 200                 205

Ala Lys Leu Thr Ile Ser Pro Asp Tyr Ala Tyr Gly Ala Thr Gly His
            210                 215                 220

Pro Gly Ile Ile Pro Pro His Ala Thr Leu Val Phe Asp Val Glu Leu
225                 230                 235                 240

Leu Lys Leu Glu Gly Gly Arg Met Ala Leu Ile Val Leu Gly Gly Val
                245                 250                 255

Ala Gly Leu Leu Leu Phe Ile Gly Leu Gly Ile Phe Phe Cys Val Arg
                260                 265                 270

Cys Arg His Arg Arg Arg Gln
                275

<210> SEQ ID NO 19
<211> LENGTH: 286
<212> TYPE: PRT
<213> ORGANISM: Artificial Sequence
<220> FEATURE:
<223> OTHER INFORMATION: Made in Lab - anti-CLL-1 VHH DARIC binding
      component

<400> SEQUENCE: 19

Met Glu Thr Asp Thr Leu Leu Leu Trp Val Leu Leu Leu Trp Val Pro
 1               5                  10                  15

Gly Ser Thr Gly Glu Val Gln Leu Val Glu Ser Gly Gly Gly Glu Val
                20                  25                  30

Gln Pro Gly Gly Ser Leu Arg Leu Ser Cys Ala Ala Ser Gly Phe Thr
            35                  40                  45

Phe Arg Ile Asn Asp Met Gly Trp Tyr Arg Gln Ala Pro Gly Lys Glu
 50                  55                  60

Cys Glu Met Val Ala Gly Ile Ser Asn Asn Gly Phe Ser Thr Ala Tyr
 65                  70                  75                  80

Ala Glu Ser Val Lys Gly Arg Phe Thr Ile Ser Arg Asp Asn Ala Lys
                85                  90                  95

Asn Thr Val Tyr Leu Gln Met Ser Ser Leu Arg Ala Glu Asp Thr Ala
                100                 105                 110

Val Tyr Tyr Cys His Arg Thr Asp Glu Gly Ala Ala His Ala Cys Ser
            115                 120                 125

Arg Gly Gln Gly Thr Leu Val Thr Val Lys Pro Gly Gly Gly Ser
    130                 135                 140

Gly Val Gln Val Glu Thr Ile Ser Pro Gly Asp Gly Arg Thr Phe Pro
145                 150                 155                 160

Lys Arg Gly Gln Thr Cys Val Val His Tyr Thr Gly Met Leu Glu Asp
                165                 170                 175

Gly Lys Lys Phe Asp Ser Ser Arg Asp Arg Asn Lys Pro Phe Lys Phe
            180                 185                 190

Met Leu Gly Lys Gln Glu Val Ile Arg Gly Trp Glu Glu Gly Val Ala
            195                 200                 205

Gln Met Ser Val Gly Gln Arg Ala Lys Leu Thr Ile Ser Pro Asp Tyr
    210                 215                 220

Ala Tyr Gly Ala Thr Gly His Pro Gly Ile Ile Pro Pro His Ala Thr
225                 230                 235                 240

Leu Val Phe Asp Val Glu Leu Leu Lys Leu Glu Gly Gly Arg Met Ala
                245                 250                 255

Leu Ile Val Leu Gly Gly Val Ala Gly Leu Leu Leu Phe Ile Gly Leu
            260                 265                 270

Gly Ile Phe Phe Cys Val Arg Cys Arg His Arg Arg Gln
            275                 280                 285

<210> SEQ ID NO 20
<211> LENGTH: 612
<212> TYPE: PRT
<213> ORGANISM: Artificial Sequence
<220> FEATURE:
<223> OTHER INFORMATION: Made in Lab - anti-CLL-1 VHH DARIC fusion
      protein

<400> SEQUENCE: 20

Met Ala Leu Pro Val Thr Ala Leu Leu Leu Pro Leu Ala Leu Leu Leu
1               5                   10                  15

His Ala Ala Arg Pro Gly Ser Ile Leu Trp His Glu Met Trp His Glu
            20                  25                  30

Gly Leu Glu Glu Ala Ser Arg Leu Tyr Phe Gly Glu Arg Asn Val Lys
        35                  40                  45

Gly Met Phe Glu Val Leu Glu Pro Leu His Ala Met Met Glu Arg Gly
    50                  55                  60

Pro Gln Thr Leu Lys Glu Thr Ser Phe Asn Gln Ala Tyr Gly Arg Asp
65                  70                  75                  80

Leu Met Glu Ala Gln Glu Trp Cys Arg Lys Tyr Met Lys Ser Gly Asn
                85                  90                  95

Val Lys Asp Leu Leu Gln Ala Trp Asp Leu Tyr Tyr His Val Phe Arg
            100                 105                 110

Arg Ile Ser Lys Ala Ser Ala Gly Thr Gly Ser Asp Ile Tyr Ile Trp
        115                 120                 125

Ala Pro Leu Ala Gly Thr Cys Gly Val Leu Leu Leu Ser Leu Val Ile
    130                 135                 140

Thr Met His Lys Arg Gly Arg Lys Lys Leu Leu Tyr Ile Phe Lys Gln
145                 150                 155                 160

Pro Phe Met Arg Pro Val Gln Thr Thr Gln Glu Glu Asp Gly Cys Ser
                165                 170                 175

Cys Arg Phe Pro Glu Glu Glu Glu Gly Gly Cys Glu Leu Arg Val Lys

```
                180              185              190
Phe Ser Arg Ser Ala Asp Ala Pro Ala Tyr Gln Gln Gly Gln Asn Gln
            195              200              205
Leu Tyr Asn Glu Leu Asn Leu Gly Arg Arg Glu Glu Tyr Asp Val Leu
            210              215              220
Asp Lys Arg Arg Gly Arg Asp Pro Glu Met Gly Gly Lys Pro Arg Arg
225              230              235              240
Lys Asn Pro Gln Glu Gly Leu Tyr Asn Glu Leu Gln Lys Asp Lys Met
            245              250              255
Ala Glu Ala Tyr Ser Glu Ile Gly Met Lys Gly Glu Arg Arg Arg Gly
            260              265              270
Lys Gly His Asp Gly Leu Tyr Gln Gly Leu Ser Thr Ala Thr Lys Asp
            275              280              285
Thr Tyr Asp Ala Leu His Met Gln Ala Leu Pro Pro Arg Ser Gly Ser
            290              295              300
Gly Ala Thr Asn Phe Ser Leu Leu Lys Gln Ala Gly Asp Val Glu Glu
305              310              315              320
Asn Pro Gly Pro Ser Met Glu Thr Asp Thr Leu Leu Leu Trp Val Leu
            325              330              335
Leu Leu Trp Val Pro Gly Ser Thr Gly Glu Val Gln Leu Val Glu Ser
            340              345              350
Gly Gly Gly Glu Val Gln Pro Gly Gly Ser Leu Arg Leu Ser Cys Ala
            355              360              365
Ala Ser Gly Phe Leu Phe Ser Ile Tyr Asp Met Asn Trp Tyr Arg Gln
            370              375              380
Ala Pro Gly Lys Glu Arg Glu Trp Val Ala Gly Ile Thr Asn Asn Gly
385              390              395              400
Tyr Ser Thr Ala Tyr Ala Glu Ser Val Lys Gly Arg Phe Thr Ile Ser
            405              410              415
Arg Asp Asn Ala Lys Asn Thr Ile Tyr Leu Gln Met Ser Ser Leu Arg
            420              425              430
Ala Glu Asp Thr Ala Val Tyr Tyr Cys His Ala Asp Leu Thr Lys Ala
            435              440              445
Tyr Asp Val Glu Tyr Ala Trp Gly Gln Gly Thr Leu Val Thr Val Lys
            450              455              460
Pro Gly Gly Gly Ser Gly Val Gln Val Glu Thr Ile Ser Pro Gly
465              470              475              480
Asp Gly Arg Thr Phe Pro Lys Arg Gly Gln Thr Cys Val Val His Tyr
            485              490              495
Thr Gly Met Leu Glu Asp Gly Lys Lys Phe Asp Ser Ser Arg Asp Arg
            500              505              510
Asn Lys Pro Phe Lys Phe Met Leu Gly Lys Gln Glu Val Ile Arg Gly
            515              520              525
Trp Glu Glu Gly Val Ala Gln Met Ser Val Gly Gln Arg Ala Lys Leu
            530              535              540
Thr Ile Ser Pro Asp Tyr Ala Tyr Gly Ala Thr Gly His Pro Gly Ile
545              550              555              560
Ile Pro Pro His Ala Thr Leu Val Phe Asp Val Glu Leu Leu Lys Leu
            565              570              575
Glu Gly Gly Arg Met Ala Leu Ile Val Leu Gly Gly Val Ala Gly Leu
            580              585              590
Leu Leu Phe Ile Gly Leu Gly Ile Phe Phe Cys Val Arg Cys Arg His
            595              600              605
```

Arg Arg Arg Gln
    610

<210> SEQ ID NO 21
<211> LENGTH: 613
<212> TYPE: PRT
<213> ORGANISM: Artificial Sequence
<220> FEATURE:
<223> OTHER INFORMATION: Made in Lab - anti-CLL-1 VHH DARIC fusion
      protein

<400> SEQUENCE: 21

Met Ala Leu Pro Val Thr Ala Leu Leu Pro Leu Ala Leu Leu Leu
1               5                   10                  15

His Ala Ala Arg Pro Gly Ser Ile Leu Trp His Glu Met Trp His Glu
            20                  25                  30

Gly Leu Glu Glu Ala Ser Arg Leu Tyr Phe Gly Glu Arg Asn Val Lys
        35                  40                  45

Gly Met Phe Glu Val Leu Glu Pro Leu His Ala Met Met Glu Arg Gly
    50                  55                  60

Pro Gln Thr Leu Lys Glu Thr Ser Phe Asn Gln Ala Tyr Gly Arg Asp
65                  70                  75                  80

Leu Met Glu Ala Gln Glu Trp Cys Arg Lys Tyr Met Lys Ser Gly Asn
                85                  90                  95

Val Lys Asp Leu Leu Gln Ala Trp Asp Leu Tyr Tyr His Val Phe Arg
            100                 105                 110

Arg Ile Ser Lys Ala Ser Ala Gly Thr Gly Ser Asp Ile Tyr Ile Trp
        115                 120                 125

Ala Pro Leu Ala Gly Thr Cys Gly Val Leu Leu Leu Ser Leu Val Ile
    130                 135                 140

Thr Met His Lys Arg Gly Arg Lys Lys Leu Leu Tyr Ile Phe Lys Gln
145                 150                 155                 160

Pro Phe Met Arg Pro Val Gln Thr Thr Gln Glu Glu Asp Gly Cys Ser
                165                 170                 175

Cys Arg Phe Pro Glu Glu Glu Glu Gly Gly Cys Glu Leu Arg Val Lys
            180                 185                 190

Phe Ser Arg Ser Ala Asp Ala Pro Ala Tyr Gln Gln Gly Gln Asn Gln
        195                 200                 205

Leu Tyr Asn Glu Leu Asn Leu Gly Arg Arg Glu Glu Tyr Asp Val Leu
    210                 215                 220

Asp Lys Arg Arg Gly Arg Asp Pro Glu Met Gly Gly Lys Pro Arg Arg
225                 230                 235                 240

Lys Asn Pro Gln Glu Gly Leu Tyr Asn Glu Leu Gln Lys Asp Lys Met
                245                 250                 255

Ala Glu Ala Tyr Ser Glu Ile Gly Met Lys Gly Glu Arg Arg Arg Gly
            260                 265                 270

Lys Gly His Asp Gly Leu Tyr Gln Gly Leu Ser Thr Ala Thr Lys Asp
        275                 280                 285

Thr Tyr Asp Ala Leu His Met Gln Ala Leu Pro Pro Arg Ser Gly Ser
    290                 295                 300

Gly Ala Thr Asn Phe Ser Leu Leu Lys Gln Ala Gly Asp Val Glu Glu
305                 310                 315                 320

Asn Pro Gly Pro Ser Met Glu Thr Asp Thr Leu Leu Leu Trp Val Leu
                325                 330                 335

Leu Leu Trp Val Pro Gly Ser Thr Gly Glu Val Gln Leu Val Glu Ser

-continued

```
                340             345             350
Gly Gly Gly Glu Val Gln Pro Gly Gly Ser Leu Arg Leu Ser Cys Ala
            355                 360                 365
Ala Ser Gly Phe Thr Phe Ser Val Tyr Asp Met Asn Trp Tyr Arg Gln
            370                 375                 380
Ala Pro Gly Lys Glu Arg Glu Trp Val Ser Gly Ile Ser Asn Asn Gly
385                 390                 395                 400
Phe Ser Thr Ala Tyr Ala Glu Ser Val Lys Gly Arg Phe Thr Ile Ser
                405                 410                 415
Arg Asp Asn Ala Lys Asn Thr Leu Tyr Leu Gln Met Ser Ser Leu Arg
                420                 425                 430
Ala Glu Asp Thr Ala Val Tyr Tyr Cys Asn Leu Asp Val His Gly Arg
                435                 440                 445
Val Gly Ala Gln Gly Asp Tyr Trp Gly Gln Gly Thr Leu Val Thr Val
            450                 455                 460
Lys Pro Gly Gly Gly Ser Gly Val Gln Val Glu Thr Ile Ser Pro
465                 470                 475                 480
Gly Asp Gly Arg Thr Phe Pro Lys Arg Gly Gln Thr Cys Val Val His
                485                 490                 495
Tyr Thr Gly Met Leu Glu Asp Gly Lys Lys Phe Asp Ser Ser Arg Asp
                500                 505                 510
Arg Asn Lys Pro Phe Lys Phe Met Leu Gly Lys Gln Glu Val Ile Arg
                515                 520                 525
Gly Trp Glu Glu Gly Val Ala Gln Met Ser Val Gly Gln Arg Ala Lys
            530                 535                 540
Leu Thr Ile Ser Pro Asp Tyr Ala Tyr Gly Ala Thr Gly His Pro Gly
545                 550                 555                 560
Ile Ile Pro Pro His Ala Thr Leu Val Phe Asp Val Glu Leu Leu Lys
                565                 570                 575
Leu Glu Gly Gly Arg Met Ala Leu Ile Val Leu Gly Val Ala Gly
            580                 585                 590
Leu Leu Leu Phe Ile Gly Leu Gly Ile Phe Phe Cys Val Arg Cys Arg
            595                 600                 605
His Arg Arg Arg Gln
    610

<210> SEQ ID NO 22
<211> LENGTH: 621
<212> TYPE: PRT
<213> ORGANISM: Artificial Sequence
<220> FEATURE:
<223> OTHER INFORMATION: Made in Lab - anti-CLL-1 VHH DARIC fusion
      protein

<400> SEQUENCE: 22

Met Ala Leu Pro Val Thr Ala Leu Leu Leu Pro Leu Ala Leu Leu Leu
1               5                   10                  15
His Ala Ala Arg Pro Gly Ser Ile Leu Trp His Glu Met Trp His Glu
                20                  25                  30
Gly Leu Glu Glu Ala Ser Arg Leu Tyr Phe Gly Glu Arg Asn Val Lys
            35                  40                  45
Gly Met Phe Glu Val Leu Glu Pro Leu His Ala Met Met Glu Arg Gly
        50                  55                  60
Pro Gln Thr Leu Lys Glu Thr Ser Phe Asn Gln Ala Tyr Gly Arg Asp
65                  70                  75                  80
```

-continued

Leu Met Glu Ala Gln Glu Trp Cys Arg Lys Tyr Met Lys Ser Gly Asn
            85                  90                  95

Val Lys Asp Leu Leu Gln Ala Trp Asp Leu Tyr Tyr His Val Phe Arg
        100                 105                 110

Arg Ile Ser Lys Ala Ser Ala Gly Thr Gly Ser Asp Ile Tyr Ile Trp
            115                 120                 125

Ala Pro Leu Ala Gly Thr Cys Gly Val Leu Leu Ser Leu Val Ile
        130                 135                 140

Thr Met His Lys Arg Gly Arg Lys Lys Leu Leu Tyr Ile Phe Lys Gln
145                 150                 155                 160

Pro Phe Met Arg Pro Val Gln Thr Thr Gln Glu Glu Asp Gly Cys Ser
                165                 170                 175

Cys Arg Phe Pro Glu Glu Glu Gly Gly Cys Glu Leu Arg Val Lys
        180                 185                 190

Phe Ser Arg Ser Ala Asp Ala Pro Ala Tyr Gln Gln Gly Gln Asn Gln
            195                 200                 205

Leu Tyr Asn Glu Leu Asn Leu Gly Arg Arg Glu Glu Tyr Asp Val Leu
        210                 215                 220

Asp Lys Arg Arg Gly Arg Asp Pro Glu Met Gly Gly Lys Pro Arg Arg
225                 230                 235                 240

Lys Asn Pro Gln Glu Gly Leu Tyr Asn Glu Leu Gln Lys Asp Lys Met
                245                 250                 255

Ala Glu Ala Tyr Ser Glu Ile Gly Met Lys Gly Glu Arg Arg Arg Gly
            260                 265                 270

Lys Gly His Asp Gly Leu Tyr Gln Gly Leu Ser Thr Ala Thr Lys Asp
        275                 280                 285

Thr Tyr Asp Ala Leu His Met Gln Ala Leu Pro Pro Arg Ser Gly Ser
        290                 295                 300

Gly Ala Thr Asn Phe Ser Leu Leu Lys Gln Ala Gly Asp Val Glu Glu
305                 310                 315                 320

Asn Pro Gly Pro Ser Met Glu Thr Asp Thr Leu Leu Leu Trp Val Leu
                325                 330                 335

Leu Leu Trp Val Pro Gly Ser Thr Gly Glu Val Gln Leu Val Glu Ser
        340                 345                 350

Gly Gly Gly Glu Val Gln Pro Gly Gly Ser Leu Arg Leu Ser Cys Ala
        355                 360                 365

Ala Ser Gly Phe Thr Phe Asp Asp Tyr Ala Ile Gly Trp Phe Arg Gln
        370                 375                 380

Ala Pro Gly Lys Glu Arg Glu Gly Val Ser Thr Ile Ser Ser Ser Asp
385                 390                 395                 400

Gly Ser Thr Tyr Tyr Ala Glu Ser Val Lys Gly Arg Phe Thr Ile Ser
                405                 410                 415

Arg Asp Asn Ala Lys Asn Thr Val Tyr Leu Gln Met Ser Ser Leu Arg
            420                 425                 430

Ala Glu Asp Thr Ala Val Tyr Tyr Cys Ala Leu Arg Glu Gly Leu Pro
        435                 440                 445

Leu Leu Leu Asp Thr Leu Trp Arg Gln Pro Val Glu Tyr Asp Tyr Trp
        450                 455                 460

Gly Gln Gly Thr Gln Val Thr Val Lys Pro Gly Gly Gly Gly Ser Gly
465                 470                 475                 480

Val Gln Val Glu Thr Ile Ser Pro Gly Asp Gly Arg Thr Phe Pro Lys
        485                 490                 495

Arg Gly Gln Thr Cys Val Val His Tyr Thr Gly Met Leu Glu Asp Gly

-continued

```
                500                 505                 510
Lys Lys Phe Asp Ser Ser Arg Asp Arg Asn Lys Pro Phe Lys Phe Met
            515                 520                 525

Leu Gly Lys Gln Glu Val Ile Arg Gly Trp Glu Gly Val Ala Gln
        530                 535             540

Met Ser Val Gly Gln Arg Ala Lys Leu Thr Ile Ser Pro Asp Tyr Ala
545                 550                 555                 560

Tyr Gly Ala Thr Gly His Pro Gly Ile Ile Pro Pro His Ala Thr Leu
                565                 570                 575

Val Phe Asp Val Glu Leu Leu Lys Leu Glu Gly Gly Arg Met Ala Leu
            580                 585                 590

Ile Val Leu Gly Gly Val Ala Gly Leu Leu Leu Phe Ile Gly Leu Gly
        595                 600                 605

Ile Phe Phe Cys Val Arg Cys Arg His Arg Arg Gln
        610                 615                 620

<210> SEQ ID NO 23
<211> LENGTH: 608
<212> TYPE: PRT
<213> ORGANISM: Artificial Sequence
<220> FEATURE:
<223> OTHER INFORMATION: Made in Lab - anti-CLL-1 VHH DARIC fusion
      protein

<400> SEQUENCE: 23

Met Ala Leu Pro Val Thr Ala Leu Leu Leu Pro Leu Ala Leu Leu Leu
1               5                   10                  15

His Ala Ala Arg Pro Gly Ser Ile Leu Trp His Glu Met Trp His Glu
            20                  25                  30

Gly Leu Glu Glu Ala Ser Arg Leu Tyr Phe Gly Glu Arg Asn Val Lys
        35                  40                  45

Gly Met Phe Glu Val Leu Glu Pro Leu His Ala Met Met Glu Arg Gly
    50                  55                  60

Pro Gln Thr Leu Lys Glu Thr Ser Phe Asn Gln Ala Tyr Gly Arg Asp
65                  70                  75                  80

Leu Met Glu Ala Gln Glu Trp Cys Arg Lys Tyr Met Lys Ser Gly Asn
                85                  90                  95

Val Lys Asp Leu Leu Gln Ala Trp Asp Leu Tyr Tyr His Val Phe Arg
            100                 105                 110

Arg Ile Ser Lys Ala Ser Ala Gly Thr Gly Ser Asp Ile Tyr Ile Trp
        115                 120                 125

Ala Pro Leu Ala Gly Thr Cys Gly Val Leu Leu Leu Ser Leu Val Ile
    130                 135                 140

Thr Met His Lys Arg Gly Arg Lys Lys Leu Leu Tyr Ile Phe Lys Gln
145                 150                 155                 160

Pro Phe Met Arg Pro Val Gln Thr Thr Gln Glu Glu Asp Gly Cys Ser
                165                 170                 175

Cys Arg Phe Pro Glu Glu Glu Glu Gly Gly Cys Glu Leu Arg Val Lys
            180                 185                 190

Phe Ser Arg Ser Ala Asp Ala Pro Ala Tyr Gln Gln Gly Gln Asn Gln
        195                 200                 205

Leu Tyr Asn Glu Leu Asn Leu Gly Arg Arg Glu Glu Tyr Asp Val Leu
    210                 215                 220

Asp Lys Arg Arg Gly Arg Asp Pro Glu Met Gly Gly Lys Pro Arg Arg
225                 230                 235                 240
```

```
Lys Asn Pro Gln Glu Gly Leu Tyr Asn Glu Leu Gln Lys Asp Lys Met
                245                 250                 255

Ala Glu Ala Tyr Ser Glu Ile Gly Met Lys Gly Glu Arg Arg Arg Gly
            260                 265                 270

Lys Gly His Asp Gly Leu Tyr Gln Gly Leu Ser Thr Ala Thr Lys Asp
        275                 280                 285

Thr Tyr Asp Ala Leu His Met Gln Ala Leu Pro Pro Arg Ser Gly Ser
    290                 295                 300

Gly Ala Thr Asn Phe Ser Leu Leu Lys Gln Ala Gly Asp Val Glu Glu
305                 310                 315                 320

Asn Pro Gly Pro Ser Met Glu Thr Asp Thr Leu Leu Leu Trp Val Leu
                325                 330                 335

Leu Leu Trp Val Pro Gly Ser Thr Gly Glu Val Gln Leu Val Glu Ser
            340                 345                 350

Gly Gly Gly Glu Val Gln Pro Gly Gly Ser Leu Arg Leu Ser Cys Ala
        355                 360                 365

Ala Ser Gly Leu Leu Phe Ser Ile Tyr Asp Met Asn Trp Tyr Arg Gln
    370                 375                 380

Ala Pro Gly Lys Glu Arg Glu Trp Val Ala Gly Ile Thr Asn Asn Gly
385                 390                 395                 400

Tyr Ser Thr Ala Tyr Ala Glu Ser Val Lys Gly Arg Phe Thr Ile Ser
                405                 410                 415

Arg Asp Asn Ala Lys Asn Thr Val Tyr Leu Gln Met Ser Ser Leu Arg
            420                 425                 430

Ala Glu Asp Thr Ala Val Tyr Tyr Cys His Thr Asp Glu Trp Gly Arg
        435                 440                 445

Glu Tyr Trp Gly Gln Gly Thr Leu Val Thr Val Lys Pro Gly Gly Gly
    450                 455                 460

Gly Ser Gly Val Gln Val Glu Thr Ile Ser Pro Gly Asp Gly Arg Thr
465                 470                 475                 480

Phe Pro Lys Arg Gly Gln Thr Cys Val Val His Tyr Thr Gly Met Leu
                485                 490                 495

Glu Asp Gly Lys Lys Phe Asp Ser Ser Arg Asp Arg Asn Lys Pro Phe
            500                 505                 510

Lys Phe Met Leu Gly Lys Gln Glu Val Ile Arg Gly Trp Glu Glu Gly
        515                 520                 525

Val Ala Gln Met Ser Val Gly Gln Arg Ala Lys Leu Thr Ile Ser Pro
    530                 535                 540

Asp Tyr Ala Tyr Gly Ala Thr Gly His Pro Gly Ile Ile Pro Pro His
545                 550                 555                 560

Ala Thr Leu Val Phe Asp Val Glu Leu Leu Lys Leu Glu Gly Gly Arg
                565                 570                 575

Met Ala Leu Ile Val Leu Gly Val Ala Gly Leu Leu Leu Phe Ile
            580                 585                 590

Gly Leu Gly Ile Phe Phe Cys Val Arg Cys Arg His Arg Arg Gln
        595                 600                 605

<210> SEQ ID NO 24
<211> LENGTH: 604
<212> TYPE: PRT
<213> ORGANISM: Artificial Sequence
<220> FEATURE:
<223> OTHER INFORMATION: Made in Lab - anti-CLL-1 VHH DARIC fusion
      protein

<400> SEQUENCE: 24
```

```
Met Ala Leu Pro Val Thr Ala Leu Leu Leu Pro Leu Ala Leu Leu Leu
1               5                   10                  15

His Ala Ala Arg Pro Gly Ser Ile Leu Trp His Glu Met Trp His Glu
            20                  25                  30

Gly Leu Glu Glu Ala Ser Arg Leu Tyr Phe Gly Glu Arg Asn Val Lys
            35                  40                  45

Gly Met Phe Glu Val Leu Glu Pro Leu His Ala Met Met Glu Arg Gly
50                  55                  60

Pro Gln Thr Leu Lys Glu Thr Ser Phe Asn Gln Ala Tyr Gly Arg Asp
65                  70                  75                  80

Leu Met Glu Ala Gln Glu Trp Cys Arg Lys Tyr Met Lys Ser Gly Asn
                85                  90                  95

Val Lys Asp Leu Leu Gln Ala Trp Asp Leu Tyr Tyr His Val Phe Arg
                100                 105                 110

Arg Ile Ser Lys Ala Ser Ala Gly Thr Gly Ser Asp Ile Tyr Ile Trp
            115                 120                 125

Ala Pro Leu Ala Gly Thr Cys Gly Val Leu Leu Ser Leu Val Ile
            130                 135                 140

Thr Met His Lys Arg Gly Arg Lys Lys Leu Leu Tyr Ile Phe Lys Gln
145                 150                 155                 160

Pro Phe Met Arg Pro Val Gln Thr Thr Gln Glu Glu Asp Gly Cys Ser
                165                 170                 175

Cys Arg Phe Pro Glu Glu Glu Glu Gly Gly Cys Glu Leu Arg Val Lys
                180                 185                 190

Phe Ser Arg Ser Ala Asp Ala Pro Ala Tyr Gln Gln Gly Gln Asn Gln
            195                 200                 205

Leu Tyr Asn Glu Leu Asn Leu Gly Arg Arg Glu Glu Tyr Asp Val Leu
210                 215                 220

Asp Lys Arg Arg Gly Arg Asp Pro Glu Met Gly Gly Lys Pro Arg Arg
225                 230                 235                 240

Lys Asn Pro Gln Glu Gly Leu Tyr Asn Glu Leu Gln Lys Asp Lys Met
                245                 250                 255

Ala Glu Ala Tyr Ser Glu Ile Gly Met Lys Gly Glu Arg Arg Arg Gly
                260                 265                 270

Lys Gly His Asp Gly Leu Tyr Gln Gly Leu Ser Thr Ala Thr Lys Asp
            275                 280                 285

Thr Tyr Asp Ala Leu His Met Gln Ala Leu Pro Pro Arg Ser Gly Ser
    290                 295                 300

Gly Ala Thr Asn Phe Ser Leu Leu Lys Gln Ala Gly Asp Val Glu Glu
305                 310                 315                 320

Asn Pro Gly Pro Ser Met Glu Thr Asp Thr Leu Leu Leu Trp Val Leu
                325                 330                 335

Leu Leu Trp Val Pro Gly Ser Thr Gly Glu Val Gln Leu Val Glu Ser
            340                 345                 350

Gly Gly Gly Glu Val Gln Pro Gly Gly Ser Leu Arg Leu Ser Cys Ala
            355                 360                 365

Ala Ser Gly Arg Thr Phe Glu Tyr Asp Asp Met Val Trp Phe Arg Gln
370                 375                 380

Ala Pro Gly Lys Glu Arg Glu Glu Val Ala Gly Ile Ser Trp Ser Gly
385                 390                 395                 400

Gly Ser Ile Tyr Tyr Ala Glu Ser Val Lys Gly Arg Phe Ser Ile Ser
                405                 410                 415
```

-continued

```
Arg Asp Asn Ala Lys Asn Thr Val Tyr Leu Glu Met Asn Arg Leu Lys
            420                 425                 430

Pro Glu Asp Thr Ala Val Tyr Tyr Cys Asn Val Gly Ser Tyr Trp Gly
        435                 440                 445

Gln Gly Thr Leu Val Thr Val Lys Pro Gly Gly Gly Ser Gly Val
    450                 455                 460

Gln Val Glu Thr Ile Ser Pro Gly Asp Gly Arg Thr Phe Pro Lys Arg
465                 470                 475                 480

Gly Gln Thr Cys Val Val His Tyr Thr Gly Met Leu Glu Asp Gly Lys
                485                 490                 495

Lys Phe Asp Ser Ser Arg Asp Arg Asn Lys Pro Phe Lys Phe Met Leu
            500                 505                 510

Gly Lys Gln Glu Val Ile Arg Gly Trp Glu Glu Gly Val Ala Gln Met
        515                 520                 525

Ser Val Gly Gln Arg Ala Lys Leu Thr Ile Ser Pro Asp Tyr Ala Tyr
    530                 535                 540

Gly Ala Thr Gly His Pro Gly Ile Ile Pro Pro His Ala Thr Leu Val
545                 550                 555                 560

Phe Asp Val Glu Leu Leu Lys Leu Glu Gly Gly Arg Met Ala Leu Ile
                565                 570                 575

Val Leu Gly Gly Val Ala Gly Leu Leu Leu Phe Ile Gly Leu Gly Ile
            580                 585                 590

Phe Phe Cys Val Arg Cys Arg His Arg Arg Gln
        595                 600

<210> SEQ ID NO 25
<211> LENGTH: 611
<212> TYPE: PRT
<213> ORGANISM: Artificial Sequence
<220> FEATURE:
<223> OTHER INFORMATION: Made in Lab - anti-CLL-1 VHH DARIC fusion
      protein

<400> SEQUENCE: 25

Met Ala Leu Pro Val Thr Ala Leu Leu Leu Pro Leu Ala Leu Leu Leu
1               5                   10                  15

His Ala Ala Arg Pro Gly Ser Ile Leu Trp His Glu Met Trp His Glu
            20                  25                  30

Gly Leu Glu Glu Ala Ser Arg Leu Tyr Phe Gly Glu Arg Asn Val Lys
        35                  40                  45

Gly Met Phe Glu Val Leu Glu Pro Leu His Ala Met Met Glu Arg Gly
    50                  55                  60

Pro Gln Thr Leu Lys Glu Thr Ser Phe Asn Gln Ala Tyr Gly Arg Asp
65                  70                  75                  80

Leu Met Glu Ala Gln Glu Trp Cys Arg Lys Tyr Met Lys Ser Gly Asn
                85                  90                  95

Val Lys Asp Leu Leu Gln Ala Trp Asp Leu Tyr Tyr His Val Phe Arg
            100                 105                 110

Arg Ile Ser Lys Ala Ser Ala Gly Thr Gly Ser Asp Ile Tyr Ile Trp
        115                 120                 125

Ala Pro Leu Ala Gly Thr Cys Gly Val Leu Leu Leu Ser Leu Val Ile
    130                 135                 140

Thr Met His Lys Arg Gly Arg Lys Lys Leu Leu Tyr Ile Phe Lys Gln
145                 150                 155                 160

Pro Phe Met Arg Pro Val Gln Thr Thr Gln Glu Glu Asp Gly Cys Ser
                165                 170                 175
```

```
Cys Arg Phe Pro Glu Glu Glu Gly Gly Cys Glu Leu Arg Val Lys
            180                 185                 190

Phe Ser Arg Ser Ala Asp Ala Pro Ala Tyr Gln Gln Gly Gln Asn Gln
            195                 200                 205

Leu Tyr Asn Glu Leu Asn Leu Gly Arg Arg Gly Glu Tyr Asp Val Leu
            210                 215                 220

Asp Lys Arg Arg Gly Arg Asp Pro Glu Met Gly Gly Lys Pro Arg Arg
225                 230                 235                 240

Lys Asn Pro Gln Glu Gly Leu Tyr Asn Glu Leu Gln Lys Asp Lys Met
                245                 250                 255

Ala Glu Ala Tyr Ser Glu Ile Gly Met Lys Gly Glu Arg Arg Arg Gly
            260                 265                 270

Lys Gly His Asp Gly Leu Tyr Gln Gly Leu Ser Thr Ala Thr Lys Asp
            275                 280                 285

Thr Tyr Asp Ala Leu His Met Gln Ala Leu Pro Pro Arg Ser Gly Ser
            290                 295                 300

Gly Ala Thr Asn Phe Ser Leu Leu Lys Gln Ala Gly Asp Val Glu Glu
305                 310                 315                 320

Asn Pro Gly Pro Ser Met Glu Thr Asp Thr Leu Leu Leu Trp Val Leu
                325                 330                 335

Leu Leu Trp Val Pro Gly Ser Thr Gly Glu Val Gln Leu Val Glu Ser
            340                 345                 350

Gly Gly Gly Glu Val Gln Pro Gly Gly Ser Leu Arg Leu Ser Cys Ala
            355                 360                 365

Ala Ser Gly Phe Thr Phe Arg Ile Asn Asp Met Gly Trp Tyr Arg Gln
            370                 375                 380

Ala Pro Gly Lys Glu Cys Glu Met Val Ala Gly Ile Ser Asn Asn Gly
385                 390                 395                 400

Phe Ser Thr Ala Tyr Ala Glu Ser Val Lys Gly Arg Phe Thr Ile Ser
                405                 410                 415

Arg Asp Asn Ala Lys Asn Thr Val Tyr Leu Gln Met Ser Ser Leu Arg
            420                 425                 430

Ala Glu Asp Thr Ala Val Tyr Tyr Cys His Arg Thr Asp Glu Gly Ala
            435                 440                 445

Ala His Ala Cys Ser Arg Gly Gln Gly Thr Leu Val Thr Val Lys Pro
            450                 455                 460

Gly Gly Gly Gly Ser Gly Val Gln Val Glu Thr Ile Ser Pro Gly Asp
465                 470                 475                 480

Gly Arg Thr Phe Pro Lys Arg Gly Gln Thr Cys Val Val His Tyr Thr
                485                 490                 495

Gly Met Leu Glu Asp Gly Lys Lys Phe Asp Ser Ser Arg Asp Arg Asn
            500                 505                 510

Lys Pro Phe Lys Phe Met Leu Gly Lys Gln Glu Val Ile Arg Gly Trp
            515                 520                 525

Glu Glu Gly Val Ala Gln Met Ser Val Gly Gln Arg Ala Lys Leu Thr
            530                 535                 540

Ile Ser Pro Asp Tyr Ala Tyr Gly Ala Thr Gly His Pro Gly Ile Ile
545                 550                 555                 560

Pro Pro His Ala Thr Leu Val Phe Asp Val Glu Leu Leu Lys Leu Glu
                565                 570                 575

Gly Gly Arg Met Ala Leu Ile Val Leu Gly Gly Val Ala Gly Leu Leu
            580                 585                 590
```

```
Leu Phe Ile Gly Leu Gly Ile Phe Phe Cys Val Arg Cys Arg His Arg
            595                 600                 605

Arg Arg Gln
    610

<210> SEQ ID NO 26
<211> LENGTH: 644
<212> TYPE: PRT
<213> ORGANISM: Artificial Sequence
<220> FEATURE:
<223> OTHER INFORMATION: Made in Lab - anti-CLL1 DARIC.OX40 fusion
      protein

<400> SEQUENCE: 26

Met Ala Leu Pro Val Thr Ala Leu Leu Leu Pro Leu Ala Leu Leu Leu
1               5                   10                  15

His Ala Ala Arg Pro Gly Ser Ile Leu Trp His Glu Met Trp His Glu
            20                  25                  30

Gly Leu Glu Glu Ala Ser Arg Leu Tyr Phe Gly Glu Arg Asn Val Lys
        35                  40                  45

Gly Met Phe Glu Val Leu Glu Pro Leu His Ala Met Met Glu Arg Gly
    50                  55                  60

Pro Gln Thr Leu Lys Glu Thr Ser Phe Asn Gln Ala Tyr Gly Arg Asp
65                  70                  75                  80

Leu Met Glu Ala Gln Glu Trp Cys Arg Lys Tyr Met Lys Ser Gly Asn
                85                  90                  95

Val Lys Asp Leu Leu Gln Ala Trp Asp Leu Tyr Tyr His Val Phe Arg
            100                 105                 110

Arg Ile Ser Lys Ala Ser Ala Gly Thr Gly Ser Asp Ile Tyr Ile Trp
        115                 120                 125

Ala Pro Leu Ala Gly Thr Cys Gly Val Leu Leu Leu Ser Leu Val Ile
    130                 135                 140

Thr Met His Lys Arg Gly Arg Lys Lys Leu Leu Tyr Ile Phe Lys Gln
145                 150                 155                 160

Pro Phe Met Arg Pro Val Gln Thr Thr Gln Glu Glu Asp Gly Cys Ser
                165                 170                 175

Cys Arg Phe Pro Glu Glu Glu Glu Gly Gly Cys Glu Leu Arg Val Lys
            180                 185                 190

Phe Ser Arg Ser Ala Asp Ala Pro Ala Tyr Gln Gln Gly Gln Asn Gln
        195                 200                 205

Leu Tyr Asn Glu Leu Asn Leu Gly Arg Arg Glu Glu Tyr Asp Val Leu
    210                 215                 220

Asp Lys Arg Arg Gly Arg Asp Pro Glu Met Gly Gly Lys Pro Arg Arg
225                 230                 235                 240

Lys Asn Pro Gln Glu Gly Leu Tyr Asn Glu Leu Gln Lys Asp Lys Met
                245                 250                 255

Ala Glu Ala Tyr Ser Glu Ile Gly Met Lys Gly Glu Arg Arg Arg Gly
            260                 265                 270

Lys Gly His Asp Gly Leu Tyr Gln Gly Leu Ser Thr Ala Thr Lys Asp
        275                 280                 285

Thr Tyr Asp Ala Leu His Met Gln Ala Leu Pro Pro Arg Ser Gly Ser
    290                 295                 300

Gly Ala Thr Asn Phe Ser Leu Leu Lys Gln Ala Gly Asp Val Glu Glu
305                 310                 315                 320

Asn Pro Gly Pro Ser Met Glu Thr Asp Thr Leu Leu Leu Trp Val Leu
                325                 330                 335
```

```
Leu Leu Trp Val Pro Gly Ser Thr Gly Glu Val Gln Leu Val Glu Ser
                340                 345                 350

Gly Gly Gly Glu Val Gln Pro Gly Gly Ser Leu Arg Leu Ser Cys Ala
            355                 360                 365

Ala Ser Gly Phe Leu Phe Ser Ile Tyr Asp Met Asn Trp Tyr Arg Gln
370                 375                 380

Ala Pro Gly Lys Glu Arg Glu Trp Val Ala Gly Ile Thr Asn Asn Gly
385                 390                 395                 400

Tyr Ser Thr Ala Tyr Ala Glu Ser Val Lys Gly Arg Phe Thr Ile Ser
                405                 410                 415

Arg Asp Asn Ala Lys Asn Thr Ile Tyr Leu Gln Met Ser Ser Leu Arg
            420                 425                 430

Ala Glu Asp Thr Ala Val Tyr Tyr Cys His Ala Asp Leu Thr Lys Ala
        435                 440                 445

Tyr Asp Val Glu Tyr Ala Trp Gly Gln Gly Thr Leu Val Thr Val Lys
    450                 455                 460

Pro Gly Gly Gly Gly Ser Gly Val Gln Val Glu Thr Ile Ser Pro Gly
465                 470                 475                 480

Asp Gly Arg Thr Phe Pro Lys Arg Gly Gln Thr Cys Val Val His Tyr
                485                 490                 495

Thr Gly Met Leu Glu Asp Gly Lys Lys Phe Asp Ser Ser Arg Asp Arg
            500                 505                 510

Asn Lys Pro Phe Lys Phe Met Leu Gly Lys Gln Glu Val Ile Arg Gly
        515                 520                 525

Trp Glu Glu Gly Val Ala Gln Met Ser Val Gly Gln Arg Ala Lys Leu
    530                 535                 540

Thr Ile Ser Pro Asp Tyr Ala Tyr Gly Ala Thr Gly His Pro Gly Ile
545                 550                 555                 560

Ile Pro Pro His Ala Thr Leu Val Phe Asp Val Glu Leu Leu Lys Leu
                565                 570                 575

Glu Gly Gly Arg Met Ala Leu Ile Val Leu Gly Gly Val Ala Gly Leu
            580                 585                 590

Leu Leu Phe Ile Gly Leu Gly Ile Phe Phe Ala Leu Tyr Leu Leu Arg
        595                 600                 605

Arg Asp Gln Arg Leu Pro Pro Asp Ala His Lys Pro Pro Gly Gly Gly
    610                 615                 620

Ser Phe Arg Thr Pro Ile Gln Glu Glu Gln Ala Asp Ala His Ser Thr
625                 630                 635                 640

Leu Ala Lys Ile

<210> SEQ ID NO 27
<211> LENGTH: 645
<212> TYPE: PRT
<213> ORGANISM: Artificial Sequence
<220> FEATURE:
<223> OTHER INFORMATION: Made in Lab - anti-CLL1 DARIC.OX40 fusion
      protein

<400> SEQUENCE: 27

Met Ala Leu Pro Val Thr Ala Leu Leu Leu Pro Leu Ala Leu Leu Leu
1               5                   10                  15

His Ala Ala Arg Pro Gly Ser Ile Leu Trp His Glu Met Trp His Glu
            20                  25                  30

Gly Leu Glu Glu Ala Ser Arg Leu Tyr Phe Gly Glu Arg Asn Val Lys
        35                  40                  45
```

```
Gly Met Phe Glu Val Leu Glu Pro Leu His Ala Met Met Glu Arg Gly
     50                  55                  60

Pro Gln Thr Leu Lys Glu Thr Ser Phe Asn Gln Ala Tyr Gly Arg Asp
 65                  70                  75                  80

Leu Met Glu Ala Gln Glu Trp Cys Arg Lys Tyr Met Lys Ser Gly Asn
                 85                  90                  95

Val Lys Asp Leu Leu Gln Ala Trp Asp Leu Tyr Tyr His Val Phe Arg
            100                 105                 110

Arg Ile Ser Lys Ala Ser Ala Gly Thr Gly Ser Asp Ile Tyr Ile Trp
        115                 120                 125

Ala Pro Leu Ala Gly Thr Cys Gly Val Leu Leu Ser Leu Val Ile
    130                 135                 140

Thr Met His Lys Arg Gly Arg Lys Lys Leu Leu Tyr Ile Phe Lys Gln
145                 150                 155                 160

Pro Phe Met Arg Pro Val Gln Thr Thr Gln Glu Glu Asp Gly Cys Ser
                165                 170                 175

Cys Arg Phe Pro Glu Glu Glu Gly Gly Cys Glu Leu Arg Val Lys
            180                 185                 190

Phe Ser Arg Ser Ala Asp Ala Pro Ala Tyr Gln Gln Gly Gln Asn Gln
        195                 200                 205

Leu Tyr Asn Glu Leu Asn Leu Gly Arg Arg Glu Glu Tyr Asp Val Leu
    210                 215                 220

Asp Lys Arg Arg Gly Arg Asp Pro Glu Met Gly Gly Lys Pro Arg Arg
225                 230                 235                 240

Lys Asn Pro Gln Glu Gly Leu Tyr Asn Glu Leu Gln Lys Asp Lys Met
                245                 250                 255

Ala Glu Ala Tyr Ser Glu Ile Gly Met Lys Gly Glu Arg Arg Arg Gly
            260                 265                 270

Lys Gly His Asp Gly Leu Tyr Gln Gly Leu Ser Thr Ala Thr Lys Asp
        275                 280                 285

Thr Tyr Asp Ala Leu His Met Gln Ala Leu Pro Pro Arg Ser Gly Ser
    290                 295                 300

Gly Ala Thr Asn Phe Ser Leu Leu Lys Gln Ala Gly Asp Val Glu Glu
305                 310                 315                 320

Asn Pro Gly Pro Ser Met Glu Thr Asp Thr Leu Leu Leu Trp Val Leu
                325                 330                 335

Leu Leu Trp Val Pro Gly Ser Thr Gly Glu Val Gln Leu Val Glu Ser
            340                 345                 350

Gly Gly Gly Glu Val Gln Pro Gly Gly Ser Leu Arg Leu Ser Cys Ala
        355                 360                 365

Ala Ser Gly Phe Thr Phe Ser Val Tyr Asp Met Asn Trp Tyr Arg Gln
    370                 375                 380

Ala Pro Gly Lys Glu Arg Glu Trp Val Ser Gly Ile Ser Asn Asn Gly
385                 390                 395                 400

Phe Ser Thr Ala Tyr Ala Glu Ser Val Lys Gly Arg Phe Thr Ile Ser
                405                 410                 415

Arg Asp Asn Ala Lys Asn Thr Leu Tyr Leu Gln Met Ser Ser Leu Arg
            420                 425                 430

Ala Glu Asp Thr Ala Val Tyr Tyr Cys Asn Leu Asp Val His Gly Arg
        435                 440                 445

Val Gly Ala Gln Gly Asp Tyr Trp Gly Gln Gly Thr Leu Val Thr Val
    450                 455                 460
```

```
Lys Pro Gly Gly Gly Ser Gly Val Gln Val Glu Thr Ile Ser Pro
465                 470                 475                 480

Gly Asp Gly Arg Thr Phe Pro Lys Arg Gly Gln Thr Cys Val Val His
            485                 490                 495

Tyr Thr Gly Met Leu Glu Asp Gly Lys Lys Phe Asp Ser Ser Arg Asp
        500                 505                 510

Arg Asn Lys Pro Phe Lys Phe Met Leu Gly Lys Gln Glu Val Ile Arg
    515                 520                 525

Gly Trp Glu Glu Gly Val Ala Gln Met Ser Val Gly Gln Arg Ala Lys
530                 535                 540

Leu Thr Ile Ser Pro Asp Tyr Ala Tyr Gly Ala Thr Gly His Pro Gly
545                 550                 555                 560

Ile Ile Pro Pro His Ala Thr Leu Val Phe Asp Val Glu Leu Leu Lys
            565                 570                 575

Leu Glu Gly Gly Arg Met Ala Leu Ile Val Leu Gly Val Ala Gly
        580                 585                 590

Leu Leu Leu Phe Ile Gly Leu Gly Ile Phe Phe Ala Leu Tyr Leu Leu
        595                 600                 605

Arg Arg Asp Gln Arg Leu Pro Pro Asp Ala His Lys Pro Pro Gly Gly
610                 615                 620

Gly Ser Phe Arg Thr Pro Ile Gln Glu Glu Gln Ala Asp Ala His Ser
625                 630                 635                 640

Thr Leu Ala Lys Ile
            645
```

<210> SEQ ID NO 28
<211> LENGTH: 653
<212> TYPE: PRT
<213> ORGANISM: Artificial Sequence
<220> FEATURE:
<223> OTHER INFORMATION: Made in Lab - anti-CLL1 DARIC.OX40 fusion
      protein

<400> SEQUENCE: 28

```
Met Ala Leu Pro Val Thr Ala Leu Leu Leu Pro Leu Ala Leu Leu Leu
1               5                   10                  15

His Ala Ala Arg Pro Gly Ser Ile Leu Trp His Glu Met Trp His Glu
                20                  25                  30

Gly Leu Glu Glu Ala Ser Arg Leu Tyr Phe Gly Glu Arg Asn Val Lys
            35                  40                  45

Gly Met Phe Glu Val Leu Glu Pro Leu His Ala Met Met Glu Arg Gly
        50                  55                  60

Pro Gln Thr Leu Lys Glu Thr Ser Phe Asn Gln Ala Tyr Gly Arg Asp
65                  70                  75                  80

Leu Met Glu Ala Gln Glu Trp Cys Arg Lys Tyr Met Lys Ser Gly Asn
                85                  90                  95

Val Lys Asp Leu Leu Gln Ala Trp Asp Leu Tyr Tyr His Val Phe Arg
            100                 105                 110

Arg Ile Ser Lys Ala Ser Ala Gly Thr Gly Ser Asp Ile Tyr Ile Trp
        115                 120                 125

Ala Pro Leu Ala Gly Thr Cys Gly Val Leu Leu Leu Ser Leu Val Ile
    130                 135                 140

Thr Met His Lys Arg Gly Arg Lys Lys Leu Leu Tyr Ile Phe Lys Gln
145                 150                 155                 160

Pro Phe Met Arg Pro Val Gln Thr Thr Gln Glu Glu Asp Gly Cys Ser
                165                 170                 175
```

```
Cys Arg Phe Pro Glu Glu Glu Gly Gly Cys Glu Leu Arg Val Lys
            180                 185                 190

Phe Ser Arg Ser Ala Asp Ala Pro Ala Tyr Gln Gln Gly Gln Asn Gln
            195                 200                 205

Leu Tyr Asn Glu Leu Asn Leu Gly Arg Arg Glu Tyr Asp Val Leu
210                 215                 220

Asp Lys Arg Arg Gly Arg Asp Pro Glu Met Gly Gly Lys Pro Arg Arg
225                 230                 235                 240

Lys Asn Pro Gln Glu Gly Leu Tyr Asn Glu Leu Gln Lys Asp Lys Met
                245                 250                 255

Ala Glu Ala Tyr Ser Glu Ile Gly Met Lys Gly Glu Arg Arg Arg Gly
            260                 265                 270

Lys Gly His Asp Gly Leu Tyr Gln Gly Leu Ser Thr Ala Thr Lys Asp
            275                 280                 285

Thr Tyr Asp Ala Leu His Met Gln Ala Leu Pro Pro Arg Ser Gly Ser
            290                 295                 300

Gly Ala Thr Asn Phe Ser Leu Leu Lys Gln Ala Gly Asp Val Glu Glu
305                 310                 315                 320

Asn Pro Gly Pro Ser Met Glu Thr Asp Thr Leu Leu Leu Trp Val Leu
                325                 330                 335

Leu Leu Trp Val Pro Gly Ser Thr Gly Glu Val Gln Leu Val Glu Ser
            340                 345                 350

Gly Gly Gly Glu Val Gln Pro Gly Gly Ser Leu Arg Leu Ser Cys Ala
            355                 360                 365

Ala Ser Gly Phe Thr Phe Asp Asp Tyr Ala Ile Gly Trp Phe Arg Gln
            370                 375                 380

Ala Pro Gly Lys Glu Arg Glu Gly Val Ser Thr Ile Ser Ser Ser Asp
385                 390                 395                 400

Gly Ser Thr Tyr Tyr Ala Glu Ser Val Lys Gly Arg Phe Thr Ile Ser
                405                 410                 415

Arg Asp Asn Ala Lys Asn Thr Val Tyr Leu Gln Met Ser Ser Leu Arg
                420                 425                 430

Ala Glu Asp Thr Ala Val Tyr Tyr Cys Ala Leu Arg Glu Gly Leu Pro
            435                 440                 445

Leu Leu Leu Asp Thr Leu Trp Arg Gln Pro Val Glu Tyr Asp Tyr Trp
450                 455                 460

Gly Gln Gly Thr Gln Val Thr Val Lys Pro Gly Gly Gly Ser Gly
465                 470                 475                 480

Val Gln Val Glu Thr Ile Ser Pro Gly Asp Gly Arg Thr Phe Pro Lys
                485                 490                 495

Arg Gly Gln Thr Cys Val Val His Tyr Thr Gly Met Leu Glu Asp Gly
            500                 505                 510

Lys Lys Phe Asp Ser Ser Arg Asp Arg Asn Lys Pro Phe Lys Phe Met
            515                 520                 525

Leu Gly Lys Gln Glu Val Ile Arg Gly Trp Glu Glu Gly Val Ala Gln
            530                 535                 540

Met Ser Val Gly Gln Arg Ala Lys Leu Thr Ile Ser Pro Asp Tyr Ala
545                 550                 555                 560

Tyr Gly Ala Thr Gly His Pro Gly Ile Ile Pro Pro His Ala Thr Leu
                565                 570                 575

Val Phe Asp Val Glu Leu Leu Lys Leu Glu Gly Arg Met Ala Leu
            580                 585                 590
```

Ile Val Leu Gly Gly Val Ala Gly Leu Leu Phe Ile Gly Leu Gly
                595                 600                 605

Ile Phe Phe Ala Leu Tyr Leu Leu Arg Arg Asp Gln Arg Leu Pro Pro
    610                 615                 620

Asp Ala His Lys Pro Pro Gly Gly Ser Phe Arg Thr Pro Ile Gln
625                 630                 635                 640

Glu Glu Gln Ala Asp Ala His Ser Thr Leu Ala Lys Ile
                645                 650

```
<210> SEQ ID NO 29
<211> LENGTH: 640
<212> TYPE: PRT
<213> ORGANISM: Artificial Sequence
<220> FEATURE:
<223> OTHER INFORMATION: Made in Lab - anti-CLL1 DARIC.OX40 fusion
      protein

<400> SEQUENCE: 29
```

Met Ala Leu Pro Val Thr Ala Leu Leu Leu Pro Leu Ala Leu Leu Leu
1               5                   10                  15

His Ala Ala Arg Pro Gly Ser Ile Leu Trp His Glu Met Trp His Glu
                20                  25                  30

Gly Leu Glu Glu Ala Ser Arg Leu Tyr Phe Gly Glu Arg Asn Val Lys
            35                  40                  45

Gly Met Phe Glu Val Leu Glu Pro Leu His Ala Met Met Glu Arg Gly
        50                  55                  60

Pro Gln Thr Leu Lys Glu Thr Ser Phe Asn Gln Ala Tyr Gly Arg Asp
65                  70                  75                  80

Leu Met Glu Ala Gln Glu Trp Cys Arg Lys Tyr Met Lys Ser Gly Asn
                85                  90                  95

Val Lys Asp Leu Leu Gln Ala Trp Asp Leu Tyr Tyr His Val Phe Arg
            100                 105                 110

Arg Ile Ser Lys Ala Ser Ala Gly Thr Gly Ser Asp Ile Tyr Ile Trp
        115                 120                 125

Ala Pro Leu Ala Gly Thr Cys Gly Val Leu Leu Leu Ser Leu Val Ile
130                 135                 140

Thr Met His Lys Arg Gly Arg Lys Lys Leu Leu Tyr Ile Phe Lys Gln
145                 150                 155                 160

Pro Phe Met Arg Pro Val Gln Thr Thr Gln Glu Glu Asp Gly Cys Ser
                165                 170                 175

Cys Arg Phe Pro Glu Glu Glu Glu Gly Gly Cys Glu Leu Arg Val Lys
            180                 185                 190

Phe Ser Arg Ser Ala Asp Ala Pro Ala Tyr Gln Gln Gly Gln Asn Gln
        195                 200                 205

Leu Tyr Asn Glu Leu Asn Leu Gly Arg Arg Glu Glu Tyr Asp Val Leu
210                 215                 220

Asp Lys Arg Arg Gly Arg Asp Pro Glu Met Gly Gly Lys Pro Arg Arg
225                 230                 235                 240

Lys Asn Pro Gln Glu Gly Leu Tyr Asn Glu Leu Gln Lys Asp Lys Met
                245                 250                 255

Ala Glu Ala Tyr Ser Glu Ile Gly Met Lys Gly Glu Arg Arg Arg Gly
            260                 265                 270

Lys Gly His Asp Gly Leu Tyr Gln Gly Leu Ser Thr Ala Thr Lys Asp
        275                 280                 285

Thr Tyr Asp Ala Leu His Met Gln Ala Leu Pro Pro Arg Ser Gly Ser
    290                 295                 300

Gly Ala Thr Asn Phe Ser Leu Leu Lys Gln Ala Gly Asp Val Glu Glu
305                 310                 315                 320

Asn Pro Gly Pro Ser Met Glu Thr Asp Thr Leu Leu Leu Trp Val Leu
            325                 330                 335

Leu Leu Trp Val Pro Gly Ser Thr Gly Glu Val Gln Leu Val Glu Ser
        340                 345                 350

Gly Gly Gly Glu Val Gln Pro Gly Gly Ser Leu Arg Leu Ser Cys Ala
        355                 360                 365

Ala Ser Gly Leu Leu Phe Ser Ile Tyr Asp Met Asn Trp Tyr Arg Gln
    370                 375                 380

Ala Pro Gly Lys Glu Arg Glu Trp Val Ala Gly Ile Thr Asn Asn Gly
385                 390                 395                 400

Tyr Ser Thr Ala Tyr Ala Glu Ser Val Lys Gly Arg Phe Thr Ile Ser
                405                 410                 415

Arg Asp Asn Ala Lys Asn Thr Val Tyr Leu Gln Met Ser Ser Leu Arg
            420                 425                 430

Ala Glu Asp Thr Ala Val Tyr Tyr Cys His Thr Asp Glu Trp Gly Arg
        435                 440                 445

Glu Tyr Trp Gly Gln Gly Thr Leu Val Thr Val Lys Pro Gly Gly Gly
    450                 455                 460

Gly Ser Gly Val Gln Val Glu Thr Ile Ser Pro Gly Asp Gly Arg Thr
465                 470                 475                 480

Phe Pro Lys Arg Gly Gln Thr Cys Val Val His Tyr Thr Gly Met Leu
                485                 490                 495

Glu Asp Gly Lys Lys Phe Asp Ser Ser Arg Asp Arg Asn Lys Pro Phe
            500                 505                 510

Lys Phe Met Leu Gly Lys Gln Glu Val Ile Arg Gly Trp Glu Glu Gly
        515                 520                 525

Val Ala Gln Met Ser Val Gly Gln Arg Ala Lys Leu Thr Ile Ser Pro
    530                 535                 540

Asp Tyr Ala Tyr Gly Ala Thr Gly His Pro Gly Ile Ile Pro Pro His
545                 550                 555                 560

Ala Thr Leu Val Phe Asp Val Glu Leu Leu Lys Leu Glu Gly Gly Arg
                565                 570                 575

Met Ala Leu Ile Val Leu Gly Gly Val Ala Gly Leu Leu Leu Phe Ile
            580                 585                 590

Gly Leu Gly Ile Phe Phe Ala Leu Tyr Leu Leu Arg Arg Asp Gln Arg
        595                 600                 605

Leu Pro Pro Asp Ala His Lys Pro Pro Gly Gly Gly Ser Phe Arg Thr
    610                 615                 620

Pro Ile Gln Glu Glu Gln Ala Asp Ala His Ser Thr Leu Ala Lys Ile
625                 630                 635                 640

<210> SEQ ID NO 30
<211> LENGTH: 636
<212> TYPE: PRT
<213> ORGANISM: Artificial Sequence
<220> FEATURE:
<223> OTHER INFORMATION: Made in Lab - anti-CLL1 DARIC.OX40 fusion
      protein

<400> SEQUENCE: 30

Met Ala Leu Pro Val Thr Ala Leu Leu Leu Pro Leu Ala Leu Leu Leu
1               5                   10                  15

His Ala Ala Arg Pro Gly Ser Ile Leu Trp His Glu Met Trp His Glu

```
            20                  25                  30
Gly Leu Glu Glu Ala Ser Arg Leu Tyr Phe Gly Glu Arg Asn Val Lys
            35                  40                  45
Gly Met Phe Glu Val Leu Glu Pro Leu His Ala Met Met Glu Arg Gly
        50                  55                  60
Pro Gln Thr Leu Lys Glu Thr Ser Phe Asn Gln Ala Tyr Gly Arg Asp
 65                  70                  75                  80
Leu Met Glu Ala Gln Glu Trp Cys Arg Lys Tyr Met Lys Ser Gly Asn
                85                  90                  95
Val Lys Asp Leu Leu Gln Ala Trp Asp Leu Tyr Tyr His Val Phe Arg
            100                 105                 110
Arg Ile Ser Lys Ala Ser Ala Gly Thr Gly Ser Asp Ile Tyr Ile Trp
            115                 120                 125
Ala Pro Leu Ala Gly Thr Cys Gly Val Leu Leu Ser Leu Val Ile
            130                 135                 140
Thr Met His Lys Arg Gly Arg Lys Lys Leu Leu Tyr Ile Phe Lys Gln
 145                 150                 155                 160
Pro Phe Met Arg Pro Val Gln Thr Thr Gln Glu Glu Asp Gly Cys Ser
                165                 170                 175
Cys Arg Phe Pro Glu Glu Glu Gly Gly Cys Glu Leu Arg Val Lys
            180                 185                 190
Phe Ser Arg Ser Ala Asp Ala Pro Ala Tyr Gln Gln Gly Gln Asn Gln
            195                 200                 205
Leu Tyr Asn Glu Leu Asn Leu Gly Arg Arg Glu Glu Tyr Asp Val Leu
            210                 215                 220
Asp Lys Arg Arg Gly Arg Asp Pro Glu Met Gly Gly Lys Pro Arg Arg
 225                 230                 235                 240
Lys Asn Pro Gln Glu Gly Leu Tyr Asn Glu Leu Gln Lys Asp Lys Met
                245                 250                 255
Ala Glu Ala Tyr Ser Glu Ile Gly Met Lys Gly Glu Arg Arg Arg Gly
            260                 265                 270
Lys Gly His Asp Gly Leu Tyr Gln Gly Leu Ser Thr Ala Thr Lys Asp
            275                 280                 285
Thr Tyr Asp Ala Leu His Met Gln Ala Leu Pro Pro Arg Ser Gly Ser
 290                 295                 300
Gly Ala Thr Asn Phe Ser Leu Leu Lys Gln Ala Gly Asp Val Glu Glu
 305                 310                 315                 320
Asn Pro Gly Pro Ser Met Glu Thr Asp Thr Leu Leu Leu Trp Val Leu
                325                 330                 335
Leu Leu Trp Val Pro Gly Ser Thr Gly Glu Val Gln Leu Val Glu Ser
            340                 345                 350
Gly Gly Gly Glu Val Gln Pro Gly Gly Ser Leu Arg Leu Ser Cys Ala
            355                 360                 365
Ala Ser Gly Arg Thr Phe Glu Tyr Asp Asp Met Val Trp Phe Arg Gln
            370                 375                 380
Ala Pro Gly Lys Glu Arg Glu Val Ala Gly Ile Ser Trp Ser Gly
 385                 390                 395                 400
Gly Ser Ile Tyr Tyr Ala Glu Ser Val Lys Gly Arg Phe Ser Ile Ser
                405                 410                 415
Arg Asp Asn Ala Lys Asn Thr Val Tyr Leu Glu Met Asn Arg Leu Lys
            420                 425                 430
Pro Glu Asp Thr Ala Val Tyr Tyr Cys Asn Val Gly Ser Tyr Trp Gly
            435                 440                 445
```

-continued

Gln Gly Thr Leu Val Thr Val Lys Pro Gly Gly Gly Ser Gly Val
    450                 455                 460

Gln Val Glu Thr Ile Ser Pro Gly Asp Gly Arg Thr Phe Pro Lys Arg
465                 470                 475                 480

Gly Gln Thr Cys Val Val His Tyr Thr Gly Met Leu Glu Asp Gly Lys
                485                 490                 495

Lys Phe Asp Ser Ser Arg Asp Arg Asn Lys Pro Phe Lys Phe Met Leu
                500                 505                 510

Gly Lys Gln Glu Val Ile Arg Gly Trp Glu Glu Gly Val Ala Gln Met
            515                 520                 525

Ser Val Gly Gln Arg Ala Lys Leu Thr Ile Ser Pro Asp Tyr Ala Tyr
            530                 535                 540

Gly Ala Thr Gly His Pro Gly Ile Ile Pro Pro His Ala Thr Leu Val
545                 550                 555                 560

Phe Asp Val Glu Leu Leu Lys Leu Glu Gly Gly Arg Met Ala Leu Ile
                565                 570                 575

Val Leu Gly Gly Val Ala Gly Leu Leu Leu Phe Ile Gly Leu Gly Ile
            580                 585                 590

Phe Phe Ala Leu Tyr Leu Leu Arg Arg Asp Gln Arg Leu Pro Pro Asp
            595                 600                 605

Ala His Lys Pro Pro Gly Gly Gly Ser Phe Arg Thr Pro Ile Gln Glu
        610                 615                 620

Glu Gln Ala Asp Ala His Ser Thr Leu Ala Lys Ile
625                 630                 635

<210> SEQ ID NO 31
<211> LENGTH: 643
<212> TYPE: PRT
<213> ORGANISM: Artificial Sequence
<220> FEATURE:
<223> OTHER INFORMATION: Made in Lab - anti-CLL1 DARIC.OX40 fusion
      protein

<400> SEQUENCE: 31

Met Ala Leu Pro Val Thr Ala Leu Leu Leu Pro Leu Ala Leu Leu Leu
1               5                   10                  15

His Ala Ala Arg Pro Gly Ser Ile Leu Trp His Glu Met Trp His Glu
            20                  25                  30

Gly Leu Glu Glu Ala Ser Arg Leu Tyr Phe Gly Glu Arg Asn Val Lys
        35                  40                  45

Gly Met Phe Glu Val Leu Glu Pro Leu His Ala Met Met Glu Arg Gly
    50                  55                  60

Pro Gln Thr Leu Lys Glu Thr Ser Phe Asn Gln Ala Tyr Gly Arg Asp
65                  70                  75                  80

Leu Met Glu Ala Gln Glu Trp Cys Arg Lys Tyr Met Lys Ser Gly Asn
                85                  90                  95

Val Lys Asp Leu Leu Gln Ala Trp Asp Leu Tyr Tyr His Val Phe Arg
            100                 105                 110

Arg Ile Ser Lys Ala Ser Ala Gly Thr Gly Ser Asp Ile Tyr Ile Trp
        115                 120                 125

Ala Pro Leu Ala Gly Thr Cys Gly Val Leu Leu Leu Ser Leu Val Ile
    130                 135                 140

Thr Met His Lys Arg Gly Arg Lys Lys Leu Leu Tyr Ile Phe Lys Gln
145                 150                 155                 160

Pro Phe Met Arg Pro Val Gln Thr Thr Gln Glu Glu Asp Gly Cys Ser

-continued

```
            165                 170                 175
Cys Arg Phe Pro Glu Glu Glu Gly Gly Cys Glu Leu Arg Val Lys
            180                 185                 190
Phe Ser Arg Ser Ala Asp Ala Pro Ala Tyr Gln Gln Gly Gln Asn Gln
            195                 200                 205
Leu Tyr Asn Glu Leu Asn Leu Gly Arg Arg Glu Glu Tyr Asp Val Leu
            210                 215                 220
Asp Lys Arg Arg Gly Arg Asp Pro Glu Met Gly Gly Lys Pro Arg Arg
225                 230                 235                 240
Lys Asn Pro Gln Glu Gly Leu Tyr Asn Glu Leu Gln Lys Asp Lys Met
                    245                 250                 255
Ala Glu Ala Tyr Ser Glu Ile Gly Met Lys Gly Glu Arg Arg Arg Gly
            260                 265                 270
Lys Gly His Asp Gly Leu Tyr Gln Gly Leu Ser Thr Ala Thr Lys Asp
            275                 280                 285
Thr Tyr Asp Ala Leu His Met Gln Ala Leu Pro Pro Arg Ser Gly Ser
            290                 295                 300
Gly Ala Thr Asn Phe Ser Leu Leu Lys Gln Ala Gly Asp Val Glu Glu
305                 310                 315                 320
Asn Pro Gly Pro Ser Met Glu Thr Asp Thr Leu Leu Leu Trp Val Leu
                    325                 330                 335
Leu Leu Trp Val Pro Gly Ser Thr Gly Glu Val Gln Leu Val Glu Ser
            340                 345                 350
Gly Gly Gly Glu Val Gln Pro Gly Gly Ser Leu Arg Leu Ser Cys Ala
            355                 360                 365
Ala Ser Gly Phe Thr Phe Arg Ile Asn Asp Met Gly Trp Tyr Arg Gln
370                 375                 380
Ala Pro Gly Lys Glu Cys Glu Met Val Ala Gly Ile Ser Asn Asn Gly
385                 390                 395                 400
Phe Ser Thr Ala Tyr Ala Glu Ser Val Lys Gly Arg Phe Thr Ile Ser
                    405                 410                 415
Arg Asp Asn Ala Lys Asn Thr Val Tyr Leu Gln Met Ser Ser Leu Arg
                    420                 425                 430
Ala Glu Asp Thr Ala Val Tyr Tyr Cys His Arg Thr Asp Glu Gly Ala
            435                 440                 445
Ala His Ala Cys Ser Arg Gly Gln Gly Thr Leu Val Thr Val Lys Pro
450                 455                 460
Gly Gly Gly Gly Ser Gly Val Gln Val Glu Thr Ile Ser Pro Gly Asp
465                 470                 475                 480
Gly Arg Thr Phe Pro Lys Arg Gly Gln Thr Cys Val Val His Tyr Thr
                    485                 490                 495
Gly Met Leu Glu Asp Gly Lys Lys Phe Asp Ser Ser Arg Asp Arg Asn
                    500                 505                 510
Lys Pro Phe Lys Phe Met Leu Gly Lys Gln Glu Val Ile Arg Gly Trp
            515                 520                 525
Glu Glu Gly Val Ala Gln Met Ser Val Gly Gln Arg Ala Lys Leu Thr
            530                 535                 540
Ile Ser Pro Asp Tyr Ala Tyr Gly Ala Thr Gly His Pro Gly Ile Ile
545                 550                 555                 560
Pro Pro His Ala Thr Leu Val Phe Asp Val Glu Leu Leu Lys Leu Glu
                    565                 570                 575
Gly Gly Arg Met Ala Leu Ile Val Leu Gly Gly Val Ala Gly Leu Leu
            580                 585                 590
```

```
Leu Phe Ile Gly Leu Gly Ile Phe Ala Leu Tyr Leu Arg Arg
        595                 600                 605

Asp Gln Arg Leu Pro Pro Asp Ala His Lys Pro Pro Gly Gly Gly Ser
610                 615                 620

Phe Arg Thr Pro Ile Gln Glu Glu Gln Ala Asp Ala His Ser Thr Leu
625                 630                 635                 640

Ala Lys Ile

<210> SEQ ID NO 32
<211> LENGTH: 776
<212> TYPE: PRT
<213> ORGANISM: Artificial Sequence
<220> FEATURE:
<223> OTHER INFORMATION: Made in Lab - anti-CLL1 DARIC.TNRF2 fusion
      protein

<400> SEQUENCE: 32

Met Ala Leu Pro Val Thr Ala Leu Leu Pro Leu Ala Leu Leu Leu
1               5                   10                  15

His Ala Ala Arg Pro Gly Ser Ile Leu Trp His Glu Met Trp His Glu
                20                  25                  30

Gly Leu Glu Glu Ala Ser Arg Leu Tyr Phe Gly Glu Arg Asn Val Lys
            35                  40                  45

Gly Met Phe Glu Val Leu Glu Pro Leu His Ala Met Met Glu Arg Gly
50                  55                  60

Pro Gln Thr Leu Lys Glu Thr Ser Phe Asn Gln Ala Tyr Gly Arg Asp
65                  70                  75                  80

Leu Met Glu Ala Gln Glu Trp Cys Arg Lys Tyr Met Lys Ser Gly Asn
                85                  90                  95

Val Lys Asp Leu Leu Gln Ala Trp Asp Leu Tyr Tyr His Val Phe Arg
            100                 105                 110

Arg Ile Ser Lys Ala Ser Ala Gly Thr Gly Ser Asp Ile Tyr Ile Trp
        115                 120                 125

Ala Pro Leu Ala Gly Thr Cys Gly Val Leu Leu Leu Ser Leu Val Ile
    130                 135                 140

Thr Met His Lys Arg Gly Arg Lys Lys Leu Leu Tyr Ile Phe Lys Gln
145                 150                 155                 160

Pro Phe Met Arg Pro Val Gln Thr Thr Gln Glu Glu Asp Gly Cys Ser
                165                 170                 175

Cys Arg Phe Pro Glu Glu Glu Glu Gly Gly Cys Glu Leu Arg Val Lys
            180                 185                 190

Phe Ser Arg Ser Ala Asp Ala Pro Ala Tyr Gln Gln Gly Gln Asn Gln
        195                 200                 205

Leu Tyr Asn Glu Leu Asn Leu Gly Arg Arg Glu Glu Tyr Asp Val Leu
    210                 215                 220

Asp Lys Arg Arg Gly Arg Asp Pro Glu Met Gly Gly Lys Pro Arg Arg
225                 230                 235                 240

Lys Asn Pro Gln Glu Gly Leu Tyr Asn Glu Leu Gln Lys Asp Lys Met
                245                 250                 255

Ala Glu Ala Tyr Ser Glu Ile Gly Met Lys Gly Glu Arg Arg Arg Gly
            260                 265                 270

Lys Gly His Asp Gly Leu Tyr Gln Gly Leu Ser Thr Ala Thr Lys Asp
        275                 280                 285

Thr Tyr Asp Ala Leu His Met Gln Ala Leu Pro Pro Arg Ser Gly Ser
    290                 295                 300
```

```
Gly Ala Thr Asn Phe Ser Leu Leu Lys Gln Ala Gly Asp Val Glu Glu
305                 310                 315                 320

Asn Pro Gly Pro Ser Met Glu Thr Asp Thr Leu Leu Leu Trp Val Leu
            325                 330                 335

Leu Leu Trp Val Pro Gly Ser Thr Gly Glu Val Gln Leu Val Glu Ser
        340                 345                 350

Gly Gly Gly Glu Val Gln Pro Gly Gly Ser Leu Arg Leu Ser Cys Ala
            355                 360                 365

Ala Ser Gly Phe Leu Phe Ser Ile Tyr Asp Met Asn Trp Tyr Arg Gln
370                 375                 380

Ala Pro Gly Lys Glu Arg Glu Trp Val Ala Gly Ile Thr Asn Asn Gly
385                 390                 395                 400

Tyr Ser Thr Ala Tyr Ala Glu Ser Val Lys Gly Arg Phe Thr Ile Ser
                405                 410                 415

Arg Asp Asn Ala Lys Asn Thr Ile Tyr Leu Gln Met Ser Ser Leu Arg
            420                 425                 430

Ala Glu Asp Thr Ala Val Tyr Tyr Cys His Ala Asp Leu Thr Lys Ala
        435                 440                 445

Tyr Asp Val Glu Tyr Ala Trp Gly Gln Gly Thr Leu Val Thr Val Lys
450                 455                 460

Pro Gly Gly Gly Ser Gly Val Gln Val Glu Thr Ile Ser Pro Gly
465                 470                 475                 480

Asp Gly Arg Thr Phe Pro Lys Arg Gly Gln Thr Cys Val Val His Tyr
                485                 490                 495

Thr Gly Met Leu Glu Asp Gly Lys Lys Phe Asp Ser Ser Arg Asp Arg
            500                 505                 510

Asn Lys Pro Phe Lys Phe Met Leu Gly Lys Gln Glu Val Ile Arg Gly
        515                 520                 525

Trp Glu Glu Gly Val Ala Gln Met Ser Val Gly Gln Arg Ala Lys Leu
530                 535                 540

Thr Ile Ser Pro Asp Tyr Ala Tyr Gly Ala Thr Gly His Pro Gly Ile
545                 550                 555                 560

Ile Pro Pro His Ala Thr Leu Val Phe Asp Val Glu Leu Leu Lys Leu
                565                 570                 575

Glu Gly Gly Arg Met Ala Leu Ile Val Leu Gly Gly Val Ala Gly Leu
            580                 585                 590

Leu Leu Phe Ile Gly Leu Gly Ile Phe Phe Lys Lys Pro Leu Cys
        595                 600                 605

Leu Gln Arg Glu Ala Lys Val Pro His Leu Pro Ala Asp Lys Ala Arg
610                 615                 620

Gly Thr Gln Gly Pro Glu Gln Gln His Leu Leu Ile Thr Ala Pro Ser
625                 630                 635                 640

Ser Ser Ser Ser Ser Leu Glu Ser Ser Ala Ser Ala Leu Asp Arg Arg
                645                 650                 655

Ala Pro Thr Arg Asn Gln Pro Gln Ala Pro Gly Val Glu Ala Ser Gly
            660                 665                 670

Ala Gly Glu Ala Arg Ala Ser Thr Gly Ser Ser Asp Ser Ser Pro Gly
        675                 680                 685

Gly His Gly Thr Gln Val Asn Val Thr Cys Ile Val Asn Val Cys Ser
690                 695                 700

Ser Ser Asp His Ser Ser Gln Cys Ser Ser Gln Ala Ser Ser Thr Met
705                 710                 715                 720
```

```
Gly Asp Thr Asp Ser Ser Pro Ser Glu Ser Pro Lys Asp Glu Gln Val
                725                 730                 735

Pro Phe Ser Lys Glu Glu Cys Ala Phe Arg Ser Gln Leu Glu Thr Pro
            740                 745                 750

Glu Thr Leu Leu Gly Ser Thr Glu Glu Lys Pro Leu Pro Leu Gly Val
        755                 760                 765

Pro Asp Ala Gly Met Lys Pro Ser
    770                 775

<210> SEQ ID NO 33
<211> LENGTH: 777
<212> TYPE: PRT
<213> ORGANISM: Artificial Sequence
<220> FEATURE:
<223> OTHER INFORMATION: Made in Lab - anti-CLL1 DARIC.TNRF2 fusion
      protein

<400> SEQUENCE: 33

Met Ala Leu Pro Val Thr Ala Leu Leu Leu Pro Leu Ala Leu Leu Leu
1               5                   10                  15

His Ala Ala Arg Pro Gly Ser Ile Leu Trp His Glu Met Trp His Glu
            20                  25                  30

Gly Leu Glu Glu Ala Ser Arg Leu Tyr Phe Gly Glu Arg Asn Val Lys
        35                  40                  45

Gly Met Phe Glu Val Leu Glu Pro Leu His Ala Met Met Glu Arg Gly
    50                  55                  60

Pro Gln Thr Leu Lys Glu Thr Ser Phe Asn Gln Ala Tyr Gly Arg Asp
65                  70                  75                  80

Leu Met Glu Ala Gln Glu Trp Cys Arg Lys Tyr Met Lys Ser Gly Asn
                85                  90                  95

Val Lys Asp Leu Leu Gln Ala Trp Asp Leu Tyr Tyr His Val Phe Arg
            100                 105                 110

Arg Ile Ser Lys Ala Ser Ala Gly Thr Gly Ser Asp Ile Tyr Ile Trp
        115                 120                 125

Ala Pro Leu Ala Gly Thr Cys Gly Val Leu Leu Leu Ser Leu Val Ile
    130                 135                 140

Thr Met His Lys Arg Gly Arg Lys Lys Leu Leu Tyr Ile Phe Lys Gln
145                 150                 155                 160

Pro Phe Met Arg Pro Val Gln Thr Thr Gln Glu Glu Asp Gly Cys Ser
                165                 170                 175

Cys Arg Phe Pro Glu Glu Glu Glu Gly Gly Cys Glu Leu Arg Val Lys
            180                 185                 190

Phe Ser Arg Ser Ala Asp Ala Pro Ala Tyr Gln Gln Gly Gln Asn Gln
        195                 200                 205

Leu Tyr Asn Glu Leu Asn Leu Gly Arg Arg Glu Glu Tyr Asp Val Leu
    210                 215                 220

Asp Lys Arg Arg Gly Arg Asp Pro Glu Met Gly Gly Lys Pro Arg Arg
225                 230                 235                 240

Lys Asn Pro Gln Glu Gly Leu Tyr Asn Glu Leu Gln Lys Asp Lys Met
                245                 250                 255

Ala Glu Ala Tyr Ser Glu Ile Gly Met Lys Gly Glu Arg Arg Arg Gly
            260                 265                 270

Lys Gly His Asp Gly Leu Tyr Gln Gly Leu Ser Thr Ala Thr Lys Asp
        275                 280                 285

Thr Tyr Asp Ala Leu His Met Gln Ala Leu Pro Pro Arg Ser Gly Ser
    290                 295                 300
```

```
Gly Ala Thr Asn Phe Ser Leu Leu Lys Gln Ala Gly Asp Val Glu Glu
305                 310                 315                 320

Asn Pro Gly Pro Ser Met Glu Thr Asp Thr Leu Leu Leu Trp Val Leu
            325                 330                 335

Leu Leu Trp Val Pro Gly Ser Thr Gly Glu Val Gln Leu Val Glu Ser
            340                 345                 350

Gly Gly Gly Glu Val Gln Pro Gly Gly Ser Leu Arg Leu Ser Cys Ala
            355                 360                 365

Ala Ser Gly Phe Thr Phe Ser Val Tyr Asp Met Asn Trp Tyr Arg Gln
            370                 375                 380

Ala Pro Gly Lys Glu Arg Glu Trp Val Ser Gly Ile Ser Asn Asn Gly
385                 390                 395                 400

Phe Ser Thr Ala Tyr Ala Glu Ser Val Lys Gly Arg Phe Thr Ile Ser
                405                 410                 415

Arg Asp Asn Ala Lys Asn Thr Leu Tyr Leu Gln Met Ser Ser Leu Arg
                420                 425                 430

Ala Glu Asp Thr Ala Val Tyr Tyr Cys Asn Leu Asp Val His Gly Arg
            435                 440                 445

Val Gly Ala Gln Gly Asp Tyr Trp Gly Gln Gly Thr Leu Val Thr Val
            450                 455                 460

Lys Pro Gly Gly Gly Ser Gly Val Gln Val Glu Thr Ile Ser Pro
465                 470                 475                 480

Gly Asp Gly Arg Thr Phe Pro Lys Arg Gly Gln Thr Cys Val Val His
                485                 490                 495

Tyr Thr Gly Met Leu Glu Asp Gly Lys Lys Phe Asp Ser Ser Arg Asp
                500                 505                 510

Arg Asn Lys Pro Phe Lys Phe Met Leu Gly Lys Gln Glu Val Ile Arg
            515                 520                 525

Gly Trp Glu Glu Gly Val Ala Gln Met Ser Val Gly Gln Arg Ala Lys
            530                 535                 540

Leu Thr Ile Ser Pro Asp Tyr Ala Tyr Gly Ala Thr Gly His Pro Gly
545                 550                 555                 560

Ile Ile Pro Pro His Ala Thr Leu Val Phe Asp Val Glu Leu Leu Lys
                565                 570                 575

Leu Glu Gly Gly Arg Met Ala Leu Ile Val Leu Gly Gly Val Ala Gly
            580                 585                 590

Leu Leu Leu Phe Ile Gly Leu Gly Ile Phe Phe Lys Lys Lys Pro Leu
            595                 600                 605

Cys Leu Gln Arg Glu Ala Lys Val Pro His Leu Pro Ala Asp Lys Ala
            610                 615                 620

Arg Gly Thr Gln Gly Pro Glu Gln Gln His Leu Leu Ile Thr Ala Pro
625                 630                 635                 640

Ser Ser Ser Ser Ser Leu Glu Ser Ala Ser Ala Leu Asp Arg
                645                 650                 655

Arg Ala Pro Thr Arg Asn Gln Pro Gln Ala Pro Gly Val Glu Ala Ser
                660                 665                 670

Gly Ala Gly Glu Ala Arg Ala Ser Thr Gly Ser Ser Asp Ser Ser Pro
            675                 680                 685

Gly Gly His Gly Thr Gln Val Asn Val Thr Cys Ile Val Asn Val Cys
            690                 695                 700

Ser Ser Ser Asp His Ser Ser Gln Cys Ser Ser Gln Ala Ser Ser Thr
705                 710                 715                 720
```

```
Met Gly Asp Thr Asp Ser Ser Pro Ser Glu Ser Pro Lys Asp Glu Gln
                725                 730                 735

Val Pro Phe Ser Lys Glu Glu Cys Ala Phe Arg Ser Gln Leu Glu Thr
                740                 745                 750

Pro Glu Thr Leu Leu Gly Ser Thr Glu Glu Lys Pro Leu Pro Leu Gly
                755                 760                 765

Val Pro Asp Ala Gly Met Lys Pro Ser
                770                 775

<210> SEQ ID NO 34
<211> LENGTH: 785
<212> TYPE: PRT
<213> ORGANISM: Artificial Sequence
<220> FEATURE:
<223> OTHER INFORMATION: Made in Lab - anti-CLL1 DARIC.TNRF2 fusion
      protein

<400> SEQUENCE: 34

Met Ala Leu Pro Val Thr Ala Leu Leu Leu Pro Leu Ala Leu Leu Leu
1               5                   10                  15

His Ala Ala Arg Pro Gly Ser Ile Leu Trp His Glu Met Trp His Glu
                20                  25                  30

Gly Leu Glu Glu Ala Ser Arg Leu Tyr Phe Gly Glu Arg Asn Val Lys
                35                  40                  45

Gly Met Phe Glu Val Leu Glu Pro Leu His Ala Met Met Glu Arg Gly
    50                  55                  60

Pro Gln Thr Leu Lys Glu Thr Ser Phe Asn Gln Ala Tyr Gly Arg Asp
65                  70                  75                  80

Leu Met Glu Ala Gln Glu Trp Cys Arg Lys Tyr Met Lys Ser Gly Asn
                85                  90                  95

Val Lys Asp Leu Leu Gln Ala Trp Asp Leu Tyr Tyr His Val Phe Arg
                100                 105                 110

Arg Ile Ser Lys Ala Ser Ala Gly Thr Gly Ser Asp Ile Tyr Ile Trp
                115                 120                 125

Ala Pro Leu Ala Gly Thr Cys Gly Val Leu Leu Leu Ser Leu Val Ile
                130                 135                 140

Thr Met His Lys Arg Gly Arg Lys Lys Leu Leu Tyr Ile Phe Lys Gln
145                 150                 155                 160

Pro Phe Met Arg Pro Val Gln Thr Thr Gln Glu Glu Asp Gly Cys Ser
                165                 170                 175

Cys Arg Phe Pro Glu Glu Glu Glu Gly Gly Cys Glu Leu Arg Val Lys
                180                 185                 190

Phe Ser Arg Ser Ala Asp Ala Pro Ala Tyr Gln Gln Gly Gln Asn Gln
                195                 200                 205

Leu Tyr Asn Glu Leu Asn Leu Gly Arg Arg Glu Glu Tyr Asp Val Leu
                210                 215                 220

Asp Lys Arg Arg Gly Arg Asp Pro Glu Met Gly Gly Lys Pro Arg Arg
225                 230                 235                 240

Lys Asn Pro Gln Glu Gly Leu Tyr Asn Glu Leu Gln Lys Asp Lys Met
                245                 250                 255

Ala Glu Ala Tyr Ser Glu Ile Gly Met Lys Gly Glu Arg Arg Arg Gly
                260                 265                 270

Lys Gly His Asp Gly Leu Tyr Gln Gly Leu Ser Thr Ala Thr Lys Asp
                275                 280                 285

Thr Tyr Asp Ala Leu His Met Gln Ala Leu Pro Pro Arg Ser Gly Ser
                290                 295                 300
```

-continued

```
Gly Ala Thr Asn Phe Ser Leu Leu Lys Gln Ala Gly Asp Val Glu Glu
305                 310                 315                 320

Asn Pro Gly Pro Ser Met Glu Thr Asp Thr Leu Leu Leu Trp Val Leu
            325                 330                 335

Leu Leu Trp Val Pro Gly Ser Thr Gly Glu Val Gln Leu Val Glu Ser
        340                 345                 350

Gly Gly Gly Glu Val Gln Pro Gly Gly Ser Leu Arg Leu Ser Cys Ala
        355                 360                 365

Ala Ser Gly Phe Thr Phe Asp Asp Tyr Ala Ile Gly Trp Phe Arg Gln
370                 375                 380

Ala Pro Gly Lys Glu Arg Glu Gly Val Ser Thr Ile Ser Ser Ser Asp
385                 390                 395                 400

Gly Ser Thr Tyr Tyr Ala Glu Ser Val Lys Gly Arg Phe Thr Ile Ser
            405                 410                 415

Arg Asp Asn Ala Lys Asn Thr Val Tyr Leu Gln Met Ser Ser Leu Arg
                420                 425                 430

Ala Glu Asp Thr Ala Val Tyr Tyr Cys Ala Leu Arg Glu Gly Leu Pro
            435                 440                 445

Leu Leu Leu Asp Thr Leu Trp Arg Gln Pro Val Glu Tyr Asp Tyr Trp
        450                 455                 460

Gly Gln Gly Thr Gln Val Thr Val Lys Pro Gly Gly Gly Ser Gly
465                 470                 475                 480

Val Gln Val Glu Thr Ile Ser Pro Gly Asp Gly Arg Thr Phe Pro Lys
                485                 490                 495

Arg Gly Gln Thr Cys Val Val His Tyr Thr Gly Met Leu Glu Asp Gly
            500                 505                 510

Lys Lys Phe Asp Ser Ser Arg Asp Arg Asn Lys Pro Phe Lys Phe Met
        515                 520                 525

Leu Gly Lys Gln Glu Val Ile Arg Gly Trp Glu Glu Gly Val Ala Gln
    530                 535                 540

Met Ser Val Gly Gln Arg Ala Lys Leu Thr Ile Ser Pro Asp Tyr Ala
545                 550                 555                 560

Tyr Gly Ala Thr Gly His Pro Gly Ile Ile Pro Pro His Ala Thr Leu
                565                 570                 575

Val Phe Asp Val Glu Leu Leu Lys Leu Glu Gly Gly Arg Met Ala Leu
            580                 585                 590

Ile Val Leu Gly Gly Val Ala Gly Leu Leu Leu Phe Ile Gly Leu Gly
        595                 600                 605

Ile Phe Phe Lys Lys Lys Pro Leu Cys Leu Gln Arg Glu Ala Lys Val
    610                 615                 620

Pro His Leu Pro Ala Asp Lys Ala Arg Gly Thr Gln Gly Pro Glu Gln
625                 630                 635                 640

Gln His Leu Leu Ile Thr Ala Pro Ser Ser Ser Ser Ser Ser Leu Glu
                645                 650                 655

Ser Ser Ala Ser Ala Leu Asp Arg Arg Ala Pro Thr Arg Asn Gln Pro
            660                 665                 670

Gln Ala Pro Gly Val Glu Ala Ser Gly Ala Gly Glu Ala Arg Ala Ser
        675                 680                 685

Thr Gly Ser Ser Asp Ser Ser Pro Gly Gly His Gly Thr Gln Val Asn
    690                 695                 700

Val Thr Cys Ile Val Asn Val Cys Ser Ser Ser Asp His Ser Ser Gln
705                 710                 715                 720
```

```
Cys Ser Ser Gln Ala Ser Ser Thr Met Gly Asp Thr Asp Ser Ser Pro
                725                 730                 735

Ser Glu Ser Pro Lys Asp Glu Gln Val Pro Phe Ser Lys Glu Glu Cys
            740                 745                 750

Ala Phe Arg Ser Gln Leu Glu Thr Pro Glu Thr Leu Leu Gly Ser Thr
        755                 760                 765

Glu Glu Lys Pro Leu Pro Leu Gly Val Pro Asp Ala Gly Met Lys Pro
    770                 775                 780

Ser
785

<210> SEQ ID NO 35
<211> LENGTH: 772
<212> TYPE: PRT
<213> ORGANISM: Artificial Sequence
<220> FEATURE:
<223> OTHER INFORMATION: Made in Lab - anti-CLL1 DARIC.TNRF2 fusion
      protein

<400> SEQUENCE: 35

Met Ala Leu Pro Val Thr Ala Leu Leu Leu Pro Leu Ala Leu Leu Leu
1               5                   10                  15

His Ala Ala Arg Pro Gly Ser Ile Leu Trp His Glu Met Trp His Glu
            20                  25                  30

Gly Leu Glu Glu Ala Ser Arg Leu Tyr Phe Gly Glu Arg Asn Val Lys
        35                  40                  45

Gly Met Phe Glu Val Leu Glu Pro Leu His Ala Met Met Glu Arg Gly
    50                  55                  60

Pro Gln Thr Leu Lys Glu Thr Ser Phe Asn Gln Ala Tyr Gly Arg Asp
65                  70                  75                  80

Leu Met Glu Ala Gln Glu Trp Cys Arg Lys Tyr Met Lys Ser Gly Asn
                85                  90                  95

Val Lys Asp Leu Leu Gln Ala Trp Asp Leu Tyr Tyr His Val Phe Arg
            100                 105                 110

Arg Ile Ser Lys Ala Ser Ala Gly Thr Gly Ser Asp Ile Tyr Ile Trp
        115                 120                 125

Ala Pro Leu Ala Gly Thr Cys Gly Val Leu Leu Leu Ser Leu Val Ile
    130                 135                 140

Thr Met His Lys Arg Gly Arg Lys Lys Leu Leu Tyr Ile Phe Lys Gln
145                 150                 155                 160

Pro Phe Met Arg Pro Val Gln Thr Thr Gln Glu Glu Asp Gly Cys Ser
                165                 170                 175

Cys Arg Phe Pro Glu Glu Glu Glu Gly Gly Cys Glu Leu Arg Val Lys
            180                 185                 190

Phe Ser Arg Ser Ala Asp Ala Pro Ala Tyr Gln Gln Gly Gln Asn Gln
        195                 200                 205

Leu Tyr Asn Glu Leu Asn Leu Gly Arg Arg Glu Glu Tyr Asp Val Leu
    210                 215                 220

Asp Lys Arg Arg Gly Arg Asp Pro Glu Met Gly Gly Lys Pro Arg Arg
225                 230                 235                 240

Lys Asn Pro Gln Glu Gly Leu Tyr Asn Glu Leu Gln Lys Asp Lys Met
                245                 250                 255

Ala Glu Ala Tyr Ser Glu Ile Gly Met Lys Gly Glu Arg Arg Arg Gly
            260                 265                 270

Lys Gly His Asp Gly Leu Tyr Gln Gly Leu Ser Thr Ala Thr Lys Asp
        275                 280                 285
```

```
Thr Tyr Asp Ala Leu His Met Gln Ala Leu Pro Pro Arg Ser Gly Ser
    290                 295                 300

Gly Ala Thr Asn Phe Ser Leu Leu Lys Gln Ala Gly Asp Val Glu Glu
305                 310                 315                 320

Asn Pro Gly Pro Ser Met Glu Thr Asp Thr Leu Leu Leu Trp Val Leu
                325                 330                 335

Leu Leu Trp Val Pro Gly Ser Thr Gly Glu Val Gln Leu Val Glu Ser
            340                 345                 350

Gly Gly Gly Glu Val Gln Pro Gly Gly Ser Leu Arg Leu Ser Cys Ala
        355                 360                 365

Ala Ser Gly Leu Leu Phe Ser Ile Tyr Asp Met Asn Trp Tyr Arg Gln
    370                 375                 380

Ala Pro Gly Lys Glu Arg Glu Trp Val Ala Gly Ile Thr Asn Asn Gly
385                 390                 395                 400

Tyr Ser Thr Ala Tyr Ala Glu Ser Val Lys Gly Arg Phe Thr Ile Ser
                405                 410                 415

Arg Asp Asn Ala Lys Asn Thr Val Tyr Leu Gln Met Ser Ser Leu Arg
            420                 425                 430

Ala Glu Asp Thr Ala Val Tyr Tyr Cys His Thr Asp Glu Trp Gly Arg
        435                 440                 445

Glu Tyr Trp Gly Gln Gly Thr Leu Val Thr Val Lys Pro Gly Gly Gly
    450                 455                 460

Gly Ser Gly Val Gln Val Glu Thr Ile Ser Pro Gly Asp Gly Arg Thr
465                 470                 475                 480

Phe Pro Lys Arg Gly Gln Thr Cys Val Val His Tyr Thr Gly Met Leu
                485                 490                 495

Glu Asp Gly Lys Lys Phe Asp Ser Ser Arg Asp Arg Asn Lys Pro Phe
            500                 505                 510

Lys Phe Met Leu Gly Lys Gln Glu Val Ile Arg Gly Trp Glu Glu Gly
        515                 520                 525

Val Ala Gln Met Ser Val Gly Gln Arg Ala Lys Leu Thr Ile Ser Pro
    530                 535                 540

Asp Tyr Ala Tyr Gly Ala Thr Gly His Pro Gly Ile Ile Pro Pro His
545                 550                 555                 560

Ala Thr Leu Val Phe Asp Val Glu Leu Leu Lys Leu Glu Gly Gly Arg
                565                 570                 575

Met Ala Leu Ile Val Leu Gly Val Ala Gly Leu Leu Leu Phe Ile
            580                 585                 590

Gly Leu Gly Ile Phe Phe Lys Lys Lys Pro Leu Cys Leu Gln Arg Glu
        595                 600                 605

Ala Lys Val Pro His Leu Pro Ala Asp Lys Ala Arg Gly Thr Gln Gly
    610                 615                 620

Pro Glu Gln Gln His Leu Leu Ile Thr Ala Pro Ser Ser Ser Ser Ser
625                 630                 635                 640

Ser Leu Glu Ser Ser Ala Ser Ala Leu Asp Arg Arg Ala Pro Thr Arg
                645                 650                 655

Asn Gln Pro Gln Ala Pro Gly Val Glu Ala Ser Gly Ala Gly Glu Ala
            660                 665                 670

Arg Ala Ser Thr Gly Ser Ser Asp Ser Ser Pro Gly Gly His Gly Thr
        675                 680                 685

Gln Val Asn Val Thr Cys Ile Val Asn Val Cys Ser Ser Ser Asp His
    690                 695                 700
```

```
Ser Ser Gln Cys Ser Ser Gln Ala Ser Ser Thr Met Gly Asp Thr Asp
705                 710                 715                 720

Ser Ser Pro Ser Glu Ser Pro Lys Asp Glu Gln Val Pro Phe Ser Lys
            725                 730                 735

Glu Glu Cys Ala Phe Arg Ser Gln Leu Glu Thr Pro Glu Thr Leu Leu
        740                 745                 750

Gly Ser Thr Glu Glu Lys Pro Leu Pro Leu Gly Val Pro Asp Ala Gly
    755                 760                 765

Met Lys Pro Ser
    770

<210> SEQ ID NO 36
<211> LENGTH: 768
<212> TYPE: PRT
<213> ORGANISM: Artificial Sequence
<220> FEATURE:
<223> OTHER INFORMATION: Made in Lab - anti-CLL1 DARIC.TNRF2 fusion
      protein

<400> SEQUENCE: 36

Met Ala Leu Pro Val Thr Ala Leu Leu Leu Pro Leu Ala Leu Leu Leu
1               5                   10                  15

His Ala Ala Arg Pro Gly Ser Ile Leu Trp His Glu Met Trp His Glu
            20                  25                  30

Gly Leu Glu Glu Ala Ser Arg Leu Tyr Phe Gly Glu Arg Asn Val Lys
        35                  40                  45

Gly Met Phe Glu Val Leu Glu Pro Leu His Ala Met Met Glu Arg Gly
    50                  55                  60

Pro Gln Thr Leu Lys Glu Thr Ser Phe Asn Gln Ala Tyr Gly Arg Asp
65                  70                  75                  80

Leu Met Glu Ala Gln Glu Trp Cys Arg Lys Tyr Met Lys Ser Gly Asn
                85                  90                  95

Val Lys Asp Leu Leu Gln Ala Trp Asp Leu Tyr Tyr His Val Phe Arg
            100                 105                 110

Arg Ile Ser Lys Ala Ser Ala Gly Thr Gly Ser Asp Ile Tyr Ile Trp
        115                 120                 125

Ala Pro Leu Ala Gly Thr Cys Gly Val Leu Leu Leu Ser Leu Val Ile
    130                 135                 140

Thr Met His Lys Arg Gly Arg Lys Lys Leu Leu Tyr Ile Phe Lys Gln
145                 150                 155                 160

Pro Phe Met Arg Pro Val Gln Thr Thr Gln Glu Glu Asp Gly Cys Ser
                165                 170                 175

Cys Arg Phe Pro Glu Glu Glu Glu Gly Gly Cys Glu Leu Arg Val Lys
            180                 185                 190

Phe Ser Arg Ser Ala Asp Ala Pro Ala Tyr Gln Gln Gly Gln Asn Gln
        195                 200                 205

Leu Tyr Asn Glu Leu Asn Leu Gly Arg Arg Glu Glu Tyr Asp Val Leu
    210                 215                 220

Asp Lys Arg Arg Gly Arg Asp Pro Glu Met Gly Gly Lys Pro Arg Arg
225                 230                 235                 240

Lys Asn Pro Gln Glu Gly Leu Tyr Asn Glu Leu Gln Lys Asp Lys Met
                245                 250                 255

Ala Glu Ala Tyr Ser Glu Ile Gly Met Lys Gly Glu Arg Arg Arg Gly
            260                 265                 270

Lys Gly His Asp Gly Leu Tyr Gln Gly Leu Ser Thr Ala Thr Lys Asp
        275                 280                 285
```

```
Thr Tyr Asp Ala Leu His Met Gln Ala Leu Pro Pro Arg Ser Gly Ser
            290                 295                 300

Gly Ala Thr Asn Phe Ser Leu Leu Lys Gln Ala Gly Asp Val Glu Glu
305                 310                 315                 320

Asn Pro Gly Pro Ser Met Glu Thr Asp Thr Leu Leu Leu Trp Val Leu
                325                 330                 335

Leu Leu Trp Val Pro Gly Ser Thr Gly Glu Val Gln Leu Val Glu Ser
                340                 345                 350

Gly Gly Gly Glu Val Gln Pro Gly Gly Ser Leu Arg Leu Ser Cys Ala
            355                 360                 365

Ala Ser Gly Arg Thr Phe Glu Tyr Asp Met Val Trp Phe Arg Gln
370                 375                 380

Ala Pro Gly Lys Glu Arg Glu Val Ala Gly Ile Ser Trp Ser Gly
385                 390                 395                 400

Gly Ser Ile Tyr Tyr Ala Glu Ser Val Lys Gly Arg Phe Ser Ile Ser
                405                 410                 415

Arg Asp Asn Ala Lys Asn Thr Val Tyr Leu Glu Met Asn Arg Leu Lys
            420                 425                 430

Pro Glu Asp Thr Ala Val Tyr Tyr Cys Asn Val Gly Ser Tyr Trp Gly
                435                 440                 445

Gln Gly Thr Leu Val Thr Val Lys Pro Gly Gly Gly Ser Gly Val
450                 455                 460

Gln Val Glu Thr Ile Ser Pro Gly Asp Gly Arg Thr Phe Pro Lys Arg
465                 470                 475                 480

Gly Gln Thr Cys Val Val His Tyr Thr Gly Met Leu Glu Asp Gly Lys
                485                 490                 495

Lys Phe Asp Ser Ser Arg Asp Arg Asn Lys Pro Phe Lys Phe Met Leu
                500                 505                 510

Gly Lys Gln Glu Val Ile Arg Gly Trp Glu Glu Gly Val Ala Gln Met
            515                 520                 525

Ser Val Gly Gln Arg Ala Lys Leu Thr Ile Ser Pro Asp Tyr Ala Tyr
530                 535                 540

Gly Ala Thr Gly His Pro Gly Ile Ile Pro Pro His Ala Thr Leu Val
545                 550                 555                 560

Phe Asp Val Glu Leu Leu Lys Leu Glu Gly Gly Arg Met Ala Leu Ile
                565                 570                 575

Val Leu Gly Gly Val Ala Gly Leu Leu Leu Phe Ile Gly Leu Gly Ile
            580                 585                 590

Phe Phe Lys Lys Lys Pro Leu Cys Leu Gln Arg Glu Ala Lys Val Pro
            595                 600                 605

His Leu Pro Ala Asp Lys Ala Arg Gly Thr Gln Gly Pro Glu Gln Gln
610                 615                 620

His Leu Leu Ile Thr Ala Pro Ser Ser Ser Ser Ser Leu Glu Ser
625                 630                 635                 640

Ser Ala Ser Ala Leu Asp Arg Arg Ala Pro Thr Arg Asn Gln Pro Gln
                645                 650                 655

Ala Pro Gly Val Glu Ala Ser Gly Ala Gly Glu Ala Arg Ala Ser Thr
                660                 665                 670

Gly Ser Ser Asp Ser Ser Pro Gly Gly His Gly Thr Gln Val Asn Val
            675                 680                 685

Thr Cys Ile Val Asn Val Cys Ser Ser Ser Asp His Ser Ser Gln Cys
690                 695                 700
```

```
Ser Ser Gln Ala Ser Ser Thr Met Gly Asp Thr Asp Ser Ser Pro Ser
705                 710                 715                 720

Glu Ser Pro Lys Asp Glu Gln Val Pro Phe Ser Lys Glu Glu Cys Ala
            725                 730                 735

Phe Arg Ser Gln Leu Glu Thr Pro Glu Thr Leu Leu Gly Ser Thr Glu
            740                 745                 750

Glu Lys Pro Leu Pro Leu Gly Val Pro Asp Ala Gly Met Lys Pro Ser
            755                 760                 765

<210> SEQ ID NO 37
<211> LENGTH: 775
<212> TYPE: PRT
<213> ORGANISM: Artificial Sequence
<220> FEATURE:
<223> OTHER INFORMATION: Made in Lab - anti-CLL1 DARIC.TNRF2 fusion
      protein

<400> SEQUENCE: 37

Met Ala Leu Pro Val Thr Ala Leu Leu Leu Pro Leu Ala Leu Leu Leu
1               5                   10                  15

His Ala Ala Arg Pro Gly Ser Ile Leu Trp His Glu Met Trp His Glu
            20                  25                  30

Gly Leu Glu Glu Ala Ser Arg Leu Tyr Phe Gly Glu Arg Asn Val Lys
        35                  40                  45

Gly Met Phe Glu Val Leu Glu Pro Leu His Ala Met Met Glu Arg Gly
50                  55                  60

Pro Gln Thr Leu Lys Glu Thr Ser Phe Asn Gln Ala Tyr Gly Arg Asp
65                  70                  75                  80

Leu Met Glu Ala Gln Glu Trp Cys Arg Lys Tyr Met Lys Ser Gly Asn
                85                  90                  95

Val Lys Asp Leu Leu Gln Ala Trp Asp Leu Tyr Tyr His Val Phe Arg
            100                 105                 110

Arg Ile Ser Lys Ala Ser Ala Gly Thr Gly Ser Asp Ile Tyr Ile Trp
        115                 120                 125

Ala Pro Leu Ala Gly Thr Cys Gly Val Leu Leu Leu Ser Leu Val Ile
130                 135                 140

Thr Met His Lys Arg Gly Arg Lys Lys Leu Leu Tyr Ile Phe Lys Gln
145                 150                 155                 160

Pro Phe Met Arg Pro Val Gln Thr Thr Gln Glu Glu Asp Gly Cys Ser
                165                 170                 175

Cys Arg Phe Pro Glu Glu Glu Glu Gly Gly Cys Glu Leu Arg Val Lys
            180                 185                 190

Phe Ser Arg Ser Ala Asp Ala Pro Ala Tyr Gln Gln Gly Gln Asn Gln
        195                 200                 205

Leu Tyr Asn Glu Leu Asn Leu Gly Arg Arg Glu Glu Tyr Asp Val Leu
210                 215                 220

Asp Lys Arg Arg Gly Arg Asp Pro Glu Met Gly Gly Lys Pro Arg Arg
225                 230                 235                 240

Lys Asn Pro Gln Glu Gly Leu Tyr Asn Glu Leu Gln Lys Asp Lys Met
                245                 250                 255

Ala Glu Ala Tyr Ser Glu Ile Gly Met Lys Gly Glu Arg Arg Arg Gly
            260                 265                 270

Lys Gly His Asp Gly Leu Tyr Gln Gly Leu Ser Thr Ala Thr Lys Asp
        275                 280                 285

Thr Tyr Asp Ala Leu His Met Gln Ala Leu Pro Pro Arg Ser Gly Ser
290                 295                 300
```

```
Gly Ala Thr Asn Phe Ser Leu Leu Lys Gln Ala Gly Asp Val Glu Glu
305                 310                 315                 320

Asn Pro Gly Pro Ser Met Glu Thr Asp Thr Leu Leu Leu Trp Val Leu
            325                 330                 335

Leu Leu Trp Val Pro Gly Ser Thr Gly Glu Val Gln Leu Val Glu Ser
        340                 345                 350

Gly Gly Gly Glu Val Gln Pro Gly Gly Ser Leu Arg Leu Ser Cys Ala
            355                 360                 365

Ala Ser Gly Phe Thr Phe Arg Ile Asn Asp Met Gly Trp Tyr Arg Gln
        370                 375                 380

Ala Pro Gly Lys Glu Cys Glu Met Val Ala Gly Ile Ser Asn Asn Gly
385                 390                 395                 400

Phe Ser Thr Ala Tyr Ala Glu Ser Val Lys Gly Arg Phe Thr Ile Ser
                405                 410                 415

Arg Asp Asn Ala Lys Asn Thr Val Tyr Leu Gln Met Ser Ser Leu Arg
            420                 425                 430

Ala Glu Asp Thr Ala Val Tyr Tyr Cys His Arg Thr Asp Glu Gly Ala
        435                 440                 445

Ala His Ala Cys Ser Arg Gly Gln Gly Thr Leu Val Thr Val Lys Pro
    450                 455                 460

Gly Gly Gly Gly Ser Gly Val Gln Val Glu Thr Ile Ser Pro Gly Asp
465                 470                 475                 480

Gly Arg Thr Phe Pro Lys Arg Gly Gln Thr Cys Val Val His Tyr Thr
                485                 490                 495

Gly Met Leu Glu Asp Gly Lys Lys Phe Asp Ser Ser Arg Asp Arg Asn
            500                 505                 510

Lys Pro Phe Lys Phe Met Leu Gly Lys Gln Glu Val Ile Arg Gly Trp
        515                 520                 525

Glu Glu Gly Val Ala Gln Met Ser Val Gly Gln Arg Ala Lys Leu Thr
    530                 535                 540

Ile Ser Pro Asp Tyr Ala Tyr Gly Ala Thr Gly His Pro Gly Ile Ile
545                 550                 555                 560

Pro Pro His Ala Thr Leu Val Phe Asp Val Glu Leu Leu Lys Leu Glu
                565                 570                 575

Gly Gly Arg Met Ala Leu Ile Val Leu Gly Gly Val Ala Gly Leu Leu
            580                 585                 590

Leu Phe Ile Gly Leu Gly Ile Phe Phe Lys Lys Pro Leu Cys Leu
        595                 600                 605

Gln Arg Glu Ala Lys Val Pro His Leu Pro Ala Asp Lys Ala Arg Gly
    610                 615                 620

Thr Gln Gly Pro Glu Gln Gln His Leu Leu Ile Thr Ala Pro Ser Ser
625                 630                 635                 640

Ser Ser Ser Ser Leu Glu Ser Ser Ala Ser Ala Leu Asp Arg Arg Ala
                645                 650                 655

Pro Thr Arg Asn Gln Pro Gln Ala Pro Gly Val Glu Ala Ser Gly Ala
            660                 665                 670

Gly Glu Ala Arg Ala Ser Thr Gly Ser Ser Asp Ser Ser Pro Gly Gly
        675                 680                 685

His Gly Thr Gln Val Asn Val Thr Cys Ile Val Asn Val Cys Ser Ser
    690                 695                 700

Ser Asp His Ser Ser Gln Cys Ser Ser Gln Ala Ser Ser Thr Met Gly
705                 710                 715                 720
```

```
Asp Thr Asp Ser Ser Pro Ser Glu Ser Pro Lys Asp Glu Gln Val Pro
            725                 730                 735

Phe Ser Lys Glu Glu Cys Ala Phe Arg Ser Gln Leu Thr Pro Glu
        740                 745                 750

Thr Leu Leu Gly Ser Thr Glu Glu Lys Pro Leu Pro Leu Gly Val Pro
            755                 760                 765

Asp Ala Gly Met Lys Pro Ser
        770                 775

<210> SEQ ID NO 38
<211> LENGTH: 367
<212> TYPE: PRT
<213> ORGANISM: Artificial Sequence
<220> FEATURE:
<223> OTHER INFORMATION: Made in Lab - anti-CLL-1 VHH chimeric antigen
      receptor

<400> SEQUENCE: 38

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Glu
            20                  25                  30

Val Gln Pro Gly Gly Ser Leu Arg Leu Ser Cys Ala Ala Ser Gly Phe
        35                  40                  45

Leu Phe Ser Ile Tyr Asp Met Asn Trp Tyr Arg Gln Ala Pro Gly Lys
    50                  55                  60

Glu Arg Glu Trp Val Ala Gly Ile Thr Asn Asn Gly Tyr Ser Thr Ala
65                  70                  75                  80

Tyr Ala Glu Ser Val Lys Gly Arg Phe Thr Ile Ser Arg Asp Asn Ala
                85                  90                  95

Lys Asn Thr Ile Tyr Leu Gln Met Ser Ser Leu Arg Ala Glu Asp Thr
            100                 105                 110

Ala Val Tyr Tyr Cys His Ala Asp Leu Thr Lys Ala Tyr Asp Val Glu
        115                 120                 125

Tyr Ala Trp Gly Gln Gly Thr Leu Val Thr Val Lys Pro Ala Ala Ala
    130                 135                 140

Thr Thr Thr Pro Ala Pro Arg Pro Pro Thr Pro Ala Pro Thr Ile Ala
145                 150                 155                 160

Ser Gln Pro Leu Ser Leu Arg Pro Glu Ala Cys Arg Pro Ala Ala Gly
                165                 170                 175

Gly Ala Val His Thr Arg Gly Leu Asp Phe Ala Cys Asp Ile Tyr Ile
            180                 185                 190

Trp Ala Pro Leu Ala Gly Thr Cys Gly Val Leu Leu Leu Ser Leu Val
        195                 200                 205

Ile Thr Leu Tyr Cys Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu Arg
                245                 250                 255

Val Lys Phe Ser Arg Ser Ala Asp Ala Pro Ala Tyr Gln Gln Gly Gln
            260                 265                 270

Asn Gln Leu Tyr Asn Glu Leu Asn Leu Gly Arg Arg Glu Glu Tyr Asp
        275                 280                 285

Val Leu Asp Lys Arg Arg Gly Arg Asp Pro Glu Met Gly Gly Lys Pro
    290                 295                 300
```

Arg Arg Lys Asn Pro Gln Glu Gly Leu Tyr Asn Glu Leu Gln Lys Asp
305                 310                 315                 320

Lys Met Ala Glu Ala Tyr Ser Glu Ile Gly Met Lys Gly Glu Arg Arg
            325                 330                 335

Arg Gly Lys Gly His Asp Gly Leu Tyr Gln Gly Leu Ser Thr Ala Thr
        340                 345                 350

Lys Asp Thr Tyr Asp Ala Leu His Met Gln Ala Leu Pro Pro Arg
        355                 360                 365

<210> SEQ ID NO 39
<211> LENGTH: 368
<212> TYPE: PRT
<213> ORGANISM: Artificial Sequence
<220> FEATURE:
<223> OTHER INFORMATION: Made in Lab - anti-CLL-1 VHH chimeric antigen
      receptor

<400> SEQUENCE: 39

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Glu
            20                  25                  30

Val Gln Pro Gly Gly Ser Leu Arg Leu Ser Cys Ala Ala Ser Gly Phe
        35                  40                  45

Thr Phe Ser Val Tyr Asp Met Asn Trp Tyr Arg Gln Ala Pro Gly Lys
    50                  55                  60

Glu Arg Glu Trp Val Ser Gly Ile Ser Asn Asn Gly Phe Ser Thr Ala
65                  70                  75                  80

Tyr Ala Glu Ser Val Lys Gly Arg Phe Thr Ile Ser Arg Asp Asn Ala
                85                  90                  95

Lys Asn Thr Leu Tyr Leu Gln Met Ser Ser Leu Arg Ala Glu Asp Thr
            100                 105                 110

Ala Val Tyr Tyr Cys Asn Leu Asp Val His Gly Arg Val Gly Ala Gln
        115                 120                 125

Gly Asp Tyr Trp Gly Gln Gly Thr Leu Val Thr Val Lys Pro Ala Ala
    130                 135                 140

Ala Thr Thr Thr Pro Ala Pro Arg Pro Pro Thr Pro Ala Pro Thr Ile
145                 150                 155                 160

Ala Ser Gln Pro Leu Ser Leu Arg Pro Glu Ala Cys Arg Pro Ala Ala
                165                 170                 175

Gly Gly Ala Val His Thr Arg Gly Leu Asp Phe Ala Cys Asp Ile Tyr
            180                 185                 190

Ile Trp Ala Pro Leu Ala Gly Thr Cys Gly Val Leu Leu Leu Ser Leu
        195                 200                 205

Val Ile Thr Leu Tyr Cys Lys Arg Gly Arg Lys Lys Leu Leu Tyr Ile
    210                 215                 220

Phe Lys Gln Pro Phe Met Arg Pro Val Gln Thr Thr Gln Glu Glu Asp
225                 230                 235                 240

Gly Cys Ser Cys Arg Phe Pro Glu Glu Glu Glu Gly Gly Cys Glu Leu
                245                 250                 255

Arg Val Lys Phe Ser Arg Ser Ala Asp Ala Pro Ala Tyr Gln Gln Gly
            260                 265                 270

Gln Asn Gln Leu Tyr Asn Glu Leu Asn Leu Gly Arg Arg Glu Glu Tyr
        275                 280                 285

Asp Val Leu Asp Lys Arg Arg Gly Arg Asp Pro Glu Met Gly Gly Lys

```
            290                 295                 300
Pro Arg Arg Lys Asn Pro Gln Glu Gly Leu Tyr Asn Glu Leu Gln Lys
305                 310                 315                 320

Asp Lys Met Ala Glu Ala Tyr Ser Glu Ile Gly Met Lys Gly Glu Arg
                325                 330                 335

Arg Arg Gly Lys Gly His Asp Gly Leu Tyr Gln Gly Leu Ser Thr Ala
                340                 345                 350

Thr Lys Asp Thr Tyr Asp Ala Leu His Met Gln Ala Leu Pro Pro Arg
                355                 360                 365

<210> SEQ ID NO 40
<211> LENGTH: 376
<212> TYPE: PRT
<213> ORGANISM: Artificial Sequence
<220> FEATURE:
<223> OTHER INFORMATION: Made in Lab - anti-CLL-1 VHH chimeric antigen
      receptor

<400> SEQUENCE: 40

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Glu
                20                  25                  30

Val Gln Pro Gly Gly Ser Leu Arg Leu Ser Cys Ala Ala Ser Gly Phe
            35                  40                  45

Thr Phe Asp Asp Tyr Ala Ile Gly Trp Phe Arg Gln Ala Pro Gly Lys
        50                  55                  60

Glu Arg Glu Gly Val Ser Thr Ile Ser Ser Asp Gly Ser Thr Tyr Tyr
65                  70                  75                  80

Tyr Ala Glu Ser Val Lys Gly Arg Phe Thr Ile Ser Arg Asp Asn Ala
                85                  90                  95

Lys Asn Thr Val Tyr Leu Gln Met Ser Ser Leu Arg Ala Glu Asp Thr
            100                 105                 110

Ala Val Tyr Tyr Cys Ala Leu Arg Glu Gly Leu Pro Leu Leu Leu Asp
        115                 120                 125

Thr Leu Trp Arg Gln Pro Val Glu Tyr Asp Tyr Trp Gly Gln Gly Thr
    130                 135                 140

Gln Val Thr Val Lys Pro Ala Ala Ala Thr Thr Thr Pro Ala Pro Arg
145                 150                 155                 160

Pro Pro Thr Pro Ala Pro Thr Ile Ala Ser Gln Pro Leu Ser Leu Arg
                165                 170                 175

Pro Glu Ala Cys Arg Pro Ala Ala Gly Gly Ala Val His Thr Arg Gly
            180                 185                 190

Leu Asp Phe Ala Cys Asp Ile Tyr Ile Trp Ala Pro Leu Ala Gly Thr
        195                 200                 205

Cys Gly Val Leu Leu Leu Ser Leu Val Ile Thr Leu Tyr Cys Lys Arg
    210                 215                 220

Gly Arg Lys Lys Leu Leu Tyr Ile Phe Lys Gln Pro Phe Met Arg Pro
225                 230                 235                 240

Val Gln Thr Thr Gln Glu Glu Asp Gly Cys Ser Cys Arg Phe Pro Glu
                245                 250                 255

Glu Glu Glu Gly Gly Cys Glu Leu Arg Val Lys Phe Ser Arg Ser Ala
            260                 265                 270

Asp Ala Pro Ala Tyr Gln Gln Gly Gln Asn Gln Leu Tyr Asn Glu Leu
        275                 280                 285
```

```
Asn Leu Gly Arg Arg Glu Glu Tyr Asp Val Leu Asp Lys Arg Arg Gly
    290                 295                 300
Arg Asp Pro Glu Met Gly Gly Lys Pro Arg Arg Lys Asn Pro Gln Glu
305                 310                 315                 320
Gly Leu Tyr Asn Glu Leu Gln Lys Asp Lys Met Ala Glu Ala Tyr Ser
                325                 330                 335
Glu Ile Gly Met Lys Gly Glu Arg Arg Arg Gly Lys Gly His Asp Gly
                340                 345                 350
Leu Tyr Gln Gly Leu Ser Thr Ala Thr Lys Asp Thr Tyr Asp Ala Leu
            355                 360                 365
His Met Gln Ala Leu Pro Pro Arg
    370                 375

<210> SEQ ID NO 41
<211> LENGTH: 363
<212> TYPE: PRT
<213> ORGANISM: Artificial Sequence
<220> FEATURE:
<223> OTHER INFORMATION: Made in Lab - anti-CLL-1 VHH chimeric antigen
      receptor

<400> SEQUENCE: 41

Met Ala Leu Pro Val Thr Ala Leu Leu Leu Pro Leu Ala Leu Leu Leu
1               5                   10                  15
His Ala Ala Arg Pro Glu Val Gln Leu Val Glu Ser Gly Gly Gly Glu
                20                  25                  30
Val Gln Pro Gly Gly Ser Leu Arg Leu Ser Cys Ala Ala Ser Gly Leu
            35                  40                  45
Leu Phe Ser Ile Tyr Asp Met Asn Trp Tyr Arg Gln Ala Pro Gly Lys
    50                  55                  60
Glu Arg Glu Trp Val Ala Gly Ile Thr Asn Asn Gly Tyr Ser Thr Ala
65                  70                  75                  80
Tyr Ala Glu Ser Val Lys Gly Arg Phe Thr Ile Ser Arg Asp Asn Ala
                85                  90                  95
Lys Asn Thr Val Tyr Leu Gln Met Ser Ser Leu Arg Ala Glu Asp Thr
                100                 105                 110
Ala Val Tyr Tyr Cys His Thr Asp Glu Trp Gly Arg Glu Tyr Trp Gly
            115                 120                 125
Gln Gly Thr Leu Val Thr Val Lys Pro Ala Ala Thr Thr Thr Pro
    130                 135                 140
Ala Pro Arg Pro Pro Thr Pro Ala Pro Thr Ile Ala Ser Gln Pro Leu
145                 150                 155                 160
Ser Leu Arg Pro Glu Ala Cys Arg Pro Ala Ala Gly Gly Ala Val His
                165                 170                 175
Thr Arg Gly Leu Asp Phe Ala Cys Asp Ile Tyr Ile Trp Ala Pro Leu
                180                 185                 190
Ala Gly Thr Cys Gly Val Leu Leu Leu Ser Leu Val Ile Thr Leu Tyr
            195                 200                 205
Cys Lys Arg Gly Arg Lys Lys Leu Leu Tyr Ile Phe Lys Gln Pro Phe
    210                 215                 220
Met Arg Pro Val Gln Thr Thr Gln Glu Glu Asp Gly Cys Ser Cys Arg
225                 230                 235                 240
Phe Pro Glu Glu Glu Glu Gly Gly Cys Glu Leu Arg Val Lys Phe Ser
                245                 250                 255
Arg Ser Ala Asp Ala Pro Ala Tyr Gln Gln Gly Gln Asn Gln Leu Tyr
                260                 265                 270
```

```
Asn Glu Leu Asn Leu Gly Arg Arg Glu Glu Tyr Asp Val Leu Asp Lys
            275                 280                 285

Arg Arg Gly Arg Asp Pro Glu Met Gly Gly Lys Pro Arg Arg Lys Asn
    290                 295                 300

Pro Gln Glu Gly Leu Tyr Asn Glu Leu Gln Lys Asp Lys Met Ala Glu
305                 310                 315                 320

Ala Tyr Ser Glu Ile Gly Met Lys Gly Glu Arg Arg Arg Gly Lys Gly
                325                 330                 335

His Asp Gly Leu Tyr Gln Gly Leu Ser Thr Ala Thr Lys Asp Thr Tyr
            340                 345                 350

Asp Ala Leu His Met Gln Ala Leu Pro Pro Arg
            355                 360
```

<210> SEQ ID NO 42
<211> LENGTH: 359
<212> TYPE: PRT
<213> ORGANISM: Artificial Sequence
<220> FEATURE:
<223> OTHER INFORMATION: Made in Lab - anti-CLL-1 VHH chimeric antigen
      receptor

<400> SEQUENCE: 42

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Glu
            20                  25                  30

Val Gln Pro Gly Gly Ser Leu Arg Leu Ser Cys Ala Ala Ser Gly Arg
        35                  40                  45

Thr Phe Glu Tyr Asp Asp Met Val Trp Phe Arg Gln Ala Pro Gly Lys
    50                  55                  60

Glu Arg Glu Glu Val Ala Gly Ile Ser Trp Ser Gly Gly Ser Ile Tyr
65                  70                  75                  80

Tyr Ala Glu Ser Val Lys Gly Arg Phe Ser Ile Ser Arg Asp Asn Ala
                85                  90                  95

Lys Asn Thr Val Tyr Leu Glu Met Asn Arg Leu Lys Pro Glu Asp Thr
            100                 105                 110

Ala Val Tyr Tyr Cys Asn Val Gly Ser Tyr Trp Gly Gln Gly Thr Leu
        115                 120                 125

Val Thr Val Lys Pro Ala Ala Ala Thr Thr Pro Ala Pro Arg Pro
    130                 135                 140

Pro Thr Pro Ala Pro Thr Ile Ala Ser Gln Pro Leu Ser Leu Arg Pro
145                 150                 155                 160

Glu Ala Cys Arg Pro Ala Ala Gly Gly Ala Val His Thr Arg Gly Leu
                165                 170                 175

Asp Phe Ala Cys Asp Ile Tyr Ile Trp Ala Pro Leu Ala Gly Thr Cys
            180                 185                 190

Gly Val Leu Leu Leu Ser Leu Val Ile Thr Leu Tyr Cys Lys Arg Gly
        195                 200                 205

Arg Lys Lys Leu Leu Tyr Ile Phe Lys Gln Pro Phe Met Arg Pro Val
    210                 215                 220

Gln Thr Thr Gln Glu Glu Asp Gly Cys Ser Cys Arg Phe Pro Glu Glu
225                 230                 235                 240

Glu Glu Gly Gly Cys Glu Leu Arg Val Lys Phe Ser Arg Ser Ala Asp
                245                 250                 255

Ala Pro Ala Tyr Gln Gln Gly Gln Asn Gln Leu Tyr Asn Glu Leu Asn
```

```
                260                 265                 270
Leu Gly Arg Arg Glu Tyr Asp Val Leu Asp Lys Arg Arg Gly Arg
            275                 280                 285

Asp Pro Glu Met Gly Gly Lys Pro Arg Arg Lys Asn Pro Gln Glu Gly
        290                 295                 300

Leu Tyr Asn Glu Leu Gln Lys Asp Lys Met Ala Glu Ala Tyr Ser Glu
305                 310                 315                 320

Ile Gly Met Lys Gly Glu Arg Arg Arg Gly Lys Gly His Asp Gly Leu
                325                 330                 335

Tyr Gln Gly Leu Ser Thr Ala Thr Lys Asp Thr Tyr Asp Ala Leu His
            340                 345                 350

Met Gln Ala Leu Pro Pro Arg
            355

<210> SEQ ID NO 43
<211> LENGTH: 366
<212> TYPE: PRT
<213> ORGANISM: Artificial Sequence
<220> FEATURE:
<223> OTHER INFORMATION: Made in Lab - anti-CLL-1 VHH chimeric antigen
      receptor

<400> SEQUENCE: 43

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Glu
            20                  25                  30

Val Gln Pro Gly Gly Ser Leu Arg Leu Ser Cys Ala Ala Ser Gly Phe
        35                  40                  45

Thr Phe Arg Ile Asn Asp Met Gly Trp Tyr Arg Gln Ala Pro Gly Lys
    50                  55                  60

Glu Cys Glu Met Val Ala Gly Ile Ser Asn Asn Gly Phe Ser Thr Ala
65                  70                  75                  80

Tyr Ala Glu Ser Val Lys Gly Arg Phe Thr Ile Ser Arg Asp Asn Ala
                85                  90                  95

Lys Asn Thr Val Tyr Leu Gln Met Ser Ser Leu Arg Ala Glu Asp Thr
            100                 105                 110

Ala Val Tyr Tyr Cys His Arg Thr Asp Glu Gly Ala Ala His Ala Cys
        115                 120                 125

Ser Arg Gly Gln Gly Thr Leu Val Thr Val Lys Pro Ala Ala Ala Thr
    130                 135                 140

Thr Thr Pro Ala Pro Arg Pro Pro Thr Pro Ala Pro Thr Ile Ala Ser
145                 150                 155                 160

Gln Pro Leu Ser Leu Arg Pro Glu Ala Cys Arg Pro Ala Ala Gly Gly
                165                 170                 175

Ala Val His Thr Arg Gly Leu Asp Phe Ala Cys Asp Ile Tyr Ile Trp
            180                 185                 190

Ala Pro Leu Ala Gly Thr Cys Gly Val Leu Leu Leu Ser Leu Val Ile
        195                 200                 205

Thr Leu Tyr Cys Lys Arg Gly Arg Lys Lys Leu Leu Tyr Ile Phe Lys
    210                 215                 220

Gln Pro Phe Met Arg Pro Val Gln Thr Thr Gln Glu Glu Asp Gly Cys
225                 230                 235                 240

Ser Cys Arg Phe Pro Glu Glu Glu Glu Gly Gly Cys Glu Leu Arg Val
                245                 250                 255
```

```
Lys Phe Ser Arg Ser Ala Asp Ala Pro Ala Tyr Gln Gln Gly Gln Asn
            260                 265                 270

Gln Leu Tyr Asn Glu Leu Asn Leu Gly Arg Arg Glu Glu Tyr Asp Val
            275                 280                 285

Leu Asp Lys Arg Arg Gly Arg Asp Pro Glu Met Gly Gly Lys Pro Arg
            290                 295                 300

Arg Lys Asn Pro Gln Glu Gly Leu Tyr Asn Glu Leu Gln Lys Asp Lys
305                 310                 315                 320

Met Ala Glu Ala Tyr Ser Glu Ile Gly Met Lys Gly Glu Arg Arg Arg
                    325                 330                 335

Gly Lys Gly His Asp Gly Leu Tyr Gln Gly Leu Ser Thr Ala Thr Lys
            340                 345                 350

Asp Thr Tyr Asp Ala Leu His Met Gln Ala Leu Pro Pro Arg
            355                 360                 365

<210> SEQ ID NO 44
<211> LENGTH: 364
<212> TYPE: PRT
<213> ORGANISM: Artificial Sequence
<220> FEATURE:
<223> OTHER INFORMATION: Made in Lab - anti-CLL-1 VHH chimeric antigen
      receptor

<400> SEQUENCE: 44

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Glu
            20                  25                  30

Val Gln Pro Gly Gly Ser Leu Arg Leu Ser Cys Ala Ala Ser Gly Phe
            35                  40                  45

Leu Phe Ser Ile Tyr Asp Met Asn Trp Tyr Arg Gln Ala Pro Gly Lys
        50                  55                  60

Glu Arg Glu Trp Val Ala Gly Ile Thr Asn Asn Gly Tyr Ser Thr Ala
65                  70                  75                  80

Tyr Ala Glu Ser Val Lys Gly Arg Phe Thr Ile Ser Arg Asp Asn Ala
                85                  90                  95

Lys Asn Thr Ile Tyr Leu Gln Met Ser Ser Leu Arg Ala Glu Asp Thr
            100                 105                 110

Ala Val Tyr Tyr Cys His Ala Asp Leu Thr Lys Ala Tyr Asp Val Glu
            115                 120                 125

Tyr Ala Trp Gly Gln Gly Thr Leu Val Thr Val Lys Pro Thr Thr Thr
        130                 135                 140

Pro Ala Pro Arg Pro Pro Thr Pro Ala Pro Thr Ile Ala Ser Gln Pro
145                 150                 155                 160

Leu Ser Leu Arg Pro Glu Ala Cys Arg Pro Ala Ala Gly Gly Ala Val
                165                 170                 175

His Thr Arg Gly Leu Asp Phe Ala Cys Asp Ile Tyr Ile Trp Ala Pro
            180                 185                 190

Leu Ala Gly Thr Cys Gly Val Leu Leu Leu Ser Leu Val Ile Thr Leu
            195                 200                 205

Tyr Cys Lys Arg Gly Arg Lys Lys Leu Leu Tyr Ile Phe Lys Gln Pro
        210                 215                 220

Phe Met Arg Pro Val Gln Thr Thr Gln Glu Glu Asp Gly Cys Ser Cys
225                 230                 235                 240

Arg Phe Pro Glu Glu Glu Glu Gly Gly Cys Glu Leu Arg Val Lys Phe
                245                 250                 255
```

```
Ser Arg Ser Ala Asp Ala Pro Ala Tyr Gln Gln Gly Gln Asn Gln Leu
            260                 265                 270

Tyr Asn Glu Leu Asn Leu Gly Arg Arg Glu Glu Tyr Asp Val Leu Asp
            275                 280                 285

Lys Arg Arg Gly Arg Asp Pro Glu Met Gly Gly Lys Pro Arg Arg Lys
            290                 295                 300

Asn Pro Gln Glu Gly Leu Tyr Asn Glu Leu Gln Lys Asp Lys Met Ala
305                 310                 315                 320

Glu Ala Tyr Ser Glu Ile Gly Met Lys Gly Glu Arg Arg Arg Gly Lys
                325                 330                 335

Gly His Asp Gly Leu Tyr Gln Gly Leu Ser Thr Ala Thr Lys Asp Thr
                340                 345                 350

Tyr Asp Ala Leu His Met Gln Ala Leu Pro Pro Arg
            355                 360
```

<210> SEQ ID NO 45
<211> LENGTH: 365
<212> TYPE: PRT
<213> ORGANISM: Artificial Sequence
<220> FEATURE:
<223> OTHER INFORMATION: Made in Lab - anti-CLL-1 VHH chimeric antigen
      receptor

<400> SEQUENCE: 45

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Glu
            20                  25                  30

Val Gln Pro Gly Gly Ser Leu Arg Leu Ser Cys Ala Ala Ser Gly Phe
            35                  40                  45

Thr Phe Ser Val Tyr Asp Met Asn Trp Tyr Arg Gln Ala Pro Gly Lys
        50                  55                  60

Glu Arg Glu Trp Val Ser Gly Ile Ser Asn Asn Gly Phe Ser Thr Ala
65                  70                  75                  80

Tyr Ala Glu Ser Val Lys Gly Arg Phe Thr Ile Ser Arg Asp Asn Ala
                85                  90                  95

Lys Asn Thr Leu Tyr Leu Gln Met Ser Ser Leu Arg Ala Glu Asp Thr
            100                 105                 110

Ala Val Tyr Tyr Cys Asn Leu Asp Val His Gly Arg Val Gly Ala Gln
            115                 120                 125

Gly Asp Tyr Trp Gly Gln Gly Thr Leu Val Thr Val Lys Pro Thr Thr
        130                 135                 140

Thr Pro Ala Pro Arg Pro Pro Thr Pro Ala Pro Thr Ile Ala Ser Gln
145                 150                 155                 160

Pro Leu Ser Leu Arg Pro Glu Ala Cys Arg Pro Ala Ala Gly Gly Ala
                165                 170                 175

Val His Thr Arg Gly Leu Asp Phe Ala Cys Asp Ile Tyr Ile Trp Ala
            180                 185                 190

Pro Leu Ala Gly Thr Cys Gly Val Leu Leu Leu Ser Leu Val Ile Thr
            195                 200                 205

Leu Tyr Cys Lys Arg Gly Arg Lys Lys Leu Leu Tyr Ile Phe Lys Gln
        210                 215                 220

Pro Phe Met Arg Pro Val Gln Thr Thr Gln Glu Glu Asp Gly Cys Ser
225                 230                 235                 240

Cys Arg Phe Pro Glu Glu Glu Glu Gly Gly Cys Glu Leu Arg Val Lys
```

-continued

```
                245                 250                 255
Phe Ser Arg Ser Ala Asp Ala Pro Ala Tyr Gln Gln Gly Gln Asn Gln
            260                 265                 270

Leu Tyr Asn Glu Leu Asn Leu Gly Arg Arg Glu Glu Tyr Asp Val Leu
            275                 280                 285

Asp Lys Arg Arg Gly Arg Asp Pro Glu Met Gly Gly Lys Pro Arg Arg
            290                 295                 300

Lys Asn Pro Gln Glu Gly Leu Tyr Asn Glu Leu Gln Lys Asp Lys Met
305                 310                 315                 320

Ala Glu Ala Tyr Ser Glu Ile Gly Met Lys Gly Glu Arg Arg Arg Gly
                325                 330                 335

Lys Gly His Asp Gly Leu Tyr Gln Gly Leu Ser Thr Ala Thr Lys Asp
                340                 345                 350

Thr Tyr Asp Ala Leu His Met Gln Ala Leu Pro Pro Arg
                355                 360                 365

<210> SEQ ID NO 46
<211> LENGTH: 373
<212> TYPE: PRT
<213> ORGANISM: Artificial Sequence
<220> FEATURE:
<223> OTHER INFORMATION: Made in Lab - anti-CLL-1 VHH chimeric antigen
      receptor

<400> SEQUENCE: 46

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Glu
            20                  25                  30

Val Gln Pro Gly Gly Ser Leu Arg Leu Ser Cys Ala Ala Ser Gly Phe
        35                  40                  45

Thr Phe Asp Asp Tyr Ala Ile Gly Trp Phe Arg Gln Ala Pro Gly Lys
    50                  55                  60

Glu Arg Glu Gly Val Ser Thr Ile Ser Ser Ser Asp Gly Ser Thr Tyr
65                  70                  75                  80

Tyr Ala Glu Ser Val Lys Gly Arg Phe Thr Ile Ser Arg Asp Asn Ala
                85                  90                  95

Lys Asn Thr Val Tyr Leu Gln Met Ser Ser Leu Arg Ala Glu Asp Thr
            100                 105                 110

Ala Val Tyr Tyr Cys Ala Leu Arg Glu Gly Leu Pro Leu Leu Leu Asp
        115                 120                 125

Thr Leu Trp Arg Gln Pro Val Glu Tyr Asp Tyr Trp Gly Gln Gly Thr
    130                 135                 140

Gln Val Thr Val Lys Pro Thr Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
            180                 185                 190

Ala Cys Asp Ile Tyr Ile Trp Ala Pro Leu Ala Gly Thr Cys Gly Val
        195                 200                 205

Leu Leu Leu Ser Leu Val Ile Thr Leu Tyr Cys Lys Arg Gly Arg Lys
    210                 215                 220

Lys Leu Leu Tyr Ile Phe Lys Gln Pro Phe Met Arg Pro Val Gln Thr
225                 230                 235                 240
```

```
Thr Gln Glu Glu Asp Gly Cys Ser Cys Arg Phe Pro Glu Glu Glu
                245                 250                 255

Gly Gly Cys Glu Leu Arg Val Lys Phe Ser Arg Ser Ala Asp Ala Pro
            260                 265                 270

Ala Tyr Gln Gln Gly Gln Asn Gln Leu Tyr Asn Glu Leu Asn Leu Gly
            275                 280                 285

Arg Arg Glu Glu Tyr Asp Val Leu Asp Lys Arg Arg Gly Arg Asp Pro
            290                 295                 300

Glu Met Gly Gly Lys Pro Arg Arg Lys Asn Pro Gln Glu Gly Leu Tyr
305                 310                 315                 320

Asn Glu Leu Gln Lys Asp Lys Met Ala Glu Ala Tyr Ser Glu Ile Gly
                325                 330                 335

Met Lys Gly Glu Arg Arg Arg Gly Lys Gly His Asp Gly Leu Tyr Gln
            340                 345                 350

Gly Leu Ser Thr Ala Thr Lys Asp Thr Tyr Asp Ala Leu His Met Gln
            355                 360                 365

Ala Leu Pro Pro Arg
        370

<210> SEQ ID NO 47
<211> LENGTH: 360
<212> TYPE: PRT
<213> ORGANISM: Artificial Sequence
<220> FEATURE:
<223> OTHER INFORMATION: Made in Lab - anti-CLL-1 VHH chimeric antigen
      receptor

<400> SEQUENCE: 47

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Glu
            20                  25                  30

Val Gln Pro Gly Gly Ser Leu Arg Leu Ser Cys Ala Ala Ser Gly Leu
        35                  40                  45

Leu Phe Ser Ile Tyr Asp Met Asn Trp Tyr Arg Gln Ala Pro Gly Lys
    50                  55                  60

Glu Arg Glu Trp Val Ala Gly Ile Thr Asn Asn Gly Tyr Ser Thr Ala
65                  70                  75                  80

Tyr Ala Glu Ser Val Lys Gly Arg Phe Thr Ile Ser Arg Asp Asn Ala
                85                  90                  95

Lys Asn Thr Val Tyr Leu Gln Met Ser Ser Leu Arg Ala Glu Asp Thr
            100                 105                 110

Ala Val Tyr Tyr Cys His Thr Asp Glu Trp Gly Arg Glu Tyr Trp Gly
        115                 120                 125

Gln Gly Thr Leu Val Thr Val Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Lys Arg
        195                 200                 205

Gly Arg Lys Lys Leu Leu Tyr Ile Phe Lys Gln Pro Phe Met Arg Pro
    210                 215                 220
```

```
Val Gln Thr Thr Gln Glu Glu Asp Gly Cys Ser Cys Arg Phe Pro Glu
225                 230                 235                 240

Glu Glu Glu Gly Gly Cys Glu Leu Arg Val Lys Phe Ser Arg Ser Ala
            245                 250                 255

Asp Ala Pro Ala Tyr Gln Gln Gly Gln Asn Gln Leu Tyr Asn Glu Leu
            260                 265                 270

Asn Leu Gly Arg Arg Glu Glu Tyr Asp Val Leu Asp Lys Arg Arg Gly
        275                 280                 285

Arg Asp Pro Glu Met Gly Gly Lys Pro Arg Arg Lys Asn Pro Gln Glu
        290                 295                 300

Gly Leu Tyr Asn Glu Leu Gln Lys Asp Lys Met Ala Glu Ala Tyr Ser
305                 310                 315                 320

Glu Ile Gly Met Lys Gly Glu Arg Arg Arg Gly Lys Gly His Asp Gly
                325                 330                 335

Leu Tyr Gln Gly Leu Ser Thr Ala Thr Lys Asp Thr Tyr Asp Ala Leu
            340                 345                 350

His Met Gln Ala Leu Pro Pro Arg
            355                 360

<210> SEQ ID NO 48
<211> LENGTH: 356
<212> TYPE: PRT
<213> ORGANISM: Artificial Sequence
<220> FEATURE:
<223> OTHER INFORMATION: Made in Lab - anti-CLL-1 VHH chimeric antigen
      receptor

<400> SEQUENCE: 48

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Glu
            20                  25                  30

Val Gln Pro Gly Gly Ser Leu Arg Leu Ser Cys Ala Ala Ser Gly Arg
        35                  40                  45

Thr Phe Glu Tyr Asp Asp Met Val Trp Phe Arg Gln Ala Pro Gly Lys
50                  55                  60

Glu Arg Glu Glu Val Ala Gly Ile Ser Trp Ser Gly Ser Ile Tyr
65                  70                  75              80

Tyr Ala Glu Ser Val Lys Gly Arg Phe Ser Ile Ser Arg Asp Asn Ala
                85                  90                  95

Lys Asn Thr Val Tyr Leu Glu Met Asn Arg Leu Lys Pro Glu Asp Thr
            100                 105                 110

Ala Val Tyr Tyr Cys Asn Val Gly Ser Tyr Trp Gly Gln Gly Thr Leu
        115                 120                 125

Val Thr Val Lys Pro Thr Thr Thr Pro Ala Pro Arg Pro Pro Thr Pro
130                 135                 140

Ala Pro Thr Ile Ala Ser Gln Pro Leu Ser Leu Arg Pro Glu Ala Cys
145                 150                 155                 160

Arg Pro Ala Ala Gly Gly Ala Val His Thr Arg Gly Leu Asp Phe Ala
                165                 170                 175

Cys Asp Ile Tyr Ile Trp Ala Pro Leu Ala Gly Thr Cys Gly Val Leu
            180                 185                 190

Leu Leu Ser Leu Val Ile Thr Leu Tyr Cys Lys Arg Gly Arg Lys Lys
        195                 200                 205

Leu Leu Tyr Ile Phe Lys Gln Pro Phe Met Arg Pro Val Gln Thr Thr
```

```
                210                 215                 220
Gln Glu Glu Asp Gly Cys Ser Cys Arg Phe Pro Glu Glu Glu Gly
225                 230                 235                 240

Gly Cys Glu Leu Arg Val Lys Phe Ser Arg Ser Ala Asp Ala Pro Ala
                245                 250                 255

Tyr Gln Gln Gly Gln Asn Gln Leu Tyr Asn Glu Leu Asn Leu Gly Arg
                260                 265                 270

Arg Glu Glu Tyr Asp Val Leu Asp Lys Arg Arg Gly Arg Asp Pro Glu
                275                 280                 285

Met Gly Gly Lys Pro Arg Arg Lys Asn Pro Gln Glu Gly Leu Tyr Asn
    290                 295                 300

Glu Leu Gln Lys Asp Lys Met Ala Glu Ala Tyr Ser Glu Ile Gly Met
305                 310                 315                 320

Lys Gly Glu Arg Arg Arg Gly Lys Gly His Asp Gly Leu Tyr Gln Gly
                325                 330                 335

Leu Ser Thr Ala Thr Lys Asp Thr Tyr Asp Ala Leu His Met Gln Ala
                340                 345                 350

Leu Pro Pro Arg
            355

<210> SEQ ID NO 49
<211> LENGTH: 356
<212> TYPE: PRT
<213> ORGANISM: Artificial Sequence
<220> FEATURE:
<223> OTHER INFORMATION: Made in Lab - anti-CLL-1 VHH chimeric antigen
      receptor

<400> SEQUENCE: 49

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Glu
                20                  25                  30

Val Gln Pro Gly Gly Ser Leu Arg Leu Ser Cys Ala Ala Ser Gly Arg
                35                  40                  45

Thr Phe Glu Tyr Asp Asp Met Val Trp Phe Arg Gln Ala Pro Gly Lys
    50                  55                  60

Glu Arg Glu Glu Val Ala Gly Ile Ser Trp Ser Gly Ser Ile Tyr
65                  70                  75                  80

Tyr Ala Glu Ser Val Lys Gly Arg Phe Ser Ile Ser Arg Asp Asn Ala
                85                  90                  95

Lys Asn Thr Val Tyr Leu Glu Met Asn Arg Leu Lys Pro Glu Asp Thr
                100                 105                 110

Ala Val Tyr Tyr Cys Asn Val Gly Ser Tyr Trp Gly Gln Gly Thr Leu
                115                 120                 125

Val Thr Val Lys Pro Thr Thr Thr Pro Ala Pro Arg Pro Pro Thr Pro
    130                 135                 140

Ala Pro Thr Ile Ala Ser Gln Pro Leu Ser Leu Arg Pro Glu Ala Cys
145                 150                 155                 160

Arg Pro Ala Ala Gly Gly Ala Val His Thr Arg Gly Leu Asp Phe Ala
                165                 170                 175

Cys Asp Ile Tyr Ile Trp Ala Pro Leu Ala Gly Thr Cys Gly Val Leu
                180                 185                 190

Leu Leu Ser Leu Val Ile Thr Leu Tyr Cys Lys Arg Gly Arg Lys Lys
                195                 200                 205
```

-continued

Leu Leu Tyr Ile Phe Lys Gln Pro Phe Met Arg Pro Val Gln Thr Thr
    210                 215                 220

Gln Glu Glu Asp Gly Cys Ser Cys Arg Phe Pro Glu Glu Glu Glu Gly
225                 230                 235                 240

Gly Cys Glu Leu Arg Val Lys Phe Ser Arg Ser Ala Asp Ala Pro Ala
                245                 250                 255

Tyr Gln Gln Gly Gln Asn Gln Leu Tyr Asn Glu Leu Asn Leu Gly Arg
                260                 265                 270

Arg Glu Glu Tyr Asp Val Leu Asp Lys Arg Arg Gly Arg Asp Pro Glu
            275                 280                 285

Met Gly Gly Lys Pro Arg Arg Lys Asn Pro Gln Glu Gly Leu Tyr Asn
    290                 295                 300

Glu Leu Gln Lys Asp Lys Met Ala Glu Ala Tyr Ser Glu Ile Gly Met
305                 310                 315                 320

Lys Gly Glu Arg Arg Arg Gly Lys Gly His Asp Gly Leu Tyr Gln Gly
                325                 330                 335

Leu Ser Thr Ala Thr Lys Asp Thr Tyr Asp Ala Leu His Met Gln Ala
                340                 345                 350

Leu Pro Pro Arg
        355

<210> SEQ ID NO 50
<211> LENGTH: 301
<212> TYPE: PRT
<213> ORGANISM: Artificial Sequence
<220> FEATURE:
<223> OTHER INFORMATION: Made in Lab - anti-CLL1 VHH DARIC signaling
      component

<400> SEQUENCE: 50

Met Ala Leu Pro Val Thr Ala Leu Leu Leu Pro Leu Ala Leu Leu Leu
1               5                   10                  15

His Ala Ala Arg Pro Gly Ser Ile Leu Trp His Glu Met Trp His Glu
            20                  25                  30

Gly Leu Glu Glu Ala Ser Arg Leu Tyr Phe Gly Glu Arg Asn Val Lys
        35                  40                  45

Gly Met Phe Glu Val Leu Glu Pro Leu His Ala Met Met Glu Arg Gly
    50                  55                  60

Pro Gln Thr Leu Lys Glu Thr Ser Phe Asn Gln Ala Tyr Gly Arg Asp
65                  70                  75                  80

Leu Met Glu Ala Gln Glu Trp Cys Arg Lys Tyr Met Lys Ser Gly Asn
                85                  90                  95

Val Lys Asp Leu Leu Gln Ala Trp Asp Leu Tyr Tyr His Val Phe Arg
            100                 105                 110

Arg Ile Ser Lys Ala Ser Ala Gly Thr Gly Ser Asp Ile Tyr Ile Trp
        115                 120                 125

Ala Pro Leu Ala Gly Thr Cys Gly Val Leu Leu Leu Ser Leu Val Ile
    130                 135                 140

Thr Met His Lys Arg Gly Arg Lys Lys Leu Leu Tyr Ile Phe Lys Gln
145                 150                 155                 160

Pro Phe Met Arg Pro Val Gln Thr Thr Gln Glu Glu Asp Gly Cys Ser
                165                 170                 175

Cys Arg Phe Pro Glu Glu Glu Glu Gly Gly Cys Glu Leu Arg Val Lys
            180                 185                 190

Phe Ser Arg Ser Ala Asp Ala Pro Ala Tyr Gln Gln Gly Gln Asn Gln
        195                 200                 205

```
Leu Tyr Asn Glu Leu Asn Leu Gly Arg Arg Glu Glu Tyr Asp Val Leu
        210                 215                 220

Asp Lys Arg Arg Gly Arg Asp Pro Glu Met Gly Gly Lys Pro Arg Arg
225                 230                 235                 240

Lys Asn Pro Gln Glu Gly Leu Tyr Asn Glu Leu Gln Lys Asp Lys Met
                    245                 250                 255

Ala Glu Ala Tyr Ser Glu Ile Gly Met Lys Gly Glu Arg Arg Arg Gly
            260                 265                 270

Lys Gly His Asp Gly Leu Tyr Gln Gly Leu Ser Thr Ala Thr Lys Asp
            275                 280                 285

Thr Tyr Asp Ala Leu His Met Gln Ala Leu Pro Pro Arg
        290                 295                 300

<210> SEQ ID NO 51
<211> LENGTH: 10
<212> TYPE: DNA
<213> ORGANISM: Artificial Sequence
<220> FEATURE:
<223> OTHER INFORMATION: Consensus Kozak sequence

<400> SEQUENCE: 51 gccrccatgg                                                            10

<210> SEQ ID NO 52
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 52

Asp Gly Gly Gly Ser
1               5

<210> SEQ ID NO 53
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 53

Thr Gly Glu Lys Pro
1               5

<210> SEQ ID NO 54
<211> LENGTH: 4
<212> TYPE: PRT
<213> ORGANISM: Artificial Sequence
<220> FEATURE:
<223> OTHER INFORMATION: Exemplary linker sequence

<400> SEQUENCE: 54

Gly Gly Arg Arg
1

<210> SEQ ID NO 55
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 55
```

Gly Gly Gly Gly Ser
1               5

<210> SEQ ID NO 56
<211> LENGTH: 14
<212> TYPE: PRT
<213> ORGANISM: Artificial Sequence
<220> FEATURE:
<223> OTHER INFORMATION: Exemplary linker sequence

<400> SEQUENCE: 56

Glu Gly Lys Ser Ser Gly Ser Gly Ser Glu Ser Lys Val Asp
1               5                   10

<210> SEQ ID NO 57
<211> LENGTH: 18
<212> TYPE: PRT
<213> ORGANISM: Artificial Sequence
<220> FEATURE:
<223> OTHER INFORMATION: Exemplary linker sequence

<400> SEQUENCE: 57

Lys Glu Ser Gly Ser Val Ser Ser Glu Gln Leu Ala Gln Phe Arg Ser
1               5                   10                  15

Leu Asp

<210> SEQ ID NO 58
<211> LENGTH: 8
<212> TYPE: PRT
<213> ORGANISM: Artificial Sequence
<220> FEATURE:
<223> OTHER INFORMATION: Exemplary linker sequence

<400> SEQUENCE: 58

Gly Gly Arg Arg Gly Gly Gly Ser
1               5

<210> SEQ ID NO 59
<211> LENGTH: 9
<212> TYPE: PRT
<213> ORGANISM: Artificial Sequence
<220> FEATURE:
<223> OTHER INFORMATION: Exemplary linker sequence

<400> SEQUENCE: 59

Leu Arg Gln Arg Asp Gly Glu Arg Pro
1               5

<210> SEQ ID NO 60
<211> LENGTH: 12
<212> TYPE: PRT
<213> ORGANISM: Artificial Sequence
<220> FEATURE:
<223> OTHER INFORMATION: Exemplary linker sequence

<400> SEQUENCE: 60

Leu Arg Gln Lys Asp Gly Gly Gly Ser Glu Arg Pro
1               5                   10

<210> SEQ ID NO 61
<211> LENGTH: 16
<212> TYPE: PRT
<213> ORGANISM: Artificial Sequence
<220> FEATURE:
<223> OTHER INFORMATION: Exemplary linker sequence

```
<400> SEQUENCE: 61

Leu Arg Gln Lys Asp Gly Gly Ser Gly Gly Gly Ser Glu Arg Pro
1               5                   10                  15

<210> SEQ ID NO 62
<211> LENGTH: 18
<212> TYPE: PRT
<213> ORGANISM: Artificial Sequence
<220> FEATURE:
<223> OTHER INFORMATION: Exemplary linker sequence

<400> SEQUENCE: 62

Gly Ser Thr Ser Gly Ser Gly Lys Pro Gly Ser Gly Glu Gly Ser Thr
1               5                   10                  15

Lys Gly

<210> SEQ ID NO 63
<211> LENGTH: 7
<212> TYPE: PRT
<213> ORGANISM: Artificial Sequence
<220> FEATURE:
<223> OTHER INFORMATION: Cleavage sequence by TEV protease
<220> FEATURE:
<221> NAME/KEY: misc_feature
<222> LOCATION: (2)..(3)
<223> OTHER INFORMATION: Xaa is any amino acid
<220> FEATURE:
<221> NAME/KEY: misc_feature
<222> LOCATION: (5)..(5)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa = Gly or Ser

<400> SEQUENCE: 63

Glu Xaa Xaa Tyr Xaa Gln Xaa
1               5

<210> SEQ ID NO 64
<211> LENGTH: 7
<212> TYPE: PRT
<213> ORGANISM: Artificial Sequence
<220> FEATURE:
<223> OTHER INFORMATION: Cleavage sequence by TEV protease

<400> SEQUENCE: 64

Glu Asn Leu Tyr Phe Gln Gly
1               5

<210> SEQ ID NO 65
<211> LENGTH: 7
<212> TYPE: PRT
<213> ORGANISM: Artificial Sequence
<220> FEATURE:
<223> OTHER INFORMATION: Cleavage sequence by TEV protease

<400> SEQUENCE: 65

Glu Asn Leu Tyr Phe Gln Ser
1               5

<210> SEQ ID NO 66
<211> LENGTH: 22
<212> TYPE: PRT
<213> ORGANISM: Artificial Sequence
<220> FEATURE:
<223> OTHER INFORMATION: Self-cleaving polypeptide comprising 2A site
```

```
<400> SEQUENCE: 66

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 67
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 67

Ala Thr Asn Phe Ser Leu Leu Lys Gln Ala Gly Asp Val Glu Glu Asn
1               5                   10                  15

Pro Gly Pro

<210> SEQ ID NO 68
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 68

Leu Leu Lys Gln Ala Gly Asp Val Glu Glu Asn Pro Gly Pro
1               5                   10

<210> SEQ ID NO 69
<211> LENGTH: 21
<212> TYPE: PRT
<213> ORGANISM: Artificial Sequence
<220> FEATURE:
<223> OTHER INFORMATION: Self-cleaving polypeptide comprising 2A site

<400> SEQUENCE: 69

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 70
<211> LENGTH: 18
<212> TYPE: PRT
<213> ORGANISM: Artificial Sequence
<220> FEATURE:
<223> OTHER INFORMATION: Self-cleaving polypeptide comprising 2A site

<400> SEQUENCE: 70

Glu Gly Arg Gly Ser Leu Leu Thr Cys Gly Asp Val Glu Glu Asn Pro
1               5                   10                  15

Gly Pro

<210> SEQ ID NO 71
<211> LENGTH: 13
<212> TYPE: PRT
<213> ORGANISM: Artificial Sequence
<220> FEATURE:
<223> OTHER INFORMATION: Self-cleaving polypeptide comprising 2A site

<400> SEQUENCE: 71

Leu Leu Thr Cys Gly Asp Val Glu Glu Asn Pro Gly Pro
1               5                   10
```

```
<210> SEQ ID NO 72
<211> LENGTH: 23
<212> TYPE: PRT
<213> ORGANISM: Artificial Sequence
<220> FEATURE:
<223> OTHER INFORMATION: Self-cleaving polypeptide comprising 2A site

<400> SEQUENCE: 72

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 73
<211> LENGTH: 20
<212> TYPE: PRT
<213> ORGANISM: Artificial Sequence
<220> FEATURE:
<223> OTHER INFORMATION: Self-cleaving polypeptide comprising 2A site

<400> SEQUENCE: 73

Gln Cys Thr Asn Tyr Ala Leu Leu Lys Leu Ala Gly Asp Val Glu Ser
1               5                   10                  15

Asn Pro Gly Pro
            20

<210> SEQ ID NO 74
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 74

Leu Leu Lys Leu Ala Gly Asp Val Glu Ser Asn Pro Gly Pro
1               5                   10

<210> SEQ ID NO 75
<211> LENGTH: 25
<212> TYPE: PRT
<213> ORGANISM: Artificial Sequence
<220> FEATURE:
<223> OTHER INFORMATION: Self-cleaving polypeptide comprising 2A site

<400> SEQUENCE: 75

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 76
<211> LENGTH: 22
<212> TYPE: PRT
<213> ORGANISM: Artificial Sequence
<220> FEATURE:
<223> OTHER INFORMATION: Self-cleaving polypeptide comprising 2A site

<400> SEQUENCE: 76

Val Lys Gln Thr Leu Asn Phe Asp Leu Leu Lys Leu Ala Gly Asp Val
1               5                   10                  15

Glu Ser Asn Pro Gly Pro
            20
```

```
<210> SEQ ID NO 77
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 77

Leu Leu Lys Leu Ala Gly Asp Val Glu Ser Asn Pro Gly Pro
1               5                   10

<210> SEQ ID NO 78
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 78

Leu Leu Asn Phe Asp Leu Leu Lys Leu Ala Gly Asp Val Glu Ser Asn
1               5                   10                  15

Pro Gly Pro

<210> SEQ ID NO 79
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 79

Thr Leu Asn Phe Asp Leu Leu Lys Leu Ala Gly Asp Val Glu Ser Asn
1               5                   10                  15

Pro Gly Pro

<210> SEQ ID NO 80
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 80

Leu Leu Lys Leu Ala Gly Asp Val Glu Ser Asn Pro Gly Pro
1               5                   10

<210> SEQ ID NO 81
<211> LENGTH: 17
<212> TYPE: PRT
<213> ORGANISM: Artificial Sequence
<220> FEATURE:
<223> OTHER INFORMATION: Self-cleaving polypeptide comprising 2A site

<400> SEQUENCE: 81

Asn Phe Asp Leu Leu Lys Leu Ala Gly Asp Val Glu Ser Asn Pro Gly
1               5                   10                  15

Pro

<210> SEQ ID NO 82
<211> LENGTH: 20
<212> TYPE: PRT
<213> ORGANISM: Artificial Sequence
<220> FEATURE:
<223> OTHER INFORMATION: Self-cleaving polypeptide comprising 2A site

<400> SEQUENCE: 82
```

```
Gln Leu Leu Asn Phe Asp Leu Leu Lys Leu Ala Gly Asp Val Glu Ser
1               5                   10                  15

Asn Pro Gly Pro
            20

<210> SEQ ID NO 83
<211> LENGTH: 24
<212> TYPE: PRT
<213> ORGANISM: Artificial Sequence
<220> FEATURE:
<223> OTHER INFORMATION: Self-cleaving polypeptide comprising 2A site

<400> SEQUENCE: 83

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 84
<211> LENGTH: 40
<212> TYPE: PRT
<213> ORGANISM: Artificial Sequence
<220> FEATURE:
<223> OTHER INFORMATION: Self-cleaving polypeptide comprising 2A site

<400> SEQUENCE: 84

Val Thr Glu Leu Leu Tyr Arg Met Lys Arg Ala Glu Thr Tyr Cys Pro
1               5                   10                  15

Arg Pro Leu Leu Ala Ile His Pro Thr Glu Ala Arg His Lys Gln Lys
            20                  25                  30

Ile Val Ala Pro Val Lys Gln Thr
        35                  40

<210> SEQ ID NO 85
<211> LENGTH: 18
<212> TYPE: PRT
<213> ORGANISM: Artificial Sequence
<220> FEATURE:
<223> OTHER INFORMATION: Self-cleaving polypeptide comprising 2A site

<400> SEQUENCE: 85

Leu Asn Phe Asp Leu Leu Lys Leu Ala Gly Asp Val Glu Ser Asn Pro
1               5                   10                  15

Gly Pro

<210> SEQ ID NO 86
<211> LENGTH: 40
<212> TYPE: PRT
<213> ORGANISM: Artificial Sequence
<220> FEATURE:
<223> OTHER INFORMATION: Self-cleaving polypeptide comprising 2A site

<400> SEQUENCE: 86

Leu Leu Ala Ile His Pro Thr Glu Ala Arg His Lys Gln Lys Ile Val
1               5                   10                  15

Ala Pro Val Lys Gln Thr Leu Asn Phe Asp Leu Leu Lys Leu Ala Gly
            20                  25                  30

Asp Val Glu Ser Asn Pro Gly Pro
        35                  40

<210> SEQ ID NO 87
<211> LENGTH: 33
```

```
-continued

<212> TYPE: PRT
<213> ORGANISM: Artificial Sequence
<220> FEATURE:
<223> OTHER INFORMATION: Self-cleaving polypeptide comprising 2A site

<400> SEQUENCE: 87

Glu Ala Arg His Lys Gln Lys Ile Val Ala Pro Val Lys Gln Thr Leu
1               5                   10                  15

Asn Phe Asp Leu Leu Lys Leu Ala Gly Asp Val Glu Ser Asn Pro Gly
            20                  25                  30

Pro
```

CLL-1 TARGETED IMMUNOTHERAPIES

CROSS REFERENCE TO RELATED APPLICATIONS

This application is a National Stage application under 35 U.S.C. § 371 of International Application No. PCT/US2020/031781, filed May 7, 2020, which claims the benefit under 35 U.S.C. § 119(e) of U.S. Provisional Application No. 62/845,306, filed May 8, 2019, which is incorporated by reference herein in its entirety.

STATEMENT REGARDING SEQUENCE LISTING

The Sequence Listing associated with this application is provided in text format in lieu of a paper copy and is hereby incorporated by reference into the specification. The name of the text file containing the Sequence Listing is BLBD_120_01WO_ST25.txt. The text file is 187 KB, was created on May 5, 2020, and is being submitted electronically via EFS-Web, concurrent with the filing of the specification.

BACKGROUND

Technical Field

The present disclosure relates to improved adoptive cell therapies directed against C-type lectin-like molecule-1 (CLL-1). More particularly, the disclosure relates to anti-CLL-1 VHH-containing chemically regulated signaling molecules, anti-CLL-1 VHH-containing chimeric antigen receptors, cells, and related methods of treatment using the same.

Description of the Related Art

The global burden of cancer doubled between 1975 and 2000. Cancer is the second leading cause of morbidity and mortality worldwide, with approximately 14.1 million new cases and 8.2 million cancer related deaths in 2012. The most common cancers are breast cancer, lung and bronchus cancer, prostate cancer, colon and rectum cancer, bladder cancer, melanoma of the skin, non-Hodgkin lymphoma, thyroid cancer, kidney and renal pelvis cancer, endometrial cancer, leukemia, and pancreatic cancer. The number of new cancer cases is projected to rise to 22 million within the next two decades.

Adoptive cellular therapy is emerging as a powerful paradigm for delivering complex biological signals to treat cancer. In contrast to small molecule and biologic drug compositions, adoptive cell therapies have the potential to execute unique therapeutic tasks owing to their myriad sensory and response programs and increasingly defined mechanisms of genetic control. Existing methods have focused primarily on scFv-based chimeric antigen receptors (CARs). CAR T cell therapy has met with limited success due to poor CAR expression, in vivo expansion of CAR T cells, rapid disappearance of the cells after infusion, disappointing clinical activity, and antigen escape.

There is a need to retrofit immune effector cells with improved CAR architectures (CARchitectures) and/or improved machinery for sensing and integrating chemical and/or biological information associated with local physiological environments.

BRIEF SUMMARY

The present disclosure generally relates, in part, to VHH-based dimerizing agent regulated immunoreceptor complexes (DARICs) and VHH-based chimeric antigen receptors (CARs) directed against CLL-1, polynucleotides encoding the same, compositions thereof, and methods of making and using the same to treat cancer.

In various embodiments, a non-natural cell comprises: a first polypeptide comprising: an FRB multimerization domain polypeptide or variant thereof, a CD8a transmembrane domain or a CD4 transmembrane domain; a CD137 co-stimulatory domain; and/or a CD3ζ primary signaling domain; and a second polypeptide comprising: an anti-CLL-1 VHH antibody that has an amino acid sequence set forth in any one of SEQ ID NOs: 2-13; an FKBP multimerization domain polypeptide or variant thereof, and a CD4 transmembrane domain or a CD8a transmembrane domain; wherein a bridging factor promotes the formation of a polypeptide complex on the non-natural cell surface with the bridging factor associated with and disposed between the multimerization domains of the first and second polypeptides.

In particular embodiments, the FKBP multimerization domain is FKBP12.

In some embodiments, the FRB polypeptide is FRB T2098L.

In certain embodiments, the bridging factor is selected from the group consisting of: AP21967, sirolimus, everolimus, novolimus, pimecrolimus, ridaforolimus, tacrolimus, temsirolimus, umirolimus, and zotarolimus.

In various embodiments, the first polypeptide comprises a signal peptide, a CD8a transmembrane domain; a CD137 co-stimulatory domain; and a CD3ζ primary signaling domain.

In particular embodiments, the second polypeptide comprises a signal peptide and a CD4 transmembrane domain.

In further embodiments, the second polypeptide comprises a costimulatory domain.

In some embodiments, the costimulatory domain of the second polypeptide is selected from a costimulatory molecule selected from the group consisting of: Toll-like receptor 1 (TLR1), TLR2, TLR3, TLR4, TLR5, TLR6, TLR7, TLR8, TLR9, TLR10, caspase recruitment domain family member 11 (CARD 11), CD2, CD7, CD27, CD28, CD30, CD40, CD54 (ICAM), CD83, CD94, CD134 (OX40), CD137 (4-1BB), CD278 (ICOS), DNAX-Activation Protein 10 (DAP10), Linker for activation of T-cells family member 1 (LAT), SH2 Domain-Containing Leukocyte Protein Of 76 kD (SLP76), T cell receptor associated transmembrane adaptor 1 (TRAT1), TNFR2, TNFRS14, TNFRS18, TNRFS25, and zeta chain of T cell receptor associated protein kinase 70 (ZAP70).

In additional embodiments, the costimulatory domain of the second polypeptide is a costimulatory domain isolated from OX40 or TNFR2.

In further embodiments, the second polypeptide comprises the sequence set forth in any one of SEQ ID NOs: 14-19.

In preferred embodiments, a first polypeptide comprises an amino acid sequence set forth in SEQ ID NO 50.

In various embodiments, a non-natural cell comprises a polypeptide complex that comprises: a first polypeptide comprising: an FRB multimerization domain polypeptide or variant thereof, a CD8a transmembrane domain or a CD4 transmembrane domain; a CD137 co-stimulatory domain; and/or a CD3ζ primary signaling domain; a second polypeptide comprising: an anti-CLL-1 VHH antibody that has an amino acid sequence set forth in any one of SEQ ID NOs: 2-13; an FKBP multimerization domain polypeptide or variant thereof; and a CD4 transmembrane domain or a CD8a transmembrane domain; and a bridging factor associated with and disposed between the multimerization domains of the first and second polypeptides.

In particular embodiments, the FKBP multimerization domain is FKBP12.

In certain embodiments, the FRB polypeptide is FRB T2098L.

In some embodiments, the bridging factor is selected from the group consisting of: AP21967, sirolimus, everolimus, novolimus, pimecrolimus, ridaforolimus, tacrolimus, temsirolimus, umirolimus, and zotarolimus.

In additional embodiments, the first polypeptide comprises a signal peptide, a CD8a transmembrane domain; a CD137 co-stimulatory domain; and a CD3ζ primary signaling domain.

In particular embodiments, the second polypeptide comprises a signal peptide and a CD4 transmembrane domain.

In some embodiments, the second polypeptide comprises a costimulatory domain.

In various embodiments, the costimulatory domain of the second polypeptide is selected from a costimulatory molecule selected from the group consisting of: Toll-like receptor 1 (TLR1), TLR2, TLR3, TLR4, TLR5, TLR6, TLR7, TLR8, TLR9, TLR10, caspase recruitment domain family member 11 (CARD 11), CD2, CD7, CD27, CD28, CD30, CD40, CD54 (ICAM), CD83, CD94, CD134 (OX40), CD137 (4-1BB), CD278 (ICOS), DNAX-Activation Protein 10 (DAP10), Linker for activation of T-cells family member 1 (LAT), SH2 Domain-Containing Leukocyte Protein Of 76 kD (SLP76), T cell receptor associated transmembrane adaptor 1 (TRAT1), TNFR2, TNFRS14, TNFRS18, TNRFS25, and zeta chain of T cell receptor associated protein kinase 70 (ZAP70).

In additional embodiments, the costimulatory domain of the second polypeptide is a costimulatory domain isolated from OX40 or TNFR2.

In further embodiments, the second polypeptide comprises the sequence set forth in any one of SEQ ID NOs: 14-19.

In preferred embodiments, a first polypeptide comprises an amino acid sequence set forth in SEQ ID NO 50.

In certain embodiments, the cell is a hematopoietic cell.

In particular embodiments, the cell is a T cell, an ap T cell, or a T6 T cell.

In further embodiments, the cell is a CD3+, CD4+, and/or CD8+ cell.

In various embodiments, the cell is an immune effector cell.

In some embodiments, the cell is a cytotoxic T lymphocytes (CTLs), a tumor infiltrating lymphocytes (TILs), or a helper T cell.

In additional embodiments, the cell is a natural killer (NK) cell or natural killer T (NKT) cell.

In various embodiments, the source of the cell is peripheral blood mononuclear cells, bone marrow, lymph nodes tissue, cord blood, thymus issue, tissue from a site of infection, ascites, pleural effusion, spleen tissue, or tumors.

In particular embodiments, the FRB multimerization domain and the FKBP multimerization domain localize extracellularly when of the first polypeptide and the second polypeptide are expressed.

In some embodiments, a fusion polypeptide comprises: a first polypeptide comprising: an FRB multimerization domain polypeptide or variant thereof; a CD8α transmembrane domain or a CD4 transmembrane domain; a CD137 co-stimulatory domain; and/or a CD3ζ primary signaling domain; a polypeptide cleavage signal; and a second polypeptide comprising: an anti-CLL-1 VHH antibody that has an amino acid sequence set forth in any one of SEQ ID NOs: 2-13; an FKBP multimerization domain polypeptide or variant thereof; and a CD4 transmembrane domain or a CD8α transmembrane domain.

In particular embodiments, the FKBP multimerization domain is FKBP12.

In certain embodiments, the FRB polypeptide is FRB T2098L.

In some embodiments, the bridging factor is selected from the group consisting of: AP21967, sirolimus, everolimus, novolimus, pimecrolimus, ridaforolimus, tacrolimus, temsirolimus, umirolimus, and zotarolimus.

In additional embodiments, the first polypeptide comprises a signal peptide, a CD8α transmembrane domain; a CD137 co-stimulatory domain; and a CD3ζ primary signaling domain.

In particular embodiments, the second polypeptide comprises a signal peptide and a CD4 transmembrane domain.

In certain embodiments, the fusion polypeptide comprises the sequence set forth in any one of SEQ ID NOs: 20-25.

In further embodiments, the second polypeptide comprises a costimulatory domain.

In various embodiments, the costimulatory domain of the second polypeptide is selected from a costimulatory molecule selected from the group consisting of: Toll-like receptor 1 (TLR1), TLR2, TLR3, TLR4, TLR5, TLR6, TLR7, TLR8, TLR9, TLR10, caspase recruitment domain family member 11 (CARD 11), CD2, CD7, CD27, CD28, CD30, CD40, CD54 (ICAM), CD83, CD94, CD134 (OX40), CD137 (4-1BB), CD278 (ICOS), DNAX-Activation Protein 10 (DAP10), Linker for activation of T-cells family member 1 (LAT), SH2 Domain-Containing Leukocyte Protein Of 76 kD (SLP76), T cell receptor associated transmembrane adaptor 1 (TRAT1), TNFR2, TNFRS14, TNFRS18, TNRFS25, and zeta chain of T cell receptor associated protein kinase 70 (ZAP70).

In additional embodiments, the costimulatory domain of the second polypeptide is a costimulatory domain isolated from OX40 or TNFR2.

In certain embodiments, the polypeptide cleavage signal is a viral self-cleaving polypeptide.

In particular embodiments, the polypeptide cleavage signal is a viral self-cleaving 2A polypeptide.

In various embodiments, the polypeptide cleavage signal is a viral self-cleaving polypeptide selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide.

In some embodiments, the fusion polypeptide comprises the sequence set forth in any one of SEQ ID NOs: 26-37.

In further embodiments, the FRB multimerization domain and the FKBP multimerization domain localize extracellularly when of the first polypeptide and the second polypeptide are expressed.

In various embodiments, polypeptide complex comprises: a first polypeptide comprising: an FRB multimerization domain polypeptide or variant thereof, a CD8α transmembrane domain or a CD4 transmembrane domain; a CD137 co-stimulatory domain; and/or a CD3ζ primary signaling domain; a second polypeptide comprising: an anti-CLL-1

VHH antibody that has an amino acid sequence set forth in any one of SEQ ID NOs: 2-13; an FKBP multimerization domain polypeptide or variant thereof, and a CD4 transmembrane domain or a CD8α transmembrane domain; and a bridging factor associated with and disposed between the multimerization domains of the first and second polypeptides.

In particular embodiments, the FKBP multimerization domain is FKBP12.

In additional embodiments, the FRB polypeptide is FRB T2098L.

In particular embodiments, the bridging factor is selected from the group consisting of: AP21967, sirolimus, everolimus, novolimus, pimecrolimus, ridaforolimus, tacrolimus, temsirolimus, umirolimus, and zotarolimus.

In certain embodiments, the first polypeptide comprises a CD8α transmembrane domain; a CD137 co-stimulatory domain; and a CD3ζ primary signaling domain.

In various embodiments, the second polypeptide comprises a CD4 transmembrane domain.

In further embodiments, the second polypeptide comprises a costimulatory domain.

In some embodiments, the costimulatory domain of the second polypeptide is selected from a costimulatory molecule selected from the group consisting of: Toll-like receptor 1 (TLR1), TLR2, TLR3, TLR4, TLR5, TLR6, TLR7, TLR8, TLR9, TLR10, caspase recruitment domain family member 11 (CARD 11), CD2, CD7, CD27, CD28, CD30, CD40, CD54 (ICAM), CD83, CD94, CD134 (OX40), CD137 (4-1BB), CD278 (ICOS), DNAX-Activation Protein 10 (DAP10), Linker for activation of T-cells family member 1 (LAT), SH2 Domain-Containing Leukocyte Protein Of 76 kD (SLP76), T cell receptor associated transmembrane adaptor 1 (TRAT1), TNFR2, TNFRS14, TNFRS18, TNRFS25, and zeta chain of T cell receptor associated protein kinase 70 (ZAP70).

In particular embodiments, the costimulatory domain of the second polypeptide is a costimulatory domain isolated from OX40 or TNFR2.

In certain embodiments, the cell is a hematopoietic cell.

In various embodiments, the cell is a T cell, an αβ T cell, or a TS T cell.

In various embodiments, the cell is a CD3+, CD4+, and/or CD8+ cell.

In additional embodiments, the cell is an immune effector cell.

In some embodiments, the cell is a cytotoxic T lymphocytes (CTLs), a tumor infiltrating lymphocytes (TILs), or a helper T cell.

In particular embodiments, the cell is a natural killer (NK) cell or natural killer T (NKT) cell.

In additional embodiments, the source of the cell is peripheral blood mononuclear cells, bone marrow, lymph nodes tissue, cord blood, thymus issue, tissue from a site of infection, ascites, pleural effusion, spleen tissue, or tumors.

In further embodiments, the FRB multimerization domain and the FKBP multimerization domain localize extracellularly when of the first polypeptide and the second polypeptide are expressed.

In preferred embodiments, a first polypeptide comprises an amino acid sequence set forth in SEQ ID NO 50.

In particular embodiments, a chimeric antigen receptor (CAR) comprises: an anti-CLL-1 VHH antibody that has an amino acid sequence set forth in any one of SEQ ID NOs: 2-13; a hinge domain; a transmembrane domain; one or more intracellular costimulatory signaling domains; and/or a primary signaling domain.

In various embodiments, the CAR comprises from 5' to 3': an anti-CLL-1 VHH antibody that has an amino acid sequence set forth in any one of SEQ ID NOs: 2-13; a hinge domain; a transmembrane domain; one or more intracellular costimulatory signaling domains; and/or a primary signaling domain.

In certain embodiments, the hinge domain and transmembrane domain are isolated from CD8a, CD27, CD28, CD33, CD37, CD45, CD64, CD71, CD80, CD86, CD 134, CD137, CD152, CD154, AMN, and PD1.

In additional embodiments, the one or more costimulatory signaling domains are isolated from a costimulatory molecule selected from the group consisting of: CD28, CD134, CD137, and CD278.

In particular embodiments, the CAR comprises a CD8α signal peptide, a CD8α hinge and transmembrane domain, a CD134 costimulatory domain, and a CD3ζ primary signaling domain.

In further embodiments, a CAR comprises the amino acid sequence set forth in any one of SEQ ID NOs: 38-49.

In some embodiments, polynucleotide encoding a first or second polypeptide, a fusion polypeptide, or a CAR contemplated herein is provided.

In various embodiments, a cDNA encoding a first or second polypeptide, a fusion polypeptide, or a CAR contemplated herein is provided.

In particular embodiments, an RNA encoding a first or second polypeptide, a fusion polypeptide, or a CAR contemplated herein is provided.

In additional embodiments, a vector comprising a polynucleotide contemplated herein is provided.

In certain embodiments, the vector is an expression vector.

In certain embodiments, the vector is a transposon.

In further embodiments, the vector is a piggyBAC transposon or a Sleeping Beauty transposon.

In particular embodiments, the vector is a viral vector.

In particular embodiments, the vector is an adenoviral vector, an adeno-associated viral (AAV) vector, a herpes virus vector, a vaccinia virus vector, or a retroviral vector.

In additional embodiments, the retroviral vector is a lentiviral vector.

In various embodiments, the lentiviral vector is selected from the group consisting of: human immunodeficiency virus 1 (HIV-1); human immunodeficiency virus 2 (HIV-2), visna-maedi virus (VMV) virus; caprine arthritis-encephalitis virus (CAEV); equine infectious anemia virus (EIAV); feline immunodeficiency virus (FIV); bovine immune deficiency virus (BIV); and simian immunodeficiency virus (SIV).

In further embodiments, a cell comprising a first and second polypeptide, a fusion polypeptide, or a CAR contemplated herein is provided.

In particular embodiments, the cell is a hematopoietic cell.

In certain embodiments, the cell is an immune effector cell.

In various embodiments, the cell is a T cell, an αβ T cell, or a γδ T cell.

In some embodiments, the cell expresses CD3+, CD4+, CD8+, or a combination thereof.

In particular embodiments, the cell is a cytotoxic T lymphocyte (CTL), a tumor infiltrating lymphocyte (TIL), or a helper T cell.

In further embodiments, the cell is a natural killer (NK) cell or natural killer T (NKT) cell.

In certain embodiments, a composition comprises a cell contemplated herein.

In particular embodiments, a composition comprises a physiologically acceptable carrier and a cell contemplated herein.

In additional embodiments, method of treating a subject in need thereof comprising administering the subject an effective amount of a composition contemplated herein.

In particular embodiments, a method of treating, preventing, or ameliorating at least one symptom of a cancer, infectious disease, autoimmune disease, inflammatory disease, and immunodeficiency, or condition associated therewith, comprises administering to the subject an effective amount of a composition contemplated herein.

In some embodiments, a method of treating a solid cancer comprises administering to the subject an effective amount of a composition contemplated herein.

In various embodiments, the solid cancer is selected from the group consisting of: lung cancer, liver cancer, gastric cancer, colorectal cancer, head and neck cancer, urothelial cancer, prostate cancer, testicular cancer, endometrial cancer, pancreatic cancer, breast cancer, cervical cancer, ovarian cancer, skin cancer, and melanoma.

In certain embodiments, a method of treating a hematological malignancy comprises administering to the subject an effective amount of a composition contemplated herein.

In various embodiments, the hematological malignancy is a leukemia, lymphoma, or multiple myeloma.

In particular embodiments, the hematological malignancy is acute myelogenous leukemia (AML).

BRIEF DESCRIPTION OF SEVERAL VIEWS OF THE DRAWINGS

FIG. 6A shows CLL-1 expression on THP-1 cells, THP-1 cells engineered to knock out the CLL-1 gene (CLL-1-KO cells), and in an unstained control.

FIG. 6B shows IFNγ secretion from UTD T cells or CLL-1 VHH DARIC T cells co-cultured with CD123 expressing THP-1 cells at an E:T ratio of 1:1 in the presence or absence of AP21967 for 24 hours.

FIG. 6C shows IFNγ secretion from UTD T cells or CLL-1 VHH DARIC T cells co-cultured with CLL-1-KO cells at an E:T ratio of 1:1 in the presence or absence of AP21967 for 24 hours.

BRIEF DESCRIPTION OF THE SEQUENCE IDENTIFIERS

Figures 1A, 1B:
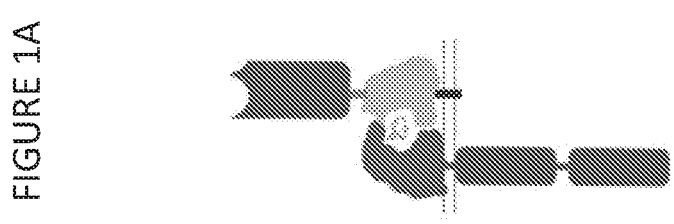
FIG. 1A shows a cartoon of a VHH-DARIC polypeptide complex.
FIG. 1B shows a cartoon of a CLL-1 VHH DARIC architecture.

SEQ ID NO: 1 sets forth the amino acid sequence for human CLL-1.

SEQ ID NOs: 2-13 set forth the amino acid sequences for an anti-CLL-1 VHH domains.

SEQ ID NOs: 14-19 set forth the amino acid sequences for anti-CLL-1 VHH DARIC binding components.

SEQ ID NOs: 20-25 set forth the amino acid sequences for anti-CLL-1 VHH DARIC fusion proteins.

SEQ ID NOs: 26-31 set forth the amino acid sequences for anti-CLL-1 VHH DARIC.OX40 fusion proteins.

SEQ ID NOs: 32-37 set forth the amino acid sequences for anti-CLL-1 VHH DARIC.TNFR2 fusion proteins.

SEQ ID NOs: 38-49 set forth the amino acid sequences for anti-CLL-1 VHH CARs.

SEQ ID NO: 50 sets forth the amino acid sequence for an anti-CLL-1 VHH DARIC signaling component.

SEQ ID NO: 51 sets forth the polynucleotide sequence for a Kozak sequence.

SEQ ID NOs: 52-62 set forth the amino acid sequences of various linkers.

SEQ ID NOs: 63-87 set forth the amino acid sequences of protease cleavage sites and self-cleaving polypeptide cleavage sites.

In the foregoing sequences, Xaa, if present, may refer to any amino acid or the absence of an amino acid. In preferred embodiments, XaaXaa refers to the amino acid sequence SS or KP.

DETAILED DESCRIPTION

A. Overview

Cancer is among the leading causes of death worldwide. About 10% of cancers are hematological malignancies, which includes leukemia, lymphomas, and myelomas. Acute myeloid leukemia (AML) is the most common and fatal hematological malignancy in adults. Despite major scientific discoveries and novel therapies over the past four decades, the treatment outcomes of AML, especially in the adult patient population remain dismal. Standard chemotherapies can induce complete remission in selected patients; however, a majority of patients eventually relapse and succumb to the disease. In 2012, the worldwide incidence of AML was about 351,965 and about 265,461 people died from AML.

C-type lectin-like molecule-1 (CLL-1) is a type II transmembrane glycoprotein, and its expression is restricted to myeloid cells, AML blasts, and leukemia stem cells (LSCs). CLL-1 expression is absent in hematopoietic stem cells (HSCs) and bone marrow stem cells. CLL-1 is also expressed on leukemic stem cell (LSC), which possesses the ability to indefinitely self-renew and produce plenty of daughter blast cells with a specific phenotype of CLL-1, CD123, CD44, CD96, CD90, CD32, CD25, and TIM-3, acting as one of most important reasons of leukemia relapse The disclosure generally relates to improved compositions and methods for regulating the spatial and temporal control of adoptive cell therapies using dimerizing agent regulated immunoreceptor complexes (DARICs) that bind CLL-1. Without wishing to be bound by any particular theory, DARIC compositions and methods contemplated herein provide numerous advantages over CAR T cell therapies existing in the art, including but not limited to, both spatial and temporal control over immune effector cell signal transduction binding and signaling activities. DARIC temporal control primes the DARIC machinery for signaling through bridging factor mediated association of a DARIC binding component to a DARIC signaling component. DARIC spatial control engages the signaling machinery through recognition of CLL-1 by the DARIC binding domain of the DARIC binding component. In this manner, DARIC immune effector cells become activated when both a target cell expressing CLL-1 and a bridging factor are present.

The disclosure also relates to improved anti-CLL-1 CAR architectures that overcome potential limitations of existing CAR T therapies including but not limited to tonic signaling or antigen independent signaling, poor expression and/or subtherapeutic activity.

In various embodiments, the disclosure contemplates anti-CLL-1 VHH DARICs or anti-CLL-1 VHH CARs that generate an anti-cancer response against cancers that express CLL-1, e.g., AML.

In particular embodiments, a DARIC includes a polypeptide (DARIC signaling component) that comprises a multimerization domain polypeptide or variant thereof, a transmembrane domain, a costimulatory domain; and/or a primary signaling domain; and a polypeptide (DARIC binding component) that comprises an anti-CLL-1 VHH, a multimerization domain polypeptide or variant thereof, a transmembrane domain; and optionally a costimulatory domain. In the presence of a bridging factor, the DARIC binding and signaling components associate with one another through the bridging factor to form a functionally active DARIC that targets cells expressing CLL-1.

In particular embodiments, the multimerization domains of the DARIC binding and DARIC signaling components are positioned extracellularly. Extracellular position of the multimerization domains provides numerous advantages over intracellular positioning including, but not limited to, more efficient positioning of the anti-CLL-1 VHH domain, higher temporal sensitivity to bridging factor regulation, and less toxicity due to ability to use non-immunosuppressive doses of particular bridging factors.

Polynucleotides encoding DARICs, DARIC binding components, and DARIC signaling components; DARIC binding components, DARIC signaling components, DARIC protein complexes, DARIC fusion proteins; cells comprising polynucleotides encoding DARICs, DARIC binding components, and DARIC signaling components and/or expressing the same; and methods of using the same to treat an immune disorder are contemplated herein.

Techniques for recombinant (i.e., engineered) DNA, peptide and oligonucleotide synthesis, immunoassays, tissue culture, transformation (e.g., electroporation, lipofection), enzymatic reactions, purification and related techniques and procedures may be generally performed as described in various general and more specific references in microbiology, molecular biology, biochemistry, molecular genetics, cell biology, virology and immunology as cited and discussed throughout the present specification. See, e.g., Sambrook et al., *Molecular Cloning: A Laboratory Manual,* 3d ed., Cold Spring Harbor Laboratory Press, Cold Spring Harbor, N.Y.; *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford Univ. Press USA, 1985); *Current Protocols in Immunology* (Edited by: John E. Coligan, Ada M. Kruisbeek, David H. Margulies, Ethan M. Shevach, Warren Strober 2001 John Wiley & Sons, NY, NY); *Real-Time PCR: Current Technology and Applications,* Edited by Julie Logan, Kirstin Edwards and Nick Saunders, 2009, Caister Academic Press, Norfolk, UK; Anand, *Techniques for the Analysis of Complex Genomes,* (Academic Press, New York, 1992); Guthrie and Fink, *Guide to Yeast Genetics and Molecular Biology* (Academic Press, New York, 1991); *Oligonucleotide Synthesis* (N. Gait, Ed., 1984); *Nucleic Acid The Hybridization* (B. Hames & S. Higgins, Eds., 1985); *Transcription and Translation* (B. Hames & S. Higgins, Eds., 1984); *Animal Cell Culture* (R. Freshney, Ed., 1986); Perbal, *A Practical Guide to Molecular Cloning* (1984); *Next-Generation Genome Sequencing* (Janitz, 2008 Wiley-VCH); *PCR Protocols (Methods in Molecular Biology)* (Park, Ed., 3rd Edition, 2010 Humana Press); *Immobilized Cells And Enzymes* (TRL Press, 1986); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies*, (Cold Spring Harbor Laboratory Press, Cold Spring Harbor, N.Y., 1998); *Immunochemical Methods In Cell And Molecular Biology* (Mayer and Walker, eds., Academic Press, London, 1987); *Handbook Of Experimental Immunology*, Volumes I-IV (D. M. Weir andCC Blackwell, eds., 1986); Roitt, *Essential Immunology,* 6th Edition, (Blackwell Scientific Publications, Oxford, 1988); *Current Protocols in Immunology* (Q. E. Coligan, A. M. Kruisbeek, D. H. Margulies, E. M. Shevach and W. Strober, eds., 1991); *Annual Review of Immunology*; as well as monographs in journals such as Advances in Immunology.

B. Definitions

Prior to setting forth this disclosure in more detail, it may be helpful to an understanding thereof to provide definitions of certain terms to be used herein.

Unless defined otherwise, all technical and scientific terms used herein have the same meaning as commonly understood by those of ordinary skill in the art to which the invention belongs. Although any methods and materials similar or equivalent to those described herein can be used in the practice or testing of particular embodiments, preferred embodiments of compositions, methods and materials are described herein. For the purposes of the present disclosure, the following terms are defined below.

The articles "a," "an," and "the" are used herein to refer to one or to more than one (i.e., to at least one, or to one or more) of the grammatical object of the article. By way of example, "an element" means one element or one or more elements.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

In one embodiment, a range, e.g., 1 to 5, about 1 to 5, or about 1 to about 5, refers to each numerical value encompassed by the range. For example, in one non-limiting and merely illustrative embodiment, the range "1 to 5" is equivalent to the expression 1, 2, 3, 4, 5; or 1.0, 1.5, 2.0, 2.5, 3.0, 3.5, 4.0, 4.5, or 5.0; or 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0.

As used herein, the term "substantially" refers to a quantity, level, value, number, frequency, percentage, dimension, size, amount, weight or length that is 80%, 85%, 90%, 91%, 92%, 93%, 94%, 95%, 96%, 97%, 98%, 99% or higher compared to a reference quantity, level, value, number, frequency, percentage, dimension, size, amount, weight or length. In one embodiment, "substantially the same" refers to a quantity, level, value, number, frequency, percentage, dimension, size, amount, weight or length that produces an effect, e.g., a physiological effect, that is approximately the same as a reference quantity, level, value, number, frequency, percentage, dimension, size, amount, weight or length.

Throughout this specification, unless the context requires otherwise, the words "comprise," "comprises," and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are present that materially affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment. Thus, the appearances of the foregoing phrases in various places throughout this specification are not necessarily all referring to the same embodiment. Furthermore, the particular features, structures, or characteristics may be combined in any suitable manner in one or more embodiments. It is also understood that the positive recitation of a feature in one embodiment, serves as a basis for excluding the feature in a particular embodiment.

An "antigen (Ag)" refers to a compound, composition, or substance that can stimulate the production of antibodies or a T cell response in an animal, including compositions (such as one that includes a cancer-specific protein) that are injected or absorbed into an animal. Exemplary antigens include but are not limited to lipids, carbohydrates, polysaccharides, glycoproteins, peptides, or nucleic acids. An antigen reacts with the products of specific humoral or cellular immunity, including those induced by heterologous antigens, such as the disclosed antigens.

A "target antigen" or "target antigen of interest" refers to a portion of CLL-1, that a binding domain contemplated herein, is designed to bind. In particular embodiments, the target antigen is an epitope of the amino acid sequence set forth in SEQ ID NO: 1.

"C-Type Lectin-Like Molecule 1," "CLL-1," or "CLL-1" is a member of the C-type lectin/C-type lectin-like domain (CTL/CTLD) superfamily. The gene encoding CLL-1 is located on chromosome 12. CLL-1 is also known as C-Type lectin domain family 12 member A (CLEC12A), myeloid inhibitory C-Type lectin-like receptor (MICL), dendritic cell-associated lectin 2 (DCAL-2, DCAL2), and CD371. The predominant isoform of CLL-1 is a 265-amino acid type II transmembrane protein with a calculated molecular mass of 31 kD. CLL-1 contains an N-terminal cytoplasmic tail with an immunoreceptor tyrosine-based inhibitory motif (ITIM), a transmembrane domain, a stalk/neck region, and a C-terminal C-type lectin domain (CTLD). CLL-1 can inhibit cellular activation through its cytoplasmic ITIM and negatively regulate granulocyte and monocyte function. Representative CLL-1 polynucleotide sequences include NM_001207010.1, NM_001300730.1, NM_138337.5, NM_201623.3, NM_201625.1, ENST00000304361, ENST00000350667, ENST00000355690, ENST00000396507, ENST00000434319, ENST00000449959, and ENST00000543839. Representative CLL-1 polypeptide sequences include Q5QGZ9, ENSP00000405244, ENSP00000345448, ENSP00000347916, ENSP00000302804, ENSP00000379764, XP_011518873.2, XP_006719099.1, NP_001193939.1, NP_612210.4, XP_011518872.1, XP_011518875.1, NP 001287659.1, XP_005253381.1, NP_963917.2, XP_006719096.1, and XP_006719098.1.

An "antibody" refers to a binding agent that is a polypeptide comprising at least a light chain or heavy chain immunoglobulin variable region which specifically recognizes and binds an epitope of an antigen, such as a lipid, carbohydrate, polysaccharide, glycoprotein, peptide, or nucleic acid containing an antigenic determinant, such as those recognized by an immune cell.

References to "$V_H$" or "VH" refer to the variable region of an immunoglobulin heavy chain or antigen binding fragments thereof.

A "heavy chain antibody" refers to an antibody that contains two $V_H$ domains and no light chains (Riechmann L. et al, *J. Immunol. Methods* 231:25-38 (1999); WO94/04678; WO94/25591; U.S. Pat. No. 6,005,079). A "camelid antibody" refers to an antibody isolated from a Camel, Alpaca, or Llama that contains two $V_H$ domains and no light chains.

A "$V_HH$," "$V_HH$ antibody," or "$V_HH$ domain" as used herein refers an antibody fragment that contains the smallest known antigen-binding unit of the variable region of a heavy chain antibody (Koch-Nolte, et al, *FASEB J.*, 21: 3490-3498 (2007)).

A "linker" refers to a plurality of amino acid residues between the various polypeptide domains added for appropriate spacing and conformation of the molecule. In particular embodiments, a linker separates one or more VHH domains, hinge domains, multimerization domains, transmembrane domains, co-stimulatory domains, and/or primary signaling domains.

Illustrated examples of linkers suitable for use in particular embodiments contemplated herein include, but are not limited to the following amino acid sequences: GGG; DGGGS (SEQ ID NO: 52); TGEKP (SEQ ID NO: 53) (see, e.g., Liu et al., PNAS 5525-5530 (1997)); GGRR (SEQ ID NO: 54) (Pomerantz et al. 1995, supra); (GGGGS)$_n$ wherein n=1, 2, 3, 4 or 5 (SEQ ID NO: 55) (Kim et al., PNAS 93, 1156-1160 (1996).); EGKSSGSGSESKVD (SEQ ID NO: 56) (Chaudhary et al., 1990, Proc. Natl. Acad. Sci. U.S.A. 87:1066-1070); KESGSVSSEQLAQFRSLD (SEQ ID NO: 57) (Bird et al., 1988, Science 242:423-426), GGRRGGGS (SEQ ID NO: 58); LRQRDGERP (SEQ ID NO: 59); LRQKDGGGSERP (SEQ ID NO: 60); LRQKD(GGGS)$_2$ ERP (SEQ ID NO: 61). Alternatively, flexible linkers can be rationally designed using a computer program capable of modeling both DNA-binding sites and the peptides themselves (Desjarlais & Berg, *PNAS* 90:2256-2260 (1993), *PNAS* 91:11099-11103 (1994) or by phage display methods. In one embodiment, the linker comprises the following amino acid sequence: GSTSGSGKPGSGEGSTKG (SEQ ID NO: 62) (Cooper et al., *Blood,* 101(4): 1637-1644 (2003)).

A "spacer domain," refers to a polypeptide that separates two domains. In one embodiment, a spacer domain moves a VHH domain away from the effector cell surface to enable proper cell/cell contact, antigen binding and activation (Patel et al., *Gene Therapy,* 1999; 6: 412-419). In particular embodiments, a spacer domain separates one or more VHH domains, multimerization domains, transmembrane domains, co-stimulatory domains, and/or primary signaling domains. The spacer domain may be derived either from a natural, synthetic, semi-synthetic, or recombinant source. In certain embodiments, a spacer domain is a portion of an immunoglobulin, including, but not limited to, one or more heavy chain constant regions, e.g., CH2 and CH3. The spacer domain can include the amino acid sequence of a naturally occurring immunoglobulin hinge region or an altered immunoglobulin hinge region.

A "hinge domain," refers to a polypeptide that plays a role in positioning the antigen binding domain away from the effector cell surface to enable proper cell/cell contact, antigen binding and activation. In particular embodiments, polypeptides may comprise one or more hinge domains between the binding domain and the multimerization domain, between the binding domain and the transmembrane domain (TM), or between the multimerization domain and the transmembrane domain. The hinge domain may be derived either from a natural, synthetic, semi-synthetic, or recombinant source. The hinge domain can include the amino acid sequence of a naturally occurring immunoglobulin hinge region or an altered immunoglobulin hinge region.

A "multimerization domain," as used herein, refers to a polypeptide that preferentially interacts or associates with another different polypeptide directly or via a bridging molecule, e.g., a chemically inducible dimerizer, wherein the interaction of different multimerization domains substantially contributes to or efficiently promotes multimerization (i.e., the formation of a dimer, trimer, or multipartite complex, which may be a homodimer, heterodimer, homotrimer, heterotrimer, homomultimer, heteromultimer). A multimerization domain may be derived either from a natural, synthetic, semi-synthetic, or recombinant source.

Illustrative examples of multimerization domains suitable for use in particular embodiments contemplated herein include an FK506 binding protein (FKBP) polypeptide or variants thereof, an FKBP-rapamycin binding (FRB) polypeptide or variants thereof, a calcineurin polypeptide or variants thereof, a cyclophilin polypeptide or variants thereof, a bacterial dihydrofolate reductase (DHFR) polypeptide or variants thereof, a PYRl-like 1 (PYL1) polypeptide or variants thereof, an abscisic acid insensitive 1 (ABI1) polypeptide or variants thereof, a GIB1 polypeptide or variants thereof, or a GAI polypeptide or variants thereof.

As used herein, the term "FKBP-rapamycin binding polypeptide" refers to an FRB polypeptide. In particular embodiments, the FRB polypeptide is an FKBP12-rapamycin binding polypeptide. FRB polypeptides suitable for use in particular embodiments contemplated herein generally contain at least about 85 to about 100 amino acid residues. In certain embodiments, the FRB polypeptide comprises a 93 amino acid sequence Ile-2021 through Lys-2113 and a mutation of T2098L, with reference to GenBank Accession No. L34075.1. An FRB polypeptide contemplated herein binds to an FKBP polypeptide through a bridging factor, thereby forming a ternary complex.

As used herein, the term "FK506 binding protein" refers to an FKBP polypeptide. In particular embodiments, the FKBP polypeptide is an FKBP12 polypeptide or an FKBP12 polypeptide comprising an F36V mutation. In certain embodiments, an FKBP domain may also be referred to as a "rapamycin binding domain". Information concerning the nucleotide sequences, cloning, and other aspects of various FKBP species is known in the art (see, e.g., Staendart et al., *Nature* 346:671, 1990 (human FKBP12); Kay, *Biochem. J.* 314:361, 1996). An FKBP polypeptide contemplated herein binds to an FRB polypeptide through a bridging factor, thereby forming a ternary complex.

A "bridging factor" refers to a molecule that associates with and that is disposed between two or more multimerization domains. In particular embodiments, multimerization domains substantially contribute to or efficiently promote formation of a polypeptide complex only in the presence of a bridging factor. In particular embodiments, multimerization domains do not contribute to or do not efficiently promote formation of a polypeptide complex in the absence of a bridging factor. Illustrative examples of bridging factors suitable for use in particular embodiments contemplated herein include, but are not limited to AP21967, rapamycin (sirolimus) or a rapalog thereof, coumermycin or a derivative thereof, gibberellin or a derivative thereof, abscisic acid (ABA) or a derivative thereof, methotrexate or a derivative thereof, cyclosporin A or a derivative thereof, FKCsA or a derivative thereof, trimethoprim (Tmp)-synthetic ligand for FKBP (SLF) or a derivative thereof, or any combination thereof.

Rapamycin analogs (rapalogs) include, but are not limited to, those disclosed in U.S. Pat. No. 6,649,595, which rapalog structures are incorporated herein by reference in their entirety. In certain embodiments, a bridging factor is a rapalog with substantially reduced immunosuppressive effect as compared to rapamycin. In a preferred embodiment, the rapalog is AP21967 (also known as C-16-(S)-7-methylindolerapamycin, IC$_{50}$=10 nM, a chemically modified non-immunosuppressive rapamycin analogue). Other illustrative rapalogs suitable for use in particular embodiments contemplated herein include, but are not limited to, everolimus, novolimus, pimecrolimus, ridaforolimus, tacrolimus, temsirolimus, umirolimus, and zotarolimus.

A "substantially reduced immunosuppressive effect" refers to at least less than 0.1 to 0.005 times the immunosuppressive effect observed or expected for the same dose measured either clinically or in an appropriate in vitro (e.g., inhibition of T cell proliferation) or in vivo surrogate of human immunosuppressive activity.

A "transmembrane domain" or "TM domain" is a domain that anchors a polypeptide to the plasma membrane of a cell. The TM domain may be derived either from a natural, synthetic, semi-synthetic, or recombinant source.

The term "effector function" or "effector cell function" refers to a specialized function of an immune effector cell. Effector function includes, but is not limited to, activation, cytokine production, proliferation and cytotoxic activity, including the release of cytotoxic factors, or other cellular responses elicited with antigen binding to the receptor expressed on the immune effector cell.

An "intracellular signaling domain" or "endodomain" refers to the portion of a protein which transduces the effector function signal and that directs the cell to perform a specialized function. While usually the entire intracellular signaling domain can be employed, in many cases it is not necessary to use the entire domain. To the extent that a truncated portion of an intracellular signaling domain is used, such truncated portion may be used in place of the entire domain as long as it transduces an effector function signal. The term intracellular signaling domain is meant to include any truncated portion of an intracellular signaling domain necessary or sufficient to transduce an effector function signal.

It is known that signals generated through the TCR alone are insufficient for full activation of the T cell and that a secondary or co-stimulatory signal is also required. Thus, T cell activation can be said to be mediated by two distinct classes of intracellular signaling domains: primary signaling domains that initiate antigen-dependent primary activation through the TCR (e.g., a TCR/CD3 complex) and co-stimulatory signaling domains that act in an antigen-independent manner to provide a secondary or co-stimulatory signal.

A "primary signaling domain" refers to an intracellular signaling domain that regulates the primary activation of the TCR complex either in a stimulatory way, or in an inhibitory way. Primary signaling domains that act in a stimulatory manner may contain signaling motifs which are known as immunoreceptor tyrosine-based activation motifs or ITAMs. Illustrative examples of ITAM containing primary signaling domains that are suitable for use in particular embodiments include, but are not limited to those derived from FcRγ, FcRβ, CD3γ, CD3δ, CD3ε, CD3ζ, CD22, CD79a, CD79b, and CD66d.

As used herein, the term, "co-stimulatory signaling domain," or "co-stimulatory domain" refers to an intracellular signaling domain of a co-stimulatory molecule. Co-stimulatory molecules are cell surface molecules other than antigen receptors or Fc receptors that provide a second signal required for efficient activation and function of T lymphocytes upon binding to antigen. Illustrative examples of such co-stimulatory molecules from which co-stimulatory domains may be isolated include, but are not limited to: Toll-like receptor 1 (TLR1), TLR2, TLR3, TLR4, TLR5, TLR6, TLR7, TLR8, TLR9, TLR10, caspase recruitment domain family member 11 (CARD 11), CD2, CD7, CD27, CD28, CD30, CD40, CD54 (ICAM), CD83, CD94, CD134 (OX40), CD137 (4-1BB), CD278 (ICOS), DNAX-Activation Protein 10 (DAP10), Linker for activation of T-cells family member 1 (LAT), SH2 Domain-Containing Leukocyte Protein Of 76 kD (SLP76), T cell receptor associated transmembrane adaptor 1 (TRAT1), TNFR2, TNF receptor superfamily member 14 (TNFRS14; HVEM), TNF receptor superfamily member 18 (TNFRS18; GITR), TNF receptor superfamily member 25 (TNFRS25; DR3), and zeta chain of T cell receptor associated protein kinase 70 (ZAP70).

An "immune disorder" refers to a disease that evokes a response from the immune system. In particular embodiments, the term "immune disorder" refers to a cancer, an autoimmune disease, or an immunodeficiency.

As used herein, the term "cancer" relates generally to a class of diseases or conditions in which abnormal cells divide without control and can invade nearby tissues.

As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor.

As used herein, the term "benign" or "non-malignant" refers to tumors that may grow larger but do not spread to other parts of the body. Benign tumors are self-limited and typically do not invade or metastasize.

A "cancer cell" refers to an individual cell of a cancerous growth or tissue. Cancer cells include both solid cancers and liquid cancers. A "tumor" or "tumor cell" refers generally to a swelling or lesion formed by an abnormal growth of cells, which may be benign, pre-malignant, or malignant. Most cancers form tumors, but liquid cancers, e.g., leukemia, do not necessarily form tumors. For those cancers that form tumors, the terms cancer (cell) and tumor (cell) are used interchangeably. The amount of a tumor in an individual is the "tumor burden" which can be measured as the number, volume, or weight of the tumor.

The term "relapse" refers to the diagnosis of return, or signs and symptoms of return, of a cancer after a period of improvement or remission.

"Remission," is also referred to as "clinical remission," and includes both partial and complete remission. In partial remission, some, but not all, signs and symptoms of cancer have disappeared. In complete remission, all signs and symptoms of cancer have disappeared, although cancer still may be in the body.

"Refractory" refers to a cancer that is resistant to, or non-responsive to, therapy with a particular therapeutic agent. A cancer can be refractory from the onset of treatment (i.e., non-responsive to initial exposure to the therapeutic agent), or as a result of developing resistance to the therapeutic agent, either over the course of a first treatment period or during a subsequent treatment period.

As used herein, the terms "individual" and "subject" are often used interchangeably and refer to any animal that exhibits a symptom of cancer or other immune disorder that can be treated with the compositions and methods contemplated elsewhere herein. Suitable subjects (e.g., patients) include laboratory animals (such as mouse, rat, rabbit, or guinea pig), farm animals, and domestic animals or pets (such as a cat or dog). Non-human primates and, preferably, human patients, are included. Typical subjects include human patients that have, have been diagnosed with, or are at risk or having, cancer or another immune disorder.

As used herein, the term "patient" refers to a subject that has been diagnosed with cancer or another immune disorder that can be treated with the compositions and methods disclosed elsewhere herein.

As used herein "treatment" or "treating," includes any beneficial or desirable effect on the symptoms or pathology of a disease or pathological condition, and may include even minimal reductions in one or more measurable markers of the disease or condition being treated. Treatment can involve optionally either the reduction of the disease or condition, or the delaying of the progression of the disease or condition, e.g., delaying tumor outgrowth. "Treatment" does not necessarily indicate complete eradication or cure of the disease or condition, or associated symptoms thereof.

As used herein, "prevent," and similar words such as "prevented," "preventing" etc., indicate an approach for preventing, inhibiting, or reducing the likelihood of the occurrence or recurrence of, a disease or condition. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

As used herein, the phrase "ameliorating at least one symptom of" refers to decreasing one or more symptoms of the disease or condition for which the subject is being treated. In particular embodiments, the disease or condition being treated is a cancer, wherein the one or more symptoms ameliorated include, but are not limited to, weakness, fatigue, shortness of breath, easy bruising and bleeding, frequent infections, enlarged lymph nodes, distended or painful abdomen (due to enlarged abdominal organs), bone or joint pain, fractures, unplanned weight loss, poor appetite, night sweats, persistent mild fever, and decreased urination (due to impaired kidney function).

By "enhance" or "promote," or "increase" or "expand" refers generally to the ability of a composition contemplated herein to produce, elicit, or cause a greater physiological response (i.e., downstream effects) compared to the response caused by either vehicle or a control molecule/composition. A measurable physiological response may include an increase in T cell expansion, activation, persistence, cytokine secretion, and/or an increase in cancer cell killing ability, among others apparent from the understanding in the art and the description herein. An "increased" or "enhanced" amount is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle or a control composition.

By "decrease" or "lower," or "lessen," or "reduce," or "abate" refers generally to the ability of composition contemplated herein to produce, elicit, or cause a lesser physiological response (i.e., downstream effects) compared to the response caused by either vehicle or a control molecule/composition. A "decrease" or "reduced" amount is typically a "statistically significant" amount, and may include a decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response (reference response) produced by vehicle, a control composition, or the response in a particular cell lineage.

By "maintain," or "preserve," or "maintenance," or "no change," or "no substantial change," or "no substantial decrease" refers generally to the ability of a composition contemplated herein to produce, elicit, or cause a substantially similar or comparable physiological response (i.e., downstream effects) in a cell, as compared to the response caused by either vehicle, a control molecule/composition, or the response in a particular cell lineage. A comparable response is one that is not significantly different or measurable different from the reference response.

Additional definitions are set forth throughout this disclosure.

C. CLL-1 VHH DARICs

In particular embodiments, a DARIC receptor comprising an anti-CLL-1 VHH domain that redirects cytotoxicity of immune effector cells toward cancer cells expressing CLL-1 is contemplated. As used herein, the terms "CLL-1 VHH DARIC receptor," "anti-CLL-1 VHH DARIC receptor," "CLL-1 VHH DARIC," or "anti-CLL-1 VHH DARIC" are used interchangeably and refer to one or more non-naturally occurring polypeptides that transduces an immunostimulatory signal in an immune effector cell upon exposure to antigen and a multimerizing agent or bridging factor, e.g., stimulating immune effector cell activity and function, increasing production and/or secretion of proinflammatory cytokines. In preferred embodiments, a CLL-1 VHH DARIC is a multi-chain chimeric receptor comprising a DARIC signaling component and a DARIC binding component comprising a VHH domain that recognizes CLL-1.

In one embodiment, a DARIC signaling component and a DARIC binding component are expressed from the same cell. In another embodiment, a DARIC signaling component and a DARIC binding component are expressed from different cells. In a particular embodiment, a DARIC signaling component is expressed from a cell and a DARIC binding component is supplied exogenously, as a polypeptide. In one embodiment, a DARIC binding component pre-loaded with a bridging factor is supplied exogenously to a cell expressing a DARIC signaling component.

1. CLL-1 Daric Signaling Component

The terms "DARIC signaling component," CLL-1 DARIC signaling component," "DARIC signaling polypeptide," or "DARIC signaling polypeptide" are used interchangeably and refer to a polypeptide comprising one or more multimerization domains, a transmembrane domain, and one or more intracellular signaling domains. In particular embodiments, a DARIC signaling component comprises a multimerization domain, a transmembrane domain, a costimulatory domain and/or a primary signaling domain. In particular embodiments, a DARIC signaling component comprises a first multimerization domain, a first transmembrane domain, a first costimulatory domain and/or a primary signaling domain.

In particular embodiments, a DARIC signaling component comprises one or more multimerization domains.

Illustrative examples of multimerization domains suitable for use in particular CLL-1 DARIC signaling components contemplated herein include, but are not limited to, an FK506 binding protein (FKBP) polypeptide or variants thereof, an FKBP-rapamycin binding (FRB) polypeptide or variants thereof, a calcineurin polypeptide or variants thereof, a cyclophilin polypeptide or variants thereof, a bacterial dihydrofolate reductase (DHFR) polypeptide or variants thereof, a PYR1-like 1 (PYL1) polypeptide or variants thereof and an abscisic acid insensitive 1 (ABI1) polypeptide or variants thereof.

In particular embodiments, a CLL-1 DARIC signaling component comprises an FRB polypeptide.

In particular preferred embodiments, a CLL-1 DARIC signaling component comprises an FRB polypeptide comprising a T2098L mutation, or variant thereof. In certain preferred embodiments, a CLL-1 DARIC signaling component comprises an FKBP12 polypeptide or variant thereof.

In some embodiments, a CLL-1 VHH DARIC signaling component comprises a hinge domain.

Illustrative hinge domains suitable for use in a CLL-1 VHH DARIC signaling component described herein include the hinge region derived from the extracellular regions of type 1 membrane proteins such as CD28, CD8α, and CD4, which may be wild-type hinge regions from these molecules or may be altered.

In particular embodiments, a DARIC signaling component comprises a transmembrane domain.

In particular embodiments, a DARIC signaling component comprises a hinge domain and a transmembrane domain.

Illustrative examples of transmembrane domains suitable for use in particular CLL-1 DARIC signaling components contemplated herein include, but are not limited to, the transmembrane region(s) of the alpha, beta, gamma, or delta chain of a T-cell receptor, CD3ε, CD3ζ, CD4, CD5, CD8α, CD9, CD 16, CD22, CD27, CD28, CLL-1, CD37, CD45, CD64, CD71, CD80, CD86, CD 134, CD137, CD152, CD 154, amnionless (AMN), and programmed cell death 1 (PDCD1). In a preferred embodiment, a CLL-1 DARIC signaling component comprises a CD4 transmembrane domain. In a preferred embodiment, a CLL-1 DARIC signaling component comprises a CD8α transmembrane domain.

In particular embodiments, a DARIC signaling component comprises a linker that links the C-terminus of the transmembrane domain to the N-terminus of an intracellular signaling domain. In various preferred embodiments, a short oligo- or poly-peptide linker, preferably between 1, 2, 3, 4, 5, 6, 7, 8, 9, or 10 amino acids in length links the transmembrane domain and an intracellular signaling domain. A glycine-serine based linker provides a particularly suitable linker.

DARIC signaling components contemplated in particular embodiments herein comprise one or more intracellular signaling domains. In one embodiment, a CLL-1 DARIC signaling component comprises one or more costimulatory signaling domains and/or a primary signaling domain. In one embodiment, the intracellular signaling domain comprises an immunoreceptor tyrosine activation motif (ITAM).

Illustrative examples of ITAM containing primary signaling domains that are suitable for use in particular CLL-1 DARIC signaling components contemplated herein include, but are not limited to those derived from FcRγ, FcRβ, CD3γ, CD3δ, CD3ε, CD3ζ, CD22, CD79a, CD79b, and CD66d. In preferred embodiments, a CLL-1 DARIC signaling component comprises a CD3ζ primary signaling domain and one or more costimulatory signaling domains. The primary signaling and costimulatory signaling domains may be linked in any order in tandem to the carboxyl terminus of the transmembrane domain.

Illustrative examples of costimulatory domains suitable for use in particular CLL-1 DARIC signaling components contemplated herein include, but are not limited to those domains isolated from the following costimulatory molecules: Toll-like receptor 1 (TLR1), TLR2, TLR3, TLR4, TLR5, TLR6, TLR7, TLR8, TLR9, TLR10, caspase recruitment domain family member 11 (CARD11), CD2, CD7, CD27, CD28, CD30, CD40, CD54 (ICAM), CD83, CD94, CD134 (OX40), CD137 (4-11B), CD278 (ICOS), DNAX-Activation Protein 10 (DAP10), Linker for activation of T-cells family member 1 (LAT), SH2 Domain-Containing Leukocyte Protein Of 76 kD (SLP76), T cell receptor associated transmembrane adaptor 1 (TRAT1), TNFR2, TNF receptor superfamily member 14 (TNFRS14; HVEM), TNF receptor superfamily member 18 (TNFRS18; GITR), TNF receptor superfamily member 25 (TNFRS25; DR3), and zeta chain of T cell receptor associated protein kinase 70 (ZAP70).

In particular embodiments, a CLL-1 DARIC signaling component contemplated herein comprises a signal peptide. Illustrative examples of signal peptides suitable for use in particular CLL-1 DARIC signaling components include but are not limited to an IgG1 heavy chain signal polypeptide, an Igκ light chain signal polypeptide, a CD8α signal polypeptide, or a human GM-CSF receptor alpha signal polypeptide. In various preferred embodiments, a CLL-1 DARIC signaling component comprises a CD8α signal polypeptide.

In particular embodiments, a CLL-1 DARIC signaling component comprises one or more costimulatory signaling domains selected from the group consisting of CD28, CD137, and CD134. In particular embodiments, a CLL-1 DARIC signaling component comprises one or more costimulatory signaling domains selected from the group consisting of CD28, CD137, and CD134, and a CD3ζ primary signaling domain. In a particular embodiment, a CLL-1 DARIC signaling component comprises a CD137 costimulatory domain and a CD3ζ primary signaling domain.

In a preferred embodiment, a CLL-1 DARIC signaling component comprises an FRB T2098L multimerization domain, a CD8α transmembrane domain, a CD137 costimulatory domain and a CD3ζ primary signaling domain.

In preferred embodiments, a CLL-1 $V_HH$ DARIC signaling component comprises an amino acid sequence set forth in SEQ ID NO 50.

2. CLL-1 Daric Binding Component

A "DARIC binding component," "DARIC binding polypeptide," "CLL-1 VHH DARIC binding component," or "CLL-1 VHH DARIC binding polypeptide" are used interchangeably and refer to a polypeptide comprising an anti-CLL-1 $V_HH$ domain, and one or more multimerization domains. In particular embodiments, the CLL-1 VHH DARIC binding component comprises an anti-CLL-1 VHH domain, a multimerization domain and a transmembrane domain. In particular embodiments, the CLL-1 VHH DARIC binding component comprises an anti-CLL-1 VHH domain, a second multimerization domain, and a second transmembrane domain. In other particular embodiments, the CLL-1 VHH DARIC binding component comprises an anti-CLL-1 VHH domain, a multimerization domain, a transmembrane domain and one or more intracellular signaling domains. In particular embodiments, the CLL-1 VHH DARIC binding component comprises an anti-CLL-1 VHH domain, a second multimerization domain, a second transmembrane domain, and a second costimulatory domain.

In particular embodiments, the CLL-1 VHH DARIC binding component comprises one or more anti-CLL-1 VHH domains.

In particular embodiments, the anti-CLL-1 VHH domain is a humanized camelid VHH that binds one or more epitopes of CLL-1 (e.g., SEQ ID NO: 1).

In particular preferred embodiments, the anti-CLL-1 VHH domain is a humanized camelid VHH comprising the amino acid sequence set forth in any one of SEQ ID NOs: 2-13, i.e., 2, 3, 4, 5, 6, 7, 8, 9, 10, 11, 12, or 13.

In particular embodiments, a DARIC binding component comprises one or more multimerization domains.

Illustrative examples of multimerization domains suitable for use in particular CLL-1 VHH DARIC binding components contemplated herein include, but are not limited to, an FKBP polypeptide or variants thereof, an FRB polypeptide or variants thereof, a calcineurin polypeptide or variants thereof, a cyclophilin polypeptide or variants thereof, a DHFR polypeptide or variants thereof, a PYL1 polypeptide or variants thereof and an ABI1 polypeptide or variants thereof.

In particular embodiments, a CLL-1 VHH DARIC binding component comprises an FRB polypeptide or variant thereof and a DARIC signaling component comprises an FKBP polypeptide or variant thereof. In a preferred embodiment, a CLL-1 VHH DARIC binding component comprises an FRB polypeptide comprising a T2098L mutation, or variant thereof and a DARIC signaling component comprises an FKBP12 polypeptide or variant thereof.

In particular embodiments, a CLL-1 VHH DARIC binding component comprises an FKBP polypeptide or variant thereof and a DARIC signaling component comprises an FRB polypeptide, or variant thereof. In a preferred embodiment, a CLL-1 VHH DARIC binding component comprises an FKBP12 polypeptide, or variant thereof and a DARIC signaling component comprises an FRB polypeptide comprising a T2098L mutation, or variant thereof.

In some embodiments, a CLL-1VHH DARIC binding component comprises a hinge domain.

Illustrative hinge domains suitable for use in a CLL-1VHH DARIC binding component described herein include the hinge region derived from the extracellular regions of type 1 membrane proteins such as CD28, CD8α, and CD4, which may be wild-type hinge regions from these molecules or may be altered.

In particular embodiments, a DARIC binding component comprises a transmembrane domain. In particular embodiments, a DARIC binding component comprises a hinge domain and a transmembrane domain. In one embodiment, the transmembrane domain may be the same as the transmembrane domain used in the DARIC signaling component. In one embodiment, the transmembrane domain may be different from the transmembrane domain used in the DARIC signaling component.

Illustrative examples of transmembrane domains suitable for use in particular CLL-1 VHH DARIC binding components contemplated herein include, but are not limited to, the transmembrane region(s) of the alpha, beta, gamma, or delta chain of a T-cell receptor, CD3ε, CD3ζ, CD4, CD5, CD8α, CD9, CD 16, CD22, CD27, CD28, CLL-1, CD3γ, CD45, CD64, CD71, CD80, CD86, CD 134, CD137, CD152, CD 154, amnionless (AMN), and programmed cell death 1 (PDCD1). In a preferred embodiment, a CLL-1 DARIC binding component comprises a CD8α transmembrane domain. In a preferred embodiment, a CLL-1 VHH DARIC binding component comprises a CD4 transmembrane domain.

In various preferred embodiments, a short oligo- or polypeptide linker, preferably between 1, 2, 3, 4, 5, 6, 7, 8, 9, or 10 amino acids in length links the transmembrane domain and the intracellular signaling domain. A glycine-serine based linker provides a particularly suitable linker.

DARIC binding components contemplated in particular embodiments herein do not comprise one or more intracellular signaling domains.

In other particular embodiments, CLL-1 VHH DARIC binding components contemplated herein comprise one or more intracellular signaling domains. In preferred embodiments, wherein the CLL-1 VHH DARIC binding component comprises one or more intracellular signaling domains, those domains are different that the intracellular signaling domains present in the cognate CLL-1 DARIC signaling component. In one embodiment, a CLL-1 VHH DARIC binding component comprises a costimulatory signaling domain.

Illustrative examples of costimulatory domains suitable for use in particular CLL-1 VHH DARIC binding components contemplated herein include, but are not limited to those domains isolated from the following costimulatory molecules: Toll-like receptor 1 (TLR1), TLR2, TLR3, TLR4, TLR5, TLR6, TLR7, TLR8, TLR9, TLR10, caspase recruitment domain family member 11 (CARD11), CD2, CD7, CD27, CD28, CD30, CD40, CD54 (ICAM), CD83, CD94, CD134 (OX40), CD137 (4-1BB), CD278 (ICOS), DNAX-Activation Protein 10 (DAP10), Linker for activation of T-cells family member 1 (LAT), SH2 Domain-Containing Leukocyte Protein Of 76 kD (SLP76), T cell receptor associated transmembrane adaptor 1 (TRAT1), TNFR2, TNF receptor superfamily member 14 (TNFRS14; HVEM), TNF receptor superfamily member 18 (TNFRS18; GITR), TNF receptor superfamily member 25 (TNFRS25; DR3), and zeta chain of T cell receptor associated protein kinase 70 (ZAP70). In preferred embodiments, the costimulatory domain is derived, obtained, or isolated from TNFR2 or OX40.

In particular embodiments, a DARIC binding component contemplated herein comprises a signal peptide. Illustrative examples of signal peptides suitable for use in particular CLL-1 VHH DARIC binding components include but are not limited to an IgG1 heavy chain signal polypeptide, an Igκ light chain signal polypeptide, a CD8α signal polypeptide, or a human GM-CSF receptor alpha signal polypeptide. In various preferred embodiments, a CLL-1 VHH DARIC binding component comprises a CD8α signal polypeptide.

In particular embodiments, a CLL-1 VHH DARIC binding component comprises a VHH domain that binds to CLL-1, an FKBP12 multimerization domain, and a CD4 transmembrane domain and optionally, a costimulatory domain.

In certain embodiments, a CLL-1 VHH DARIC binding component comprises a VHH that binds to CLL-1, and an FKBP12 multimerization domain.

In some embodiments, a CLL-1 VHH DARIC binding component comprises a VHH domain comprising the amino acid sequence set forth in any one of SEQ ID NOs: 2-13, an FKBP12 multimerization domain, and a CD4 transmembrane domain and optionally, a costimulatory domain.

In some embodiments, a CLL-1 VHH DARIC binding component comprises a VHH domain comprising the amino acid sequence set forth in any one of SEQ ID NOs: 2-13, and an FKBP12 multimerization domain.

In some embodiments, a CLL-1 VHH DARIC binding component comprises the amino acid sequence set forth in any one of SEQ ID NOs: 14-19.

3. Bridging Factor

Bridging factors contemplated in particular embodiments herein, mediate or promote the association of a CLL-1 DARIC signaling component with a CLL-1 VHH DARIC binding component through multimerization domains in the respective components. A bridging factor associates with and is disposed between the multimerization domains to promote association of a CLL-1 DARIC signaling component and a CLL-1 VHH DARIC binding component. In the presence of a bridging factor, the CLL-1 VHH DARIC binding component and the CLL-1 DARIC signaling component associate and initiate immune effector cell activity against a target cell when the CLL-1 VHH DARIC binding component binds CLL-1 expressed on the target cell. In the absence of a bridging factor, the CLL-1 VHH DARIC binding component does not associate with the CLL-1 DARIC signaling component and the CLL-1 VHH DARIC is inactive.

In particular embodiments, a CLL-1 DARIC signaling component and a CLL-1 VHH DARIC binding component comprise a cognate pair of multimerization domains selected from the group consisting of: FKBP and FKBP12-rapamycin binding (FRB), FKBP and calcineurin, FKBP and cyclophilin, FKBP and bacterial dihydrofolate reductase (DHFR), calcineurin and cyclophilin, and PYR1-like 1 (PYL1) and abscisic acid insensitive 1 (ABI1).

In certain embodiments, the multimerization domains of CLL-1 VHH DARIC signaling and binding components associate with a bridging factor selected from the group consisting of: rapamycin or a rapalog thereof, coumermycin or a derivative thereof, gibberellin or a derivative thereof, abscisic acid (ABA) or a derivative thereof, methotrexate or a derivative thereof, cyclosporin A or a derivative thereof, FK506/cyclosporin A (FKCsA) or a derivative thereof, and trimethoprim (Tmp)-synthetic ligand for FK506 binding protein (FKBP) (SLF) or a derivative thereof.

In particular embodiments, a CLL-1 DARIC signaling component and a CLL-1 VHH DARIC binding component comprise one or more FRB and/or FKBP multimerization domains or variants thereof. In certain embodiments, a CLL-1 DARIC signaling component comprises an FRB multimerization domain or variant thereof and a CLL-1 VHH DARIC binding component comprises an FKBP multimerization domain or variant thereof. In particular preferred embodiments, a CLL-1 DARIC signaling component comprises an FRB T2098L multimerization domain or variant thereof and a CLL-1 VHH DARIC binding component comprises an FKBP12 or FKBP12 F36V multimerization domains or variant thereof.

Illustrative examples of bridging factors suitable for use in particular embodiments contemplated herein include, but are not limited to, AP1903, AP20187, AP21967 (also known as C-16-(S)-7-methylindolerapamycin), everolimus, novolimus, pimecrolimus, ridaforolimus, tacrolimus, temsirolimus, umirolimus, and zotarolimus. In particular preferred embodiments, the bridging factor is AP21967. In certain preferred embodiments, the bridging factor is a non-immunosuppressive dose of sirolimus (rapamycin).

D. Anti-CLL-1 Chimeric Antigen Receptors

In particular embodiments, immune effector cells contemplated herein comprise an anti-CLL-1 VHH CAR. Chimeric antigen receptors (CARs) are molecules that combine antibody-based specificity for a target antigen (e.g., tumor antigen) with a T cell receptor-activating intracellular domain to generate a chimeric protein that exhibits a specific anti-tumor cellular immune activity. As used herein, the term, "chimeric," describes being composed of parts of different proteins or DNAs from different origins.

In particular embodiments, T cells are engineered by introducing a polynucleotide encoding an anti-CLL-1 VHH CAR.

In particular embodiments, T cells are engineered by introducing a vector comprising a polynucleotide encoding an anti-CLL-1 VHH CAR.

In various embodiments, an anti-CLL-1 CAR comprises a VHH domain that binds CLL-1, a transmembrane domain and one or more intracellular signaling domains. The main characteristic of CARs is their ability to redirect immune effector cell specificity, thereby triggering proliferation, cytokine production, phagocytosis or production of molecules that can mediate cell death of the target antigen expressing cell in a major histocompatibility (MHC) independent manner, exploiting the cell specific targeting abilities of monoclonal antibodies, soluble ligands or cell specific coreceptors.

In some embodiments, an anti-CLL-1 VHH CAR comprises a spacer domain. In particular embodiments, the spacer domain comprises the CH2 and CH3 of IgG1, IgG4, or IgD.

In some embodiments, an anti-CLL-1 VHH CAR comprises a hinge domain.

Illustrative hinge domains suitable for use in the anti-CLL-1 VHH CARs described herein include the hinge region derived from the extracellular regions of type 1 membrane proteins such as CD28, CD8α, and CD4, which may be wild-type hinge regions from these molecules or may be altered. In another embodiment, the hinge domain comprises a CD8α hinge region.

The transmembrane (TM) domain of the CAR fuses the extracellular binding portion and intracellular signaling domain and anchors the CAR to the plasma membrane of the immune effector cell. The TM domain may be derived either from a natural, synthetic, semi-synthetic, or recombinant source.

Illustrative TM domains may be derived from (i.e., comprise at least the transmembrane region(s) of the alpha, beta, gamma, or delta chain of a T-cell receptor, CD3ε, CD3ζ, CD4, CD5, CD8α, CD9, CD 16, CD22, CD27, CD28, CLL-1, CD3γ, CD45, CD64, CD71, CD80, CD86, CD 134, CD137, CD152, CD 154, AMN, and PDCD1.

In one embodiment, an anti-CLL-1 VHH CAR comprises a TM domain derived from CD8α. In another embodiment, a CAR contemplated herein comprises a TM domain derived from CD8α and a short oligo- or polypeptide linker, preferably between 1, 2, 3, 4, 5, 6, 7, 8, 9, or 10 amino acids in length that links the TM domain and the intracellular signaling domain of the CAR. A glycine-serine linker provides a particularly suitable linker.

In preferred embodiments, an anti-CLL-1 VHH CAR comprises an intracellular signaling domain that comprises one or more costimulatory signaling domains and a primary signaling domain.

Primary signaling domains that act in a stimulatory manner may contain signaling motifs which are known as immunoreceptor tyrosine-based activation motifs or ITAMs.

Illustrative examples of ITAM containing primary signaling domains suitable for use in anti-CLL-1 VHH CARs contemplated in particular embodiments include those derived from FcRγ, FcRβ, CD3γ, CD3δ, CD3ε, CD3ζ, CD22, CD79a, CD79b, and CD66d. In particular preferred embodiments, a CAR comprises a CD3ζ primary signaling domain and one or more costimulatory signaling domains. The intracellular primary signaling and costimulatory signaling domains may be linked in any order in tandem to the carboxyl terminus of the transmembrane domain.

In particular embodiments, an anti-CLL-1 VHH CAR comprises one or more costimulatory signaling domains to enhance the efficacy and expansion of T cells expressing CAR receptors.

Illustrative examples of such costimulatory molecules suitable for use in anti-CLL-1 VHH CARs contemplated in particular embodiments include, but are not limited to, TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD94, CD134 (OX40), CD137 (4-1BB), CD278 (ICOS), DAP10, LAT, SLP76, TRAT1, TNFR2, and ZAP70. In one embodiment, a CAR comprises one or more costimulatory signaling domains selected from the group consisting of CD28, CD137, and CD134, and a CD3ζ primary signaling domain.

In various embodiments, the anti-CLL-1 VHH CAR comprises: a VHH that binds CLL-1; a transmembrane domain isolated from a polypeptide selected from the group consisting of: CD4, CD8α, CD154, and PD-1; one or more intracellular costimulatory signaling domains isolated from a polypeptide selected from the group consisting of: CD28, CD134, and CD137; and a signaling domain isolated from a polypeptide selected from the group consisting of: FcRγ, FcRβ, CD3γ, CD3δ, CD3ε, CD3ζ, CD22, CD79a, CD79b, and CD66d.

In various embodiments, the anti-CLL-1 VHH CAR comprises: a VHH that binds CLL-1; a transmembrane domain isolated from a polypeptide selected from the group consisting of: CD4, CD8α, CD154, and PD-1; one or more intracellular costimulatory signaling domains isolated from a polypeptide selected from the group consisting of: CD28, CD134, and CD137; and a signaling domain isolated from a polypeptide selected from the group consisting of: FcRγ, FcRβ, CD3γ, CD3δ, CD3ε, CD3ζ, CD22, CD79a, CD79b, and CD66d.

In preferred embodiments, an anti-CLL-1 VHH CAR comprises a VHH that comprises an amino acid sequence set forth in any one of SEQ ID NOs: 2-13, i.e., 2, 3, 4, 5, 6, 7, 8, 9, 10, 11, 12, or 13, a CD8α hinge domain, a CD8α transmembrane domain, a 4-1BB costimulatory domain, and a CD3ζ primary signaling domain.

In particular embodiments, an anti-CLL-1 VHH CAR comprises a sequence set forth in any one of SEQ ID NOs: 38-49, i.e., 38, 39, 40, 41, 42, 43, 44, 45, 46, 47, 48, and 49.

E. Polypeptides

Various polypeptides are contemplated herein, including, but not limited to, CLL-1 VHH DARICs, CLL-1 VHH DARIC binding components, CLL-1 DARIC signaling components, anti-CLL-1 VHH CARs, and fragments thereof. In preferred embodiments, a polypeptide comprises an amino acid sequence set forth in any one of SEQ ID NOs: 2-50. "Polypeptide," "peptide" and "protein" are used interchangeably, unless specified to the contrary, and according to conventional meaning, i.e., as a sequence of amino acids. In one embodiment, a "polypeptide" includes fusion polypeptides and other variants. Polypeptides can be prepared using any of a variety of well-known recombinant and/or synthetic techniques. Polypeptides are not limited to a specific length, e.g., they may comprise a full-length protein sequence, a fragment of a full-length protein, or a fusion protein, and may include post-translational modifications of the polypeptide, for example, glycosylations, acetylations, phosphorylations and the like, as well as other modifications known in the art, both naturally occurring and non-naturally occurring. In particular preferred embodiments, fusion polypeptides, polypeptides, fragments and other variants thereof are prepared, obtained, or isolated from one or more human polypeptides.

An "isolated peptide" or an "isolated polypeptide" and the like, as used herein, refer to in vitro isolation and/or purification of a peptide or polypeptide molecule from a cellular environment, and from association with other components of the cell, i.e., it is not significantly associated with in vivo substances. In particular embodiments, an isolated polypeptide is a synthetic polypeptide, a semi-synthetic polypeptide, or a polypeptide obtained or derived from a recombinant source.

Polypeptides include "polypeptide variants." Polypeptide variants may differ from a naturally occurring polypeptide in one or more substitutions, deletions, additions and/or insertions. Such variants may be naturally occurring or may be synthetically generated, for example, by modifying one or more of the above polypeptide sequences. For example, in particular embodiments, it may be desirable to improve the binding affinity and/or other biological properties of a polypeptide by introducing one or more substitutions, deletions, additions and/or insertions the polypeptide. In particular embodiments, polypeptides include polypeptides having at least about 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 86%, 97%, 98%, or 99% amino acid identity to any of the reference sequences contemplated herein, typically where the variant maintains at least one biological activity of the reference sequence. In particular embodiments, the biological activity is binding affinity. In particular embodiments, the biological activity is cytolytic activity.

Polypeptide variants include biologically active "polypeptide fragments." Illustrative examples of biologically active polypeptide fragments include anti-CLL-1 VHH domains, intracellular signaling domains, and the like. As used herein, the term "biologically active fragment" or "minimal biologically active fragment" refers to a polypeptide fragment that retains at least 100%, at least 90%, at least 80%, at least 70%, at least 60%, at least 50%, at least 40%, at least 30%, at least 20%, at least 10%, or at least 5% of the naturally occurring polypeptide activity. In certain embodiments, a polypeptide fragment can comprise an amino acid chain at least 5 to about 1700 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, 450, 500, 550, 600, 650, 700, 750, 800, 850, 900, 950, 1000, 1100, 1200, 1300, 1400, 1500, 1600, 1700 or more amino acids long.

In particular embodiments, the polypeptides set forth herein may comprise one or more amino acids denoted as "X" or "Xaa," which are used interchangeably. "X" if present in an amino acid SEQ ID NO, refers to any one or more amino acids. In particular embodiments, SEQ ID NOs denoting a fusion protein comprise a sequence of continuous X residues that cumulatively represent any amino acid sequence. In particular embodiments, "XX" represent any two amino acid combination. In certain embodiments, "XX" represents two serines, SS. In certain embodiments, "XX" represents any two amino acid combination that reduces immunogenicity.

In preferred embodiments, "XX" represents the amino acids KP.

As noted above, polypeptides may be altered in various ways including amino acid substitutions, deletions, truncations, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (1985, *Proc. Natl. Acad. Sci. USA.* 82: 488-492), Kunkel et al., (1987, *Methods in Enzymol,* 154: 367-382), U.S. Pat. No. 4,873,192, Watson, J. D. et al., (*Molecular Biology of the Gene*, Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) *Atlas of Protein Sequence and Structure* (*Natl. Biomed. Res. Found.*, Washington, D.C.).

In certain embodiments, a polypeptide variant comprises one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Modifications may be made in the structure of the polynucleotides and polypeptides contemplated in particular embodiments and still obtain a functional molecule that encodes a variant or derivative polypeptide with desirable characteristics. When it is desired to alter the amino acid sequence of a polypeptide to create an equivalent, or even an improved, variant polypeptide, one skilled in the art, for example, can change one or more of the codons of the encoding DNA sequence, e.g., according to Table 1.

TABLE 1

Amino Acid Codons

| Amino Acids | One letter code | Three letter code | Codons | | | | | |
|---|---|---|---|---|---|---|---|---|
| Alanine | A | Ala | GCA | GCC | GCG | GCU | | |
| Cysteine | C | Cys | UGC | UGU | | | | |
| Aspartic acid | D | Asp | GAC | GAU | | | | |
| Glutamic acid | E | Glu | GAA | GAG | | | | |
| Phenylalanine | F | Phe | UUC | UUU | | | | |
| Glycine | G | Gly | GGA | GGC | GGG | GGU | | |
| Histidine | H | His | CAC | CAU | | | | |
| Isoleucine | I | Iso | AUA | AUC | AUU | | | |
| Lysine | K | Lys | AAA | AAG | | | | |
| Leucine | L | Leu | UUA | UUG | CUA | CUC | CUG | CUU |
| Methionine | M | Met | AUG | | | | | |
| Asparagine | N | Asn | AAC | AAU | | | | |
| Proline | P | Pro | CCA | CCC | CCG | CCU | | |
| Glutamine | Q | Gln | CAA | CAG | | | | |
| Arginine | R | Arg | AGA | AGG | CGA | CGC | CGG | CGU |
| Serine | S | Ser | AGC | AGU | UCA | UCC | UCG | UCU |
| Threonine | T | Thr | ACA | ACC | ACG | ACU | | |
| Valine | V | Val | GUA | GUC | GUG | GUU | | |
| Tryptophan | W | Trp | UGG | | | | | |
| Tyrosine | Y | Tyr | UAC | UAU | | | | |

Guidance in determining which amino acid residues can be substituted, inserted, or deleted without abolishing biological activity can be found using computer programs well known in the art, such as DNASTAR, DNA Strider, Geneious, Mac Vector, or Vector NTI software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. Co., p. 224).

In one embodiment, where expression of two or more polypeptides is desired, the polynucleotide sequences encoding them can be separated by an IRES sequence or a polynucleotide sequence encoding a ribosomal skip sequence as disclosed elsewhere herein.

Polypeptides contemplated in particular embodiments include fusion polypeptides. In particular embodiments, fusion polypeptides and polynucleotides encoding fusion polypeptides are provided. Fusion polypeptides and fusion proteins refer to a polypeptide having at least two, three, four, five, six, seven, eight, nine, or ten polypeptide segments. In preferred embodiments, a fusion polypeptide comprises one or more CLL-1 VHH DARIC components. In other preferred embodiments, the fusion polypeptide comprises one or more CLL-1 VHH DARICs.

In another embodiment, two or more CLL-1 VHH DARIC components and/or other polypeptides can be expressed as a fusion protein that comprises one or more self-cleaving peptide sequences between the polypeptides as disclosed elsewhere herein.

In particular embodiments, a fusion polypeptide comprises a CLL-1 DARIC signaling component, a self-cleaving polypeptide sequence or ribosomal skip sequence, and a CLL-1 VHH DARIC binding component.

In particular embodiments, a fusion polypeptide comprises a CLL-1 DARIC signaling component, a self-cleaving polypeptide sequence or ribosomal skip sequence, a CLL-1 VHH DARIC binding component, another self-cleaving polypeptide sequence or ribosomal skip sequence, and another DARIC binding component that is directed against another target antigen.

Fusion polypeptides can comprise one or more polypeptide domains or segments including, but are not limited to signal peptides, cell permeable peptide domains (CPP), binding domains, signaling domains, etc., epitope tags (e.g., maltose binding protein ("MBP"), glutathione S transferase (GST), HIS6, MYC, FLAG, V5, VSV-G, and HA), polypeptide linkers, and polypeptide cleavage signals. Fusion polypeptides are typically linked C-terminus to N-terminus, although they can also be linked C-terminus to C-terminus, N-terminus to N-terminus, or N-terminus to C-terminus. In particular embodiments, the polypeptides of the fusion protein can be in any order. Fusion polypeptides or fusion proteins can also include conservatively modified variants, polymorphic variants, alleles, mutants, subsequences, and interspecies homologs, so long as the desired activity of the fusion polypeptide is preserved. Fusion polypeptides may be produced by chemical synthetic methods or by chemical linkage between the two moieties or may generally be prepared using other standard techniques. Ligated DNA sequences comprising the fusion polypeptide are operably linked to suitable transcriptional or translational control elements as disclosed elsewhere herein.

Fusion polypeptides may optionally comprise one or more linkers that can be used to link the one or more polypeptides or domains within a polypeptide. A peptide linker sequence may be employed to separate any two or more polypeptide components by a distance sufficient to ensure that each polypeptide folds into its appropriate secondary and tertiary structures so as to allow the polypeptide domains to exert their desired functions. Such a peptide linker sequence is incorporated into the fusion polypeptide using standard techniques in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. In particular embodiments, preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. Nos. 4,935,233 and 4,751,180. Linker sequences are not required when a particular fusion polypeptide segment contains nonessential N-terminal amino acid regions that can be used to separate the functional domains and prevent steric interference. In particular embodiments, preferred linkers are typically flexible amino acid subsequences which are synthesized as part of a recombinant fusion protein. Linker polypeptides can be between 1 and 200 amino acids in length, between 1 and 100 amino acids in length, or between 1 and 50 amino acids in length, including all integer values in between.

Exemplary polypeptide cleavage signals include polypeptide cleavage recognition sites such as protease cleavage sites, nuclease cleavage sites (e.g., rare restriction enzyme recognition sites, self-cleaving ribozyme recognition sites), and self-cleaving viral oligopeptides (see deFelipe and Ryan, 2004. *Traffic,* 5(8); 616-26).

Suitable protease cleavages sites and self-cleaving peptides are known to the skilled person (see, e.g., in Ryan et al., 1997. *J. Gener. Virol.* 78, 699-722; Scymczak et al. (2004) Nature Biotech. 5, 589-594). Exemplary protease cleavage sites include, but are not limited to the cleavage sites of potyvirus NIa proteases (e.g., tobacco etch virus protease), potyvirus HC proteases, potyvirus P1 (P35) proteases, byovirus NIa proteases, byovirus RNA-2-encoded proteases, aphthovirus L proteases, enterovirus 2A proteases, rhinovirus 2A proteases, picorna 3C proteases, comovirus 24K proteases, nepovirus 24K proteases, RTSV (rice tungro spherical virus) 3C-like protease, PYVF (parsnip yellow fleck virus) 3C-like protease, heparin, thrombin, factor Xa and enterokinase. Due to its high cleavage stringency, TEV (tobacco etch virus) protease cleavage sites are preferred in one embodiment, e.g., EXXYXQ(G/S) (SEQ ID NO: 63), for example, ENLYFQG (SEQ ID NO: 64) and ENLYFQS (SEQ ID NO: 65), wherein X represents any amino acid (cleavage by TEV occurs between Q and G or Q and S).

In particular embodiments, the polypeptide cleavage signal is a viral self-cleaving peptide or ribosomal skipping sequence.

Illustrative examples of ribosomal skipping sequences include, but are not limited to: a 2A or 2A-like site, sequence or domain (Donnelly et al., 2001. *J. Gen. Virol.* 82:1027-1041). In a particular embodiment, the viral 2A peptide is an aphthovirus 2A peptide, a potyvirus 2A peptide, or a cardiovirus 2A peptide.

In one embodiment, the viral 2A peptide is selected from the group consisting of a foot-and-mouth disease virus (FMDV) 2A peptide, an equine rhinitis A virus (ERAV) 2A peptide, a Thosea asigna virus (TaV) 2A peptide, a porcine teschovirus-1 (PTV-1) 2A peptide, a Theilovirus 2A peptide, and an encephalomyocarditis virus 2A peptide.

Illustrative examples of 2A sites are provided in Table 2.

TABLE 2

| | |
|---|---|
| SEQ ID NO: 66 | GSGATNFSLLKQAGDVEENPGP |
| SEQ ID NO: 67 | ATNFSLLKQAGDVEENPGP |
| SEQ ID NO: 68 | LLKQAGDVEENPGP |
| SEQ ID NO: 69 | GSGEGRGSLLTCGDVEENPGP |
| SEQ ID NO: 70 | EGRGSLLTCGDVEENPGP |
| SEQ ID NO: 71 | LLTCGDVEENPGP |
| SEQ ID NO: 72 | GSGQCTNYALLKLAGDVESNPGP |
| SEQ ID NO: 73 | QCTNYALLKLAGDVESNPGP |
| SEQ ID NO: 74 | LLKLAGDVESNPGP |
| SEQ ID NO: 75 | GSGVKQTLNFDLLKLAGDVESNPGP |
| SEQ ID NO: 76 | VKQTLNFDLLKLAGDVESNPGP |
| SEQ ID NO: 77 | LLKLAGDVESNPGP |
| SEQ ID NO: 78 | LLNFDLLKLAGDVESNPGP |
| SEQ ID NO: 79 | TLNFDLLKLAGDVESNPGP |
| SEQ ID NO: 80 | LLKLAGDVESNPGP |
| SEQ ID NO: 81 | NFDLLKLAGDVESNPGP |
| SEQ ID NO: 82 | QLLNFDLLKLAGDVESNPGP |
| SEQ ID NO: 83 | APVKQTLNFDLLKLAGDVESNPGP |
| SEQ ID NO: 84 | VTELLYRMKRAETYCPRPLLAIHPTEARHKQKIVAPVKQT |
| SEQ ID NO: 85 | LNFDLLKLAGDVESNPGP |
| SEQ ID NO: 86 | LLAIHPTEARHKQKIVAPVKQTLNFDLLKLAGDVESNPGP |
| SEQ ID NO: 87 | EARHKQKIVAPVKQTLNFDLLKLAGDVESNPGP |

In preferred embodiments, a polypeptide or fusion polypeptide comprises one or more CLL-1 VHH DARIC components, CLL-1 VHH DARICs, or anti-CLL-1 VHH CAR.

In preferred embodiments, a fusion polypeptide comprises a CLL-1 DARIC signaling component and a CLL-1 VHH DARIC binding component separated by a self-cleaving polypeptide sequence.

In particular embodiments, a fusion polypeptide comprises the sequence set forth in any one of SEQ ID NOs: 20-37, i.e., 20, 21, 22, 23, 24, 25, 26, 27, 28, 29, 30, 31, 32, 33, 34, 35, 36, or 37.

In particular embodiments, a fusion polypeptide comprises a CLL-1 DARIC signaling component comprising an FRB T2098L multimerization domain, a CD8α transmembrane domain, a CD137 costimulatory domain and a CD3ζ primary signaling domain; a viral self-cleaving 2A polypeptide; and a CLL-1 VHH DARIC binding component comprising an anti-CLL-1 VHH, an FKBP12 multimerization domain polypeptide, and a CD4 transmembrane domain.

In particular embodiments, a fusion polypeptide comprises the sequence set forth in any one of SEQ ID NOs: 20-25, i.e., 20, 21, 22, 23, 24, or 25.

In particular embodiments, a fusion polypeptide comprises a CLL-1 DARIC signaling component comprising an FRB T2098L multimerization domain, a CD8α transmembrane domain, a CD137 costimulatory domain and a CD3ζ primary signaling domain; a viral self-cleaving 2A polypeptide; and an anti-CLL-1 VHH, a CD4 transmembrane domain, and optionally a CD27, CD28, TNFRS14, TNFRS18, TNFRS25, OX40 or TNFR2 costimulatory domain.

In particular embodiments, a fusion polypeptide comprises the sequence set forth in any one of SEQ ID NOs: 26-31, i.e., 26, 27, 28, 29, 30, or 31.

In particular embodiments, a fusion polypeptide comprises the sequence set forth in any one of SEQ ID NOs: 32-37, i.e., 32, 33, 34, 35, 36, or 37.

F. Polynucleotides

In particular embodiments, polynucleotides encoding CLL-1 VHH DARICs, CLL-1 VHH DARIC binding components, CLL-1 DARIC signaling components, anti-CLL-1 VHH CARs and fragments thereof are provided. As used herein, the terms "polynucleotide" or "nucleic acid" refer to deoxyribonucleic acid (DNA), ribonucleic acid (RNA) and DNA/RNA hybrids. Polynucleotides may be single-stranded or double-stranded and either recombinant, synthetic, or isolated. Polynucleotides include but are not limited to: pre-messenger RNA (pre-mRNA), messenger RNA (mRNA), RNA, synthetic RNA, synthetic mRNA, genomic DNA (gDNA), PCR amplified DNA, complementary DNA (cDNA), synthetic DNA, or recombinant DNA. Polynucleotides refer to a polymeric form of nucleotides of at least 5, at least 10, at least 15, at least 20, at least 25, at least 30, at least 40, at least 50, at least 100, at least 200, at least 300, at least 400, at least 500, at least 1000, at least 5000, at least 10000, or at least 15000 or more nucleotides in length, either ribonucleotides or deoxyribonucleotides or a modified form of either type of nucleotide, as well as all intermediate lengths. It will be readily understood that "intermediate lengths," in this context, means any length between the quoted values, such as 6, 7, 8, 9, etc., 101, 102, 103, etc.; 151, 152, 153, etc.; 201, 202, 203, etc. In particular embodiments, polynucleotides or variants have at least or about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a reference sequence.

As used herein, "isolated polynucleotide" refers to a polynucleotide that has been purified from the sequences which flank it in a naturally-occurring state, e.g., a DNA fragment that has been removed from the sequences that are normally adjacent to the fragment. In particular embodiments, an "isolated polynucleotide" also refers to a complementary DNA (cDNA), a recombinant DNA, or other polynucleotide that does not exist in nature and that has been made by the hand of man. In particular embodiments, an isolated polynucleotide is a synthetic polynucleotide, a semi-synthetic polynucleotide, or a polynucleotide obtained or derived from a recombinant source.

In various embodiments, a polynucleotide comprises an mRNA encoding a polypeptide contemplated herein. In certain embodiments, the mRNA comprises a cap, one or more nucleotides, and a poly(A) tail.

In particular embodiments, polynucleotides encoding one or more CLL-1 VHH DARIC components may be codon-optimized. As used herein, the term "codon-optimized" refers to substituting codons in a polynucleotide encoding a polypeptide in order to increase the expression, stability and/or activity of the polypeptide. Factors that influence codon optimization include, but are not limited to one or more of: (i) variation of codon biases between two or more organisms or genes or synthetically constructed bias tables, (ii) variation in the degree of codon bias within an organism, gene, or set of genes, (iii) systematic variation of codons including context, (iv) variation of codons according to their decoding tRNAs, (v) variation of codons according to GC %, either overall or in one position of the triplet, (vi) variation in degree of similarity to a reference sequence for example a naturally occurring sequence, (vii) variation in the codon frequency cutoff, (viii) structural properties of mRNAs transcribed from the DNA sequence, (ix) prior knowledge about the function of the DNA sequences upon which design of the codon substitution set is to be based, (x) systematic variation of codon sets for each amino acid, and/or (xi) isolated removal of spurious translation initiation sites.

As used herein the term "nucleotide" refers to a heterocyclic nitrogenous base in N-glycosidic linkage with a phosphorylated sugar. Nucleotides are understood to include natural bases, and a wide variety of art-recognized modified bases. Such bases are generally located at the 1' position of a nucleotide sugar moiety. Nucleotides generally comprise a base, sugar and a phosphate group. In ribonucleic acid (RNA), the sugar is a ribose, and in deoxyribonucleic acid (DNA) the sugar is a deoxyribose, i.e., a sugar lacking a hydroxyl group that is present in ribose.

Illustrative examples of polynucleotides include, but are not limited to, polynucleotides encoding polypeptides set forth in SEQ ID NOs: 2-50.

In various illustrative embodiments, polynucleotides contemplated herein include, but are not limited to polynucleotides encoding one or more CLL-1 VHH DARIC components, CLL-1 VHH DARIC receptors, anti-CLL-1 VHH CARs, fusion polypeptides, and expression vectors, viral vectors, and transfer plasmids comprising polynucleotides contemplated herein.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion, substitution, or modification of at least one nucleotide. Accordingly, the terms "polynucleotide variant" and "variant" include polynucleotides in which one or more nucleotides have been added or deleted, or modified, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 86%, 97%, 98%, or 99% sequence identity to any of the reference sequences described herein.

The polynucleotides contemplated herein, regardless of the length of the coding sequence itself, may be combined with other DNA sequences, such as promoters and/or enhancers, untranslated regions (UTRs), signal sequences, Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, and polynucleotides encoding self-cleaving polypeptides, epitope tags, as disclosed elsewhere herein or as known in the art, such that their overall length may vary considerably. It is therefore contemplated that a polynucleotide fragment of almost any length may be employed, with the total length preferably being limited by the ease of preparation and use in the intended recombinant DNA protocol.

Polynucleotides can be prepared, manipulated, expressed and/or delivered using any of a variety of well-established techniques known and available in the art. In order to express a desired polypeptide, a nucleotide sequence encoding the polypeptide, can be inserted into appropriate vector.

Illustrative examples of vectors include, but are not limited to plasmid, autonomously replicating sequences, and transposable elements, e.g., Sleeping Beauty, PiggyBac.

Additional illustrative examples of vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses.

Illustrative examples of viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40).

Illustrative examples of expression vectors include, but are not limited to, pClneo vectors (Promega) for expression in mammalian cells; pLenti4/V5-DESTT$^M$, pLenti6/V5-DESTT$^M$, and pLenti6.2/V5-GW/lacZ (Invitrogen) for lentivirus-mediated gene transfer and expression in mammalian cells. In particular embodiments, coding sequences of polypeptides disclosed herein can be ligated into such expression vectors for the expression of the polypeptides in mammalian cells.

In particular embodiments, the vector is an episomal vector or a vector that is maintained extrachromosomally. As used herein, the term "episomal" refers to a vector that is able to replicate without integration into host's chromosomal DNA and without gradual loss from a dividing host cell also meaning that said vector replicates extrachromosomally or episomally. "Expression control sequences," "control elements," or "regulatory sequences" present in an expression vector are those non-translated regions of the vector including an origin of replication, selection cassettes, promoters, enhancers, translation initiation signals (Shine Dalgarno sequence or Kozak sequence) introns, a polyadenylation sequence, 5' and 3' untranslated regions, all of which interact with host cellular proteins to carry out transcription and translation. Such elements may vary in their strength and specificity. Depending on the vector system and host utilized, any number of suitable transcription and translation elements, including ubiquitous promoters and inducible promoters may be used.

In particular embodiments, a polynucleotide comprises a vector, including but not limited to expression vectors and viral vectors. A vector may comprise one or more exogenous, endogenous, or heterologous control sequences such as promoters and/or enhancers. An "endogenous control sequence" is one which is naturally linked with a given gene in the genome. An "exogenous control sequence" is one which is placed in juxtaposition to a gene by means of genetic manipulation (i.e., molecular biological techniques) such that transcription of that gene is directed by the linked enhancer/promoter. A "heterologous control sequence" is an exogenous sequence that is from a different species than the cell being genetically manipulated. A "synthetic" control sequence may comprise elements of one more endogenous and/or exogenous sequences, and/or sequences determined in vitro or in silico that provide optimal promoter and/or enhancer activity for the particular therapy.

The term "promoter" as used herein refers to a recognition site of a polynucleotide (DNA or RNA) to which an RNA polymerase binds. An RNA polymerase initiates and transcribes polynucleotides operably linked to the promoter. In particular embodiments, promoters operative in mammalian cells comprise an AT-rich region located approximately 25 to 30 bases upstream from the site where transcription is initiated and/or another sequence found 70 to 80 bases upstream from the start of transcription, a CNCAAT region where N may be any nucleotide.

The term "enhancer" refers to a segment of DNA which contains sequences capable of providing enhanced transcription and in some instances can function independent of their orientation relative to another control sequence. An enhancer can function cooperatively or additively with promoters and/or other enhancer elements. The term "promoter/enhancer" refers to a segment of DNA which contains sequences capable of providing both promoter and enhancer functions.

The term "operably linked", refers to a juxtaposition wherein the components described are in a relationship permitting them to function in their intended manner. In one embodiment, the term refers to a functional linkage between a nucleic acid expression control sequence (such as a promoter, and/or enhancer) and a second polynucleotide sequence, e.g., a polynucleotide-of-interest, wherein the expression control sequence directs transcription of the nucleic acid corresponding to the second sequence.

As used herein, the term "constitutive expression control sequence" refers to a promoter, enhancer, or promoter/enhancer that continually or continuously allows for transcription of an operably linked sequence. A constitutive expression control sequence may be a "ubiquitous" promoter, enhancer, or promoter/enhancer that allows expression in a wide variety of cell and tissue types or a "cell specific," "cell type specific," "cell lineage specific," or "tissue specific" promoter, enhancer, or promoter/enhancer that allows expression in a restricted variety of cell and tissue types, respectively.

Illustrative ubiquitous expression control sequences suitable for use in particular embodiments include, but are not limited to, a cytomegalovirus (CMV) immediate early promoter, a viral simian virus 40 (SV40) (e.g., early or late), a Moloney murine leukemia virus (MoMLV) LTR promoter, a Rous sarcoma virus (RSV) LTR, a herpes simplex virus (HSV) (thymidine kinase) promoter, H5, P7.5, and P11 promoters from vaccinia virus, an elongation factor 1-alpha (EF1a) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus (Irions et al., *Nature Biotechnology* 25, 1477-1482 (2007)), a Ubiquitin C promoter (UBC), a phosphoglycerate kinase-1 (PGK) promoter, a cytomegalovirus enhancer/chicken β-actin (CAG) promoter, a β-actin promoter and a myeloproliferative sarcoma virus enhancer, negative control region deleted, dl587rev primer-binding site substituted (MND) U3 promoter (Haas et al. *Journal of Virology*. 2003; 77(17): 9439-9450).

In one embodiment, a vector comprises an MNDU3 promoter.

In one embodiment, a vector comprises an EF1a promoter comprising the first intron of the human EF1a gene.

In one embodiment, a vector comprises an EF1a promoter that lacks the first intron of the human EF1a gene.

In a particular embodiment, it may be desirable to use a cell, cell type, cell lineage or tissue specific expression control sequence to achieve cell type specific, lineage specific, or tissue specific expression of a desired polynucleotide sequence (e.g., to express a particular nucleic acid encoding a polypeptide in only a subset of cell types, cell lineages, or tissues or during specific stages of development).

In a particular embodiment, it may be desirable to express a polynucleotide a T cell specific promoter.

As used herein, "conditional expression" may refer to any type of conditional expression including, but not limited to, inducible expression; repressible expression; expression in cells or tissues having a particular physiological, biological, or disease state, etc. This definition is not intended to exclude cell type or tissue specific expression. Certain embodiments provide conditional expression of a polynucleotide-of-interest, e.g., expression is controlled by subjecting a cell, tissue, organism, etc., to a treatment or condition that causes the polynucleotide to be expressed or that causes an increase or decrease in expression of the polynucleotide encoded by the polynucleotide-of-interest.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, *Gene*, 323:67), the cumate inducible gene switch (WO 2002/088346), tetracycline-dependent regulatory systems, etc.

Inducer agents include, but are not limited to glucocorticoids, estrogens, mifepristone (RU486), metals, interferons, small molecules, cumate, tetracycline, doxycycline, and variants thereof.

As used herein, an "internal ribosome entry site" or "IRES" refers to an element that promotes direct internal ribosome entry to the initiation codon, such as ATG, of a cistron (a protein encoding region), thereby leading to the cap-independent translation of the gene. See, e.g., Jackson et al., 1990. *Trends Biochem Sci* 15(12):477-83) and Jackson and Kaminski. 1995. *RNA* 1(10):985-1000. Examples of IRES generally employed by those of skill in the art include those described in U.S. Pat. No. 6,692,736. Further examples of "IRES" known in the art include but are not limited to IRES obtainable from picornavirus (Jackson et al., 1990) and IRES obtainable from viral or cellular mRNA sources, such as for example, immunoglobulin heavy-chain binding protein (BiP), the vascular endothelial growth factor (VEGF) (Huez et al. 1998. *Mol. Cell. Biol.* 18(11):6178-6190), the fibroblast growth factor 2 (FGF-2), and insulin-like growth factor (IGFII), the translational initiation factor eIF4G and yeast transcription factors TFIID and HAP4, the encephelomycarditis virus (EMCV) which is commercially available from Novagen (Duke et al., 1992. J. Virol 66(3): 1602-9) and the VEGF IRES (Huez et al., 1998. Mol Cell Biol 18(11):6178-90). IRES have also been reported in viral genomes of Picornaviridae, Dicistroviridae and Flaviviridae species and in HCV, Friend murine leukemia virus (FrMLV) and Moloney murine leukemia virus (MoMLV).

In one embodiment, the IRES used in polynucleotides contemplated herein is an EMCV IRES.

In particular embodiments, the polynucleotides a consensus Kozak sequence. As used herein, the term "Kozak sequence" refers to a short nucleotide sequence that greatly facilitates the initial binding of mRNA to the small subunit of the ribosome and increases translation. The consensus Kozak sequence is (GCC)RCCATGG (SEQ ID NO: 51), where R is a purine (A or G) (Kozak, 1986. *Cell*. 44(2): 283-92, and Kozak, 1987. *Nucleic Acids Res*. 15(20):8125-48).

Elements directing the efficient termination and polyadenylation of the heterologous nucleic acid transcripts increases heterologous gene expression. Transcription termination signals are generally found downstream of the polyadenylation signal. In particular embodiments, vectors comprise a polyadenylation sequence 3' of a polynucleotide encoding a polypeptide to be expressed. The term "polyA site" or "polyA sequence" as used herein denotes a DNA sequence which directs both the termination and polyadenylation of the nascent RNA transcript by RNA polymerase II. Polyadenylation sequences can promote mRNA stability by addition of a polyA tail to the 3' end of the coding sequence and thus, contribute to increased translational efficiency. Cleavage and polyadenylation are directed by a poly(A) sequence in the RNA. The core poly(A) sequence for mammalian pre-mRNAs has two recognition elements flanking a cleavage-polyadenylation site. Typically, an almost invariant AAUAAA hexamer lies 20-50 nucleotides upstream of a more variable element rich in U or GU residues. Cleavage of the nascent transcript occurs between these two elements and is coupled to the addition of up to 250 adenosines to the 5' cleavage product. In particular embodiments, the core poly(A) sequence is an ideal polyA sequence (e.g., AATAAA, ATTAAA, AGTAAA). In particular embodiments, the poly(A) sequence is an SV40 polyA sequence, a bovine growth hormone polyA sequence (BGHpA), a rabbit β-globin polyA sequence (rβgpA), variants thereof, or another suitable heterologous or endogenous polyA sequence known in the art. In particular embodiments, the poly(A) sequence is synthetic.

In particular embodiments, polynucleotides encoding one or more polypeptides, or fusion polypeptides may be introduced into immune effector cells, e.g., T cells, by both non-viral and viral methods. In particular embodiments, delivery of one or more polynucleotides may be provided by the same method or by different methods, and/or by the same vector or by different vectors.

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. In particular embodiments, non-viral vectors are used to deliver one or more polynucleotides contemplated herein to a T cell.

Illustrative examples of non-viral vectors include, but are not limited to plasmids (e.g., DNA plasmids or RNA plasmids), transposons, cosmids, and bacterial artificial chromosomes.

Illustrative methods of non-viral delivery of polynucleotides contemplated in particular embodiments include, but are not limited to: electroporation, sonoporation, lipofection, microinjection, biolistics, virosomes, liposomes, immunoliposomes, nanoparticles, polycation or lipid:nucleic acid conjugates, naked DNA, artificial virions, DEAE-dextran-mediated transfer, gene gun, and heat-shock.

Illustrative examples of polynucleotide delivery systems suitable for use in particular embodiments contemplated in particular embodiments include, but are not limited to those provided by Amaxa Biosystems, Maxcyte, Inc., BTX Molecular Delivery Systems, and Copernicus Therapeutics Inc. Lipofection reagents are sold commercially (e.g., Transfectam™ and Lipofectin™). Cationic and neutral lipids that are suitable for efficient receptor-recognition lipofection of polynucleotides have been described in the literature. See e.g., Liu et al. (2003) Gene Therapy. 10:180-187; and Balazs et al. (2011) Journal of Drug Delivery. 2011:1-12. Antibody-targeted, bacterially derived, non-living nanocell-based delivery is also contemplated in particular embodiments.

Viral vectors comprising polynucleotides contemplated in particular embodiments can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., mobilized peripheral blood, lymphocytes, bone marrow aspirates, tissue biopsy, etc.) or universal donor hematopoietic stem cells, followed by reimplantation of the cells into a patient.

In one embodiment, viral vectors comprising polynucleotides contemplated herein are administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Illustrative examples of viral vector systems suitable for use in particular embodiments contemplated in particular embodiments include, but are not limited to, adeno-associated virus (AAV), retrovirus, herpes simplex virus, adenovirus, and vaccinia virus vectors.

In various embodiments, one or more polynucleotides encoding one or more CLL-1 VHH DARIC components and/or other polypeptides contemplated herein are introduced into an immune effector cell, e.g., T cell, by transducing the cell with a recombinant adeno-associated virus (rAAV), comprising the one or more polynucleotides.

AAV is a small (~26 nm) replication-defective, primarily episomal, non-enveloped virus. AAV can infect both dividing and non-dividing cells and may incorporate its genome into that of the host cell. Recombinant AAV (rAAV) are typically composed of, at a minimum, a transgene and its regulatory sequences, and 5' and 3' AAV inverted terminal repeats (ITRs). The ITR sequences are about 145 bp in length. In particular embodiments, the rAAV comprises ITRs and capsid sequences isolated from AAV1, AAV2, AAV3, AAV4, AAV5, AAV6, AAV7, AAV8, AAV9, or AAV10.

In some embodiments, a chimeric rAAV is used the ITR sequences are isolated from one AAV serotype and the capsid sequences are isolated from a different AAV serotype. For example, a rAAV with ITR sequences derived from AAV2 and capsid sequences derived from AAV6 is referred to as AAV2/AAV6. In particular embodiments, the rAAV vector may comprise ITRs from AAV2, and capsid proteins from any one of AAV1, AAV2, AAV3, AAV4, AAV5, AAV6, AAV7, AAV8, AAV9, or AAV10. In a preferred embodiment, the rAAV comprises ITR sequences derived from AAV2 and capsid sequences derived from AAV6. In a preferred embodiment, the rAAV comprises ITR sequences derived from AAV2 and capsid sequences derived from AAV2.

In some embodiments, engineering and selection methods can be applied to AAV capsids to make them more likely to transduce cells of interest.

Construction of rAAV vectors, production, and purification thereof have been disclosed, e.g., in U.S. Pat. Nos. 9,169,494; 9,169,492; 9,012,224; 8,889,641; 8,809,058; and 8,784,799, each of which is incorporated by reference herein, in its entirety.

In various embodiments, one or more polynucleotides encoding one or more CLL-1 VHH DARIC components and/or other polypeptides contemplated herein are introduced into an immune effector cell, e.g., T cell, by transducing the cell with a retrovirus, e.g., lentivirus, comprising the one or more polynucleotides.

As used herein, the term "retrovirus" refers to an RNA virus that reverse transcribes its genomic RNA into a linear double-stranded DNA copy and subsequently covalently integrates its genomic DNA into a host genome. Illustrative retroviruses suitable for use in particular embodiments, include, but are not limited to: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and lentivirus.

As used herein, the term "lentivirus" refers to a group (or genus) of complex retroviruses. Illustrative lentiviruses include, but are not limited to, HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one embodiment, HIV based vector backbones (i.e., HIV cis-acting sequence elements) are preferred.

In various embodiments, a lentiviral vector contemplated herein comprises one or more LTRs, and one or more, or all, of the following accessory elements: a cPPT/FLAP, a Psi (Ψ) packaging signal, an export element, poly (A) sequences, and may optionally comprise a WPRE or HPRE, an insulator element, a selectable marker, and a cell suicide gene, as discussed elsewhere herein.

In particular embodiments, lentiviral vectors contemplated herein may be integrative or non-integrating or integration defective lentivirus. As used herein, the term "integration defective lentivirus" or "IDLV" refers to a lentivirus having an integrase that lacks the capacity to integrate the viral genome into the genome of the host cells. Integration-incompetent viral vectors have been described in patent application WO 2006/010834, which is herein incorporated by reference in its entirety.

Illustrative mutations in the HIV-1 pol gene suitable to reduce integrase activity include, but are not limited to: H12N, H12C, H16C, H16V, S81 R, D41A, K42A, H51A, Q53C, D55V, D64E, D64V, E69A, K71A, E85A, E87A, D116N, D116I, D116A, N120G, N120I, N120E, E152G, E152A, D35E, K156E, K156A, E157A, K159E, K159A, K160A, R166A, D167A, E170A, H171A, K173A, K186Q, K186T, K188T, E198A, R199c, R199T, R199A, D202A, K211A, Q214L, Q216L, Q221 L, W235F, W235E, K236S, K236A, K246A, G247W, D253A, R262A, R263A and K264H.

The term "long terminal repeat (LTR)" refers to domains of base pairs located at the ends of retroviral DNAs which, in their natural sequence context, are direct repeats and contain U3, R and U5 regions.

As used herein, the term "FLAP element" or "cPPT/FLAP" refers to a nucleic acid whose sequence includes the central polypurine tract and central termination sequences (cPPT and CTS) of a retrovirus, e.g., HIV-1 or HIV-2. Suitable FLAP elements are described in U.S. Pat. No. 6,682,907 and in Zennou, et al., 2000, Cell, 101:173.

As used herein, the term "packaging signal" or "packaging sequence" refers to psi [Ψ] sequences located within the retroviral genome which are required for insertion of the viral RNA into the viral capsid or particle, see e.g., Clever et al., 1995. J. of Virology, Vol. 69, No. 4; pp. 2101-2109.

The term "export element" refers to a cis-acting post-transcriptional regulatory element which regulates the transport of an RNA transcript from the nucleus to the cytoplasm of a cell. Examples of RNA export elements include, but are not limited to, the human immunodeficiency virus (HIV) rev response element (RRE) (see e.g., Cullen et al., 1991. J. Virol. 65: 1053; and Cullen et al., 1991. Cell 58: 423), and the hepatitis B virus post-transcriptional regulatory element (HPRE).

In particular embodiments, expression of heterologous sequences in viral vectors is increased by incorporating posttranscriptional regulatory elements, efficient polyadenylation sites, and optionally, transcription termination signals into the vectors. A variety of posttranscriptional regulatory elements can increase expression of a heterologous nucleic acid at the protein, e.g., woodchuck hepatitis virus posttranscriptional regulatory element (WPRE; Zufferey et al., 1999, J. Virol., 73:2886); the posttranscriptional regulatory element present in hepatitis B virus (HPRE) (Huang et al., Mol. Cell. Biol., 5:3864); and the like (Liu et al., 1995, Genes Dev., 9:1766).

Lentiviral vectors preferably contain several safety enhancements as a result of modifying the LTRs. "Self-inactivating" (SIN) vectors refers to replication-defective vectors, e.g., retroviral or lentiviral vectors, in which the right (3') LTR enhancer-promoter region, known as the U3 region, has been modified (e.g., by deletion or substitution) to prevent viral transcription beyond the first round of viral replication. Self-inactivation is preferably achieved through in the introduction of a deletion in the U3 region of the 3' LTR of the vector DNA, i.e., the DNA used to produce the vector RNA. Thus, during reverse transcription, this deletion is transferred to the 5' LTR of the proviral DNA. In particular embodiments, it is desirable to eliminate enough of the U3 sequence to greatly diminish or abolish altogether the transcriptional activity of the LTR, thereby greatly diminishing or abolishing the production of full-length vector RNA in transduced cells. In the case of HIV based lentivectors, it has been discovered that such vectors tolerate significant U3 deletions, including the removal of the LTR TATA box (e.g., deletions from −418 to −18), without significant reductions in vector titers.

An additional safety enhancement is provided by replacing the U3 region of the 5' LTR with a heterologous promoter to drive transcription of the viral genome during production of viral particles. Examples of heterologous promoters which can be used include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters.

The terms "pseudotype" or "pseudotyping" as used herein, refer to a virus whose viral envelope proteins have been substituted with those of another virus possessing preferable characteristics. For example, HIV can be pseudo-typed with vesicular stomatitis virus G-protein (VSV-G) envelope proteins, which allows HIV to infect a wider range of cells because HIV envelope proteins (encoded by the env gene) normally target the virus to CD4+ presenting cells.

In certain embodiments, lentiviral vectors are produced according to known methods. See e.g., Kutner et al., BMC Biotechnol. 2009; 9:10. doi: 10.1186/1472-6750-9-10; Kutner et al. Nat. Protoc. 2009; 4(4):495-505. doi: 10.1038/nprot.2009.22.

According to certain specific embodiments contemplated herein, most or all of the viral vector backbone sequences are derived from a lentivirus, e.g., HIV-1. However, it is to be understood that many different sources of retroviral and/or lentiviral sequences can be used, or combined and numerous substitutions and alterations in certain of the lentiviral sequences may be accommodated without impairing the ability of a transfer vector to perform the functions described herein. Moreover, a variety of lentiviral vectors are known in the art, see Naldini et al., (1996a, 1996b, and 1998); Zufferey et al., (1997); Dull et al., 1998, U.S. Pat. Nos. 6,013,516; and 5,994,136, many of which may be adapted to produce a viral vector or transfer plasmid contemplated herein.

In various embodiments, one or more polynucleotides encoding one or more CLL-1 VHH DARIC components and/or other polypeptides contemplated herein are introduced into an immune effector cell, by transducing the cell with an adenovirus comprising the one or more polynucleotides.

Adenoviral based vectors are capable of very high transduction efficiency in many cell types and do not require cell division. With such vectors, high titer and high levels of expression have been obtained. This vector can be produced in large quantities in a relatively simple system. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity.

Generation and propagation of the current adenovirus vectors, which are replication deficient, may utilize a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones & Shenk, 1978), the current adenovirus vectors, with the help of 293 cells, carry foreign DNA in either the E1, the D3 or both regions (Graham & Prevec, 1991). Adenovirus vectors have been used in eukaryotic gene expression (Levrero et al., 1991; Gomez-Foix et al., 1992) and vaccine development (Grunhaus & Horwitz, 1992; Graham & Prevec, 1992). Studies in administering recombinant adenovirus to different tissues include trachea instillation (Rosenfeld et al., 1991; Rosenfeld et al., 1992), muscle injection (Ragot et al., 1993), peripheral intravenous injections (Herz & Gerard, 1993) and stereotactic inoculation into the brain (Le Gal La Salle et al., 1993). An example of the use of an Ad vector in a clinical trial involved polynucleotide therapy for antitumor immunization with intramuscular injection (Sterman et al., *Hum. Gene Ther.* 7:1083-9 (1998)).

In various embodiments, one or more polynucleotides encoding one or more CLL-1 VHH DARIC components and/or other polypeptides contemplated herein are introduced into an immune effector cell by transducing the cell with a herpes simplex virus, e.g., HSV-1, HSV-2, comprising the one or more polynucleotides.

The mature HSV virion consists of an enveloped icosahedral capsid with a viral genome consisting of a linear double-stranded DNA molecule that is 152 kb. In one embodiment, the HSV based viral vector is deficient in one or more essential or non-essential HSV genes. In one embodiment, the HSV based viral vector is replication deficient. Most replication deficient HSV vectors contain a deletion to remove one or more intermediate-early, early, or late HSV genes to prevent replication. For example, the HSV vector may be deficient in an immediate early gene selected from the group consisting of ICP4, ICP22, ICP27, ICP47, and a combination thereof. Advantages of the HSV vector are its ability to enter a latent stage that can result in long-term DNA expression and its large viral DNA genome that can accommodate exogenous DNA inserts of up to 25 kb. HSV-based vectors are described in, for example, U.S. Pat. Nos. 5,837,532, 5,846,782, and 5,804,413, and International Patent Applications WO 91/02788, WO 96/04394, WO 98/15637, and WO 99/06583, each of which are incorporated by reference herein in its entirety.

G. Genetically Modified Cells

In various embodiments, cells are modified to express a CLL-1 VHH DARIC, one or more CLL-1 VHH DARIC components, an anti-CLL-1 VHH CAR, and/or fusion proteins contemplated herein, for use in the treatment of cancer. Cells may be non-genetically modified to express one or more of the polypeptides contemplated herein, or in particular preferred embodiments, cells may be genetically modified to express one or more of the polypeptides contemplated herein. As used herein, the term "genetically engineered" or "genetically modified" refers to the addition of extra genetic material in the form of DNA or RNA into the total genetic material in a cell. The terms, "genetically modified cells," "modified cells," and "redirected cells," are used interchangeably in particular embodiments.

In particular embodiments, one or more CLL-1 VHH DARIC components or an anti-CLL-1 VHH CAR contemplated herein are introduced and expressed in immune effector cells to improve the efficacy of the immune effector cells.

An "immune effector cell," is any cell of the immune system that has one or more effector functions (e.g., cytotoxic cell killing activity, secretion of cytokines, induction of ADCC and/or CDC). The illustrative immune effector cells contemplated herein are T lymphocytes, including but not limited to cytotoxic T cells (CTLs; $CD8^+$ T cells), TILs, and helper T cells (HTLs; $CD4^+$ T cells). In a particular embodiment, the cells comprise $\alpha\beta$ T cells. In a particular embodiment, the cells comprise $\gamma\delta$ T cells. In one embodiment, immune effector cells include natural killer (NK) cells. In one embodiment, immune effector cells include natural killer T (NKT) cells. Immune effector cells can be autologous/autogeneic ("self") or non-autologous ("non-self," e.g., allogeneic, syngeneic or xenogeneic).

"Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In preferred embodiments, the cells are human autologous immune effector cells.

Illustrative immune effector cells suitable for introducing one or more CLL-1 VHH DARIC components or an anti-CLL-1 VHH CAR contemplated herein include T lymphocytes. The terms "T cell" or "T lymphocyte" are art-recognized and are intended to include thymocytes, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a helper T cell (HTL; $CD4^+$ T cell), a cytotoxic T cell (CTL; $CD8^+$ T cell), $CD4^+CD8^+$ T cell, $CD4^-CD8^-$ T cell, or any other subset of T cells. Other illustrative populations of T cells suitable for use in particular embodiments include naïve T cells and memory T cells.

As would be understood by the skilled person, other cells may also be used as immune effector cells comprising one or more CLL-1 VHH DARIC components or an anti-CLL-1 VHH CAR contemplated herein. In particular embodiments, immune effector cells also include NK cells, NKT cells, neutrophils, and macrophages. Immune effector cells also include progenitors of effector cells wherein such progenitor cells can be induced to differentiate into immune effector cells in vivo or in vitro. Thus, in particular embodiments, immune effector cells include progenitors of immune effectors cells such as hematopoietic stem cells (HSCs) contained within the $CD34^+$ population of cells derived from cord blood, bone marrow or mobilized peripheral blood which upon administration in a subject differentiate into mature immune effector cells, or which can be induced in vitro to differentiate into mature immune effector cells.

The term, "CD34+ cell," as used herein refers to a cell expressing the CD34 protein on its cell surface. "CD34," as used herein refers to a cell surface glycoprotein (e.g., sialomucin protein) that often acts as a cell-cell adhesion factor and is involved in T cell entrance into lymph nodes. The CD34+ cell population contains hematopoietic stem cells (HSC), which upon administration to a patient differentiate and contribute to all hematopoietic lineages, including T cells, NK cells, NKT cells, neutrophils and cells of the monocyte/macrophage lineage.

Methods for making the immune effector cells which express one or more CLL-1 VHH DARIC components or an anti-CLL-1 VHH CAR contemplated herein are provided in particular embodiments. In one embodiment, the method comprises transfecting or transducing immune effector cells isolated from an individual such that the immune effector cells with one or more nucleic acids and/or vectors, e.g., a lentiviral vector comprising a nucleic acid encoding one or more CLL-1 VHH DARIC components or an anti-CLL-1 VHH CAR contemplated herein. In one embodiment, the method comprises transfecting or transducing immune effector cells isolated from an individual such that the immune effector cells express one or more CLL-1 VHH DARIC components or an anti-CLL-1 VHH CAR contemplated herein. In certain embodiments, the immune effector cells are isolated from an individual and genetically modified without further manipulation in vitro. Such cells can then be directly re-administered into the individual. In further embodiments, the immune effector cells are first activated and stimulated to proliferate in vitro prior to being genetically modified. In this regard, the immune effector cells may be cultured before and/or after being genetically modified.

In particular embodiments, prior to in vitro manipulation or genetic modification of the immune effector cells described herein, the source of cells is obtained from a subject. In particular embodiments, the modified immune effector cells comprise T cells.

T cells can be obtained from a number of sources including, but not limited to, peripheral blood mononuclear cells, bone marrow, lymph nodes tissue, cord blood, thymus issue, tissue from a site of infection, ascites, pleural effusion, spleen tissue, and tumors. In certain embodiments, T cells can be obtained from a unit of blood collected from a subject using any number of techniques known to the skilled person, such as sedimentation, e.g., FICOLL™ separation.

In other embodiments, an isolated or purified population of T cells is used. In some embodiments, after isolation of PBMC, both cytotoxic and helper T lymphocytes can be sorted into naïve, memory, and effector T cell subpopulations either before or after activation, expansion, and/or genetic modification.

In one embodiment, an isolated or purified population of T cells expresses one or more of the markers including, but not limited to a CD3+, CD4+, CD8+, or a combination thereof.

In certain embodiments, the T cells are isolated from an individual and first activated and stimulated to proliferate in vitro prior to being modified to express one or more CLL-1 VHH DARIC components or an anti-CLL-1 VHH CAR.

In order to achieve sufficient therapeutic doses of T cell compositions, T cells are often subjected to one or more rounds of stimulation, activation and/or expansion. In particular embodiments, T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; and 6,867,041, each of which is incorporated herein by reference in its entirety. In particular embodiments, T cells are activated and expanded for about 6 hours, about 12 hours, about 18 hours or about 24 hours prior to introduction of vectors or polynucleotides encoding one or more CLL-1 VHH DARIC components or an anti-CLL-1 VHH CAR contemplated herein.

H. Compositions and Formulations

The compositions contemplated herein may comprise one or more CLL-1 VHH DARIC components or an anti-CLL-1 VHH CAR, polynucleotides encoding one or more CLL-1 VHH DARIC components or an anti-CLL-1 VHH CAR, vectors comprising same, genetically modified immune effector cells, bridging factors, etc. Compositions include, but are not limited to, pharmaceutical compositions. A "pharmaceutical composition" refers to a composition formulated in pharmaceutically-acceptable or physiologically-acceptable solutions for administration to a cell or an animal, either alone, or in combination with one or more other modalities of therapy. It will also be understood that, if desired, the compositions may be administered in combination with other agents as well, such as, e.g., cytokines, growth factors, hormones, small molecules, chemotherapeutics, pro-drugs, drugs, antibodies, or other various pharmaceutically-active agents. There is virtually no limit to other components that may also be included in the compositions, provided that the additional agents do not adversely affect the ability of the composition to deliver the intended therapy.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable carrier" refers to a diluent, adjuvant, excipient, or vehicle with which the bridging factors, polypeptides, polynucleotides, vectors comprising same, or genetically modified immune effector cells are administered. Illustrative examples of pharmaceutical carriers can be sterile liquids, such as cell culture media, water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients in particular embodiments, include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Except insofar as any conventional media or agent is incompatible with the active ingredient, its use in the therapeutic compositions is contemplated. Supplementary active ingredients can also be incorporated into the compositions.

In one embodiment, a composition comprising a pharmaceutically acceptable carrier is suitable for administration to a subject. In particular embodiments, a composition comprising a carrier is suitable for parenteral administration, e.g., intravascular (intravenous or intraarterial), intraperitoneal or intramuscular administration. In particular embodiments, a composition comprising a pharmaceutically acceptable carrier is suitable for intraventricular, intraspinal, or intrathecal administration. Pharmaceutically acceptable carriers include sterile aqueous solutions, cell culture media, or dispersions. The use of such media and agents for pharmaceutically active substances is well known in the art. Except insofar as any conventional media or agent is incompatible with the bridging factors, polypeptides, polynucleotides, vectors comprising same, or genetically modified immune effector cells, use thereof in the pharmaceutical compositions is contemplated.

In particular embodiments, compositions contemplated herein comprise genetically modified T cells and a pharmaceutically acceptable carrier. A composition comprising a cell-based composition contemplated herein can be administered separately by enteral or parenteral administration methods or in combination with other suitable compounds to effect the desired treatment goals.

In particular embodiments, compositions contemplated herein comprise a bridging factor and a pharmaceutically acceptable carrier.

The pharmaceutically acceptable carrier must be of sufficiently high purity and of sufficiently low toxicity to render it suitable for administration to the human subject being treated. It further should maintain or increase the stability of the composition. The pharmaceutically acceptable carrier can be liquid or solid and is selected, with the planned manner of administration in mind, to provide for the desired bulk, consistency, etc., when combined with other components of the composition. For example, the pharmaceutically acceptable carrier can be, without limitation, a binding agent (e.g., pregelatinized maize starch, polyvinylpyrrolidone or hydroxypropyl methylcellulose, etc.), a filler (e.g., lactose and other sugars, microcrystalline cellulose, pectin, gelatin, calcium sulfate, ethyl cellulose, polyacrylates, calcium hydrogen phosphate, etc.), a lubricant (e.g., magnesium stearate, talc, silica, colloidal silicon dioxide, stearic acid, metallic stearates, hydrogenated vegetable oils, corn starch, polyethylene glycols, sodium benzoate, sodium acetate, etc.), a disintegrant (e.g., starch, sodium starch glycolate, etc.), or a wetting agent (e.g., sodium lauryl sulfate, etc.). Other suitable pharmaceutically acceptable carriers for the compositions contemplated herein include, but are not limited to, water, salt solutions, alcohols, polyethylene glycols, gelatins, amyloses, magnesium stearates, talcs, silicic acids, viscous paraffins, hydroxymethylcelluloses, polyvinylpyrrolidones and the like.

Such carrier solutions also can contain buffers, diluents and other suitable additives. The term "buffer" as used herein refers to a solution or liquid whose chemical makeup neutralizes acids or bases without a significant change in pH. Examples of buffers contemplated herein include, but are not limited to, Dulbecco's phosphate buffered saline (PBS), Ringer's solution, 5% dextrose in water (D5W), normal/physiologic saline (0.9% NaCl).

The pharmaceutically acceptable carriers may be present in amounts sufficient to maintain a pH of the composition of about 7. Alternatively, the composition has a pH in a range from about 6.8 to about 7.4, e.g., 6.8, 6.9, 7.0, 7.1, 7.2, 7.3, and 7.4. In still another embodiment, the composition has a pH of about 7.4.

Compositions contemplated herein may comprise a nontoxic pharmaceutically acceptable medium. The compositions may be a suspension. The term "suspension" as used herein refers to non-adherent conditions in which cells are not attached to a solid support. For example, cells maintained as a suspension may be stirred or agitated and are not adhered to a support, such as a culture dish.

In particular embodiments, compositions contemplated herein are formulated in a suspension, where the modified T cells are dispersed within an acceptable liquid medium or solution, e.g., saline or serum-free medium, in an intravenous (IV) bag or the like. Acceptable diluents include, but are not limited to water, PlasmaLyte®, Ringer's solution, isotonic sodium chloride (saline) solution, serum-free cell culture medium, and medium suitable for cryogenic storage, e.g., Cryostor® medium.

In certain embodiments, a pharmaceutically acceptable carrier is substantially free of natural proteins of human or animal origin, and suitable for storing a composition comprising a population of modified T cells. The therapeutic composition is intended to be administered into a human patient, and thus is substantially free of cell culture components such as bovine serum albumin, horse serum, and fetal bovine serum.

In some embodiments, compositions are formulated in a pharmaceutically acceptable cell culture medium. Such compositions are suitable for administration to human subjects. In particular embodiments, the pharmaceutically acceptable cell culture medium is a serum free medium.

Serum-free medium has several advantages over serum containing medium, including a simplified and better-defined composition, a reduced degree of contaminants, elimination of a potential source of infectious agents, and lower cost. In various embodiments, the serum-free medium is animal-free, and may optionally be protein-free. Optionally, the medium may contain biopharmaceutically acceptable recombinant proteins. "Animal-free" medium refers to medium wherein the components are derived from non-animal sources. Recombinant proteins replace native animal proteins in animal-free medium and the nutrients are obtained from synthetic, plant or microbial sources. "Protein-free" medium, in contrast, is defined as substantially free of protein.

Illustrative examples of serum-free media used in particular compositions includes, but is not limited to, QBSF-60® (Quality Biological, Inc.), StemPro®-34 (Life Technologies), and X-VIVO® 10.

In one embodiment, the compositions comprising modified T cells are formulated in PlasmaLyte®.

In various embodiments, compositions comprising modified T cells are formulated in a cryopreservation medium. For example, cryopreservation media with cryopreservation agents may be used to maintain a high cell viability outcome post-thaw. Illustrative examples of cryopreservation media used in particular compositions includes, but is not limited to, CryoStor® CS10, CryoStor® CS5, and CryoStor® CS2.

In one embodiment, the compositions are formulated in a solution comprising 50:50 PlasmaLyte® A to CryoStor® CS10.

In particular embodiments, the composition is substantially free of *mycoplasma*, endotoxin, and microbial contamination. By "substantially free" with respect to endotoxin is meant that there is less endotoxin per dose of cells than is allowed by the FDA for a biologic, which is a total endotoxin of 5 EU/kg body weight per day, which for an average 70 kg person is 350 EU per total dose of cells. In particular embodiments, compositions contemplated herein contain about 0.5 EU/ml to about 5.0 EU/ml, or about 0.5 EU/ml, 1.0 EU/ml, 1.5 EU/ml, 2.0 EU/ml, 2.5 EU/ml, 3.0 EU/ml, 3.5 EU/ml, 4.0 EU/ml, 4.5 EU/ml, or 5.0 EU/ml.

In particular embodiments, formulation of pharmaceutically-acceptable carrier solutions is well-known to those of skill in the art, as is the development of suitable dosing and treatment regimens for using the particular compositions described herein in a variety of treatment regimens, including e.g., enteral and parenteral, e.g., intravascular, intravenous, intrarterial, intraosseously, intraventricular, intracerebral, intracranial, intraspinal, intrathecal, and intramedullary administration and formulation. It would be understood by the skilled artisan that particular embodiments contemplated herein may comprise other formulations, such as those that are well known in the pharmaceutical art, and are described, for example, in *Remington: The Science and Practice of Pharmacy*, volume I and volume II. $22^{nd}$ Edition. Edited by Loyd V. Allen Jr. Philadelphia, PA: Pharmaceutical Press; 2012, which is incorporated by reference herein, in its entirety.

In particular embodiments, compositions comprise an amount of immune effector cells comprising a polynucleotide encoding one or more CLL-1 VHH DARIC components or an anti-CLL-1 VHH CAR contemplated herein. In particular embodiments, compositions comprise an amount of immune effector cells that express one or more CLL-1 VHH DARIC components or an anti-CLL-1 VHH CAR contemplated herein. As used herein, the term "amount" refers to "an amount effective" or "an effective amount" of cells comprising one or more CLL-1 VHH DARIC components or an anti-CLL-1 VHH CAR contemplated herein, etc., to achieve a beneficial or desired prophylactic or therapeutic result in the presence of a bridging factor, including clinical results.

A "prophylactically effective amount" refers to an amount of cells comprising one or more CLL-1 VHH DARIC components or an anti-CLL-1 VHH CAR contemplated herein, etc., effective to achieve the desired prophylactic result in the presence of a bridging factor. Typically but not necessarily, since a prophylactic dose is used in subjects prior to or at an earlier stage of disease, the prophylactically effective amount is less than the therapeutically effective amount.

A "therapeutically effective amount" refers to an amount of cells comprising one or more CLL-1 VHH DARIC components or an anti-CLL-1 VHH CAR contemplated herein that is effective to "treat" a subject (e.g., a patient) in the presence of a bridging factor. When a therapeutic amount is indicated, the precise amount of the compositions to be administered, cells, bridging factor, etc, can be determined by a physician with consideration of individual differences in age, weight, tumor size, extent of infection or metastasis, and condition of the patient (subject).

It can generally be stated that a pharmaceutical composition comprising the immune effector cells described herein may be administered at a dosage of $10^2$ to $10^{10}$ cells/kg body weight, preferably $10^5$ to $10^6$ cells/kg body weight, including all integer values within those ranges. The number of cells will depend upon the ultimate use for which the composition is intended as will the type of cells included therein. For uses provided herein, the cells are generally in a volume of a liter or less, can be 500 mls or less, even 250 mls or 100 mls or less.

Hence the density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. In some embodiments, particularly since all the infused cells will be redirected to a particular target antigen, lower numbers of cells, in the range of $10^6$/kilogram ($10^6$-$10^{11}$ per patient) may be administered.

If desired, the treatment may also include administration of mitogens (e.g., PHA) or lymphokines, cytokines, and/or chemokines (e.g., IFN-γ, IL-2, IL-12, TNF-alpha, IL-18, and TNF-beta, GM-CSF, IL-4, IL-13, Flt3-L, RANTES, MIP1α, etc.) as described herein to enhance induction of the immune response.

Generally, compositions comprising the cells activated and expanded as described herein may be utilized in the treatment and prevention of diseases that arise in individuals who are immunocompromised. In particular, compositions contemplated herein are used in the treatment of cancer. In particular embodiments, the immune effector cells may be administered either alone, or as a pharmaceutical composition in combination with carriers, diluents, excipients, and/or with other components such as IL-2 or other cytokines or cell populations.

In particular embodiments, pharmaceutical compositions comprise an amount of genetically modified T cells, in combination with one or more pharmaceutically or physiologically acceptable carriers, diluents or excipients.

In particular embodiments, pharmaceutical compositions comprise an amount of bridging factor, in combination with one or more pharmaceutically or physiologically acceptable carriers, diluents or excipients.

In a particular embodiment, compositions comprise an effective amount of immune effector cells comprising one or more CLL-1 VHH DARIC components or an anti-CLL-1 VHH CAR contemplated herein, alone or in combination with a bridging factor and/or one or more therapeutic agents, such as radiation therapy, chemotherapy, transplantation, immunotherapy, hormone therapy, photodynamic therapy, etc. The compositions may also be administered in combination with antibiotics. Such therapeutic agents may be accepted in the art as a standard treatment for a particular disease state as described herein, such as a particular cancer. Exemplary therapeutic agents contemplated include cytokines, growth factors, steroids, NSAIDs, DMARDs, anti-inflammatories, chemotherapeutics, radiotherapeutics, therapeutic antibodies, or other active and ancillary agents.

In a particular embodiment, a composition comprising an effective amount of immune effector cells comprising a polynucleotide encoding one or more CLL-1 VHH DARIC components or an anti-CLL-1 VHH CAR contemplated herein is administered to a subject, and a composition comprising an effective amount of a bridging factor is administered to the subject, before, during, in combination with or subsequently to the cellular composition, and optionally repetitively administered to the subject.

In certain embodiments, compositions comprising immune effector cells comprising a polynucleotide encoding one or more CLL-1 VHH DARIC components or an anti-CLL-1 VHH CAR contemplated herein may be administered in conjunction with any number of anti-inflammatory agents, chemotherapeutic agents, or therapeutic antibodies, and the like.

I. Therapeutic Methods

Immune effector cells modified to express a polynucleotide encoding one or more CLL-1 VHH DARIC components or an anti-CLL-1 VHH CAR contemplated herein provide improved methods of adoptive immunotherapy for use in the prevention, treatment, and amelioration of, or for preventing, treating, or ameliorating at least one symptom associated with an immune disorder, e.g., cancer.

Immune effector cells comprising a CLL-1 DARIC signaling component, a CLL-1 VHH DARIC binding component, or an anti-CLL-1 VHH CAR provide improved methods of adoptive immunotherapy for use in the prevention, treatment, and amelioration of, or for preventing, treating, or ameliorating at least one symptom associated with an immune disorder, e.g., cancer.

In particular embodiments, immune effector cells modified to express a CLL-1 VHH DARIC provide improved methods of adoptive immunotherapy to fine-tune the safety and efficacy of a cytotoxic response against target cells, e.g., tumor cells, expressing target antigens while decreasing the risk of on-target antigen, off-target cell cytotoxicity (recognizing the target antigen on a normal, non-target cell).

In particular embodiments, a method of preventing, treating, or ameliorating at least one symptom of a cancer comprises administering the subject an effective amount of modified immune effector cells or T cells comprising one or more components of a CLL-1 VHH DARIC or an anti-CLL-1 VHH CAR to redirect the cells to a target cell. The genetically modified cells are a more efficacious and safe cellular immunotherapy by virtue of transducing a chemically regulatable immunostimulatory signal.

In particular embodiments, one or more immune effector cells, e.g., T cells, are modified to express both a CLL-1 VHH DARIC binding component and a CLL-1 DARIC signaling component. In this case, the modified cells are administered to a subject in need thereof and home to the target cells via the interaction of the CLL-1 VHH binding component expressed on the immune effector cell and CLL-1 expressed on the target cell. A bridging factor is administered to the subject before the modified cells, about the same time as the modified cells, or after the modified cells have been administered to the subject. In the presence of the bridging factor, a ternary complex forms between the CLL-1 VHH DARIC binding component, the bridging factor, and the CLL-1 DARIC signaling component. Upon formation of the ternary complex, the CLL-1 VHH DARIC transduces an immunostimulatory signal to the immune effector cell that in turn, elicits a cytotoxic response from the immune effector cell against the target cell.

In particular embodiments, one or more immune effector cells, e.g., T cells, are modified to express a CLL-1 DARIC signaling component. In this case, the modified cells are administered to a subject in need thereof. A CLL-1 VHH DARIC binding component can be administered to the subject before the modified cells, about the same time as the modified cells, or after the modified cells have been administered to the subject. In addition, the CLL-1 VHH DARIC binding component can be administered to the subject in a preformed complex with the bridging factor; at the same time as the bridging factor, but in a separate composition; or at a different time than the bridging factor. The CLL-1 VHH binding component binds CLL-1 expressed on the target cell, either in the presence or absence of the bridging factor. In the presence of the bridging factor, a ternary complex forms between the CLL-1 VHH DARIC binding component, the bridging factor, and the CLL-1 DARIC signaling component. Upon formation of the ternary complex, the CLL-1 VHH DARIC transduces an immunostimulatory signal to the immune effector cell that in turn, elicits a cytotoxic response from the immune effector cell against the target cell.

In particular embodiments, one or more immune effector cells, e.g., T cells, are modified to express the CLL-1 DARIC signaling component. In this case, the modified cells are administered to a subject in need thereof. A CLL-1 VHH DARIC binding component can be administered to the subject before the modified cells, about the same time as the modified cells, or after the modified cells have been administered to the subject. In addition, the CLL-1 VHH DARIC binding component can be administered to the subject in a preformed complex with the bridging factor; at the same time as the bridging factor, but in a separate composition; or at a different time than the bridging factor. The CLL-1 binding component binds the target antigen expressed on the target cell, either in the presence or absence of the bridging factor. In the presence of the bridging factor, a ternary complex forms between the CLL-1 VHH DARIC binding component, the bridging factor, and the CLL-1 DARIC signaling component. Upon formation of the ternary complex, the CLL-1 VHH DARIC transduces an immunostimulatory signal to the immune effector cell that in turn, elicits a cytotoxic response from the immune effector cell against the target cell. In particular embodiments, CLL-1 VHH DARIC activation can be induced in cases where remission or regression is incomplete and the condition relapses or becomes refractory to treatment.

In particular preferred embodiments, the specificity of a primary T cell is redirected to tumor or cancer cells that express CLL-1 by genetically modifying a T cell, e.g., a primary T cell, with one or more CLL-1 VHH DARIC components.

In particular preferred embodiments, the specificity of a primary T cell is redirected to tumor or cancer cells that express CLL-1 by genetically modifying a T cell, e.g., a primary T cell, with an engineered antigen receptor directed to the target antigen and one or more CLL-1 VHH DARIC components.

In particular embodiments, the modified immune effector cells contemplated herein are used in the treatment of solid tumors or cancers.

In particular embodiments, the modified immune effector cells contemplated herein are used in the treatment of solid tumors or cancers including, but not limited to: adrenal cancer, adrenocortical carcinoma, anal cancer, appendix cancer, astrocytoma, atypical teratoid/rhabdoid tumor, basal cell carcinoma, bile duct cancer, bladder cancer, bone cancer, brain/CNS cancer, breast cancer, bronchial tumors, cardiac tumors, cervical cancer, cholangiocarcinoma, chondrosarcoma, chordoma, colon cancer, colorectal cancer, craniopharyngioma, ductal carcinoma in situ (DCIS) endometrial cancer, ependymoma, esophageal cancer, esthesioneuroblastoma, Ewing's sarcoma, extracranial germ cell tumor, extragonadal germ cell tumor, eye cancer, fallopian tube cancer, fibrous histiosarcoma, fibrosarcoma, gallbladder cancer, gastric cancer, gastrointestinal carcinoid tumors, gastrointestinal stromal tumor (GIST), germ cell tumors, glioma, glioblastoma, head and neck cancer, hemangioblastoma, hepatocellular cancer, hypopharyngeal cancer, intraocular melanoma, kaposi sarcoma, kidney cancer, laryngeal cancer, leiomyosarcoma, lip cancer, liposarcoma, liver cancer, lung cancer, non-small cell lung cancer, lung carcinoid tumor, malignant mesothelioma, medullary carcinoma, medulloblastoma, menangioma, melanoma, Merkel cell carcinoma, midline tract carcinoma, mouth cancer, myxosarcoma, myelodysplastic syndrome, myeloproliferative neoplasms, nasal cavity and paranasal sinus cancer, nasopharyngeal cancer, neuroblastoma, oligodendroglioma, oral cancer, oral cavity cancer, oropharyngeal cancer, osteosarcoma, ovarian cancer, pancreatic cancer, pancreatic islet cell tumors, papillary carcinoma, paraganglioma, parathyroid cancer, penile cancer, pharyngeal cancer, pheochromocytoma, pinealoma, pituitary tumor, pleuropulmonary blastoma, primary peritoneal cancer, prostate cancer, rectal cancer, retinoblastoma, renal cell carcinoma, renal pelvis and ureter cancer, rhabdomyosarcoma, salivary gland cancer, sebaceous gland carcinoma, skin cancer, soft tissue sarcoma, squamous cell carcinoma, small cell lung cancer, small intestine cancer, stomach cancer, sweat gland carcinoma, synovioma, testicular cancer, throat cancer, thymus cancer, thyroid cancer, urethral cancer, uterine cancer, uterine sarcoma, vaginal cancer, vascular cancer, vulvar cancer, and Wilms Tumor.

In particular embodiments, the modified immune effector cells contemplated herein are used in the treatment of solid tumors or cancers including, without limitation, non-small cell lung carcinoma, head and neck squamous cell carcinoma, colorectal cancer, pancreatic cancer, breast cancer, thyroid cancer, bladder cancer, cervical cancer, esophageal cancer, ovarian cancer, gastric cancer endometrial cancer, gliomas, glioblastomas, and oligodendroglioma.

In particular embodiments, the modified immune effector cells contemplated herein are used in the treatment of solid tumors or cancers including, without limitation, non-small-cell lung cancer, metastatic colorectal cancer, glioblastoma, head and neck cancer, pancreatic cancer, and breast cancer.

In particular embodiments, the modified immune effector cells contemplated herein are used in the treatment of glioblastoma.

In particular embodiments, the modified immune effector cells contemplated herein are used in the treatment of liquid cancers or hematological cancers.

In particular embodiments, the modified immune effector cells contemplated herein are used in the treatment of B-cell malignancies, including but not limited to: leukemias, lymphomas, and multiple myeloma.

In particular embodiments, the modified immune effector cells contemplated herein are used in the treatment of liquid cancers including, but not limited to leukemias, lymphomas, and multiple myelomas: acute lymphocytic leukemia (ALL), acute myeloid leukemia (AMIL), myeloblastic, promyelocytic, myelomonocytic, monocytic, erythroleukemia, hairy cell leukemia (HCL), chronic lymphocytic leukemia (CLL), and chronic myeloid leukemia (CML), chronic myelomonocytic leukemia (CMML) and polycythemia vera, Hodgkin lymphoma, nodular lymphocyte-predominant Hodgkin lymphoma, Burkitt lymphoma, small lymphocytic lymphoma (SLL), diffuse large B-cell lymphoma, follicular lymphoma, immunoblastic large cell lymphoma, precursor B-lymphoblastic lymphoma, mantle cell lymphoma, marginal zone lymphoma, mycosis fungoides, anaplastic large cell lymphoma, Sézary syndrome, precursor T-lymphoblastic lymphoma, multiple myeloma, overt multiple myeloma, smoldering multiple myeloma, plasma cell leukemia, non-secretory myeloma, IgD myeloma, osteosclerotic myeloma, solitary plasmacytoma of bone, and extramedullary plasmacytoma.

In particular embodiments, the modified immune effector cells contemplated herein are used in the treatment of acute myeloid leukemia (AML).

Preferred cells for use in the methods contemplated herein include autologous/autogeneic ("self") cells, preferably hematopoietic cells, more preferably T cells, and more preferably immune effector cells.

In particular embodiments, a method comprises administering a therapeutically effective amount of modified immune effector cells that express one or more CLL-1 VHH DARIC components, to a patient in need thereof, and also administering abridging factor to the subject. In certain embodiments, the cells are used in the treatment of patients at risk for developing an immune disorder. Thus, particular embodiments comprise the treatment or prevention or amelioration of at least one symptom of an immune disorder, e.g., cancer, comprising administering to a subject in need thereof, a therapeutically effective amount of the modified immune effector cells contemplated herein and a bridging factor.

In particular embodiments, a method comprises administering a therapeutically effective amount of modified immune effector cells that express an anti-CLL-1 VHH CAR to a patient in need thereof. In certain embodiments, the cells are used in the treatment of patients at risk for developing an immune disorder. Thus, particular embodiments comprise the treatment or prevention or amelioration of at least one symptom of an immune disorder, e.g., cancer, comprising administering to a subject in need thereof, a therapeutically effective amount of the modified immune effector cells contemplated herein and a bridging factor.

In particular embodiments, a method comprises administering a therapeutically effective amount of modified immune effector cells that express a CLL-1 DARIC signaling component or a composition comprising the same, to a patient in need thereof, and also administering a CLL-1 VHH DARIC binding component and a bridging factor, optionally wherein the CLL-1 VHH DARIC binding component is bound to the bridging factor prior to administration, to the subject. In certain embodiments, the cells are used in the treatment of patients at risk for developing an immune disorder. Thus, particular embodiments comprise the treatment or prevention or amelioration of at least one symptom of an immune disorder, e.g., cancer, comprising administering to a subject in need thereof, a therapeutically effective amount of the modified immune effector cells that express a CLL-1 DARIC signaling component and optionally and engineered antigen receptor or another DARIC binding component, a CLL-1 VHH DARIC binding component, and a bridging factor.

The quantity and frequency of administration of modified immune effector cells, CLL-1 DARIC VHH binding components, and/or bridging factor will be determined by such factors as the condition of the patient, and the type and severity of the patient's disease, although appropriate dosages and dose schedules may be determined by clinical trials.

In one illustrative embodiment, the effective amount of modified immune effector cells provided to a subject is at least $2 \times 10^6$ cells/kg, at least $3 \times 10^6$ cells/kg, at least $4 \times 10^6$ cells/kg, at least $5 \times 10^6$ cells/kg, at least $6 \times 10^6$ cells/kg, at least $7 \times 10^6$ cells/kg, at least $8 \times 10^6$ cells/kg, at least $9 \times 10^6$ cells/kg, or at least $10 \times 10^6$ cells/kg, or more cells/kg, including all intervening doses of cells.

In another illustrative embodiment, the effective amount of modified immune effector cells provided to a subject is about $2 \times 10^6$ cells/kg, about $3 \times 10^6$ cells/kg, about $4 \times 10^6$ cells/kg, about $5 \times 10^6$ cells/kg, about $6 \times 10^6$ cells/kg, about $7 \times 10^6$ cells/kg, about $8 \times 10^6$ cells/kg, about $9 \times 10^6$ cells/kg, or about $10 \times 10^6$ cells/kg, or more cells/kg, including all intervening doses of cells.

In another illustrative embodiment, the effective amount of modified immune effector cells provided to a subject is from about $2 \times 10^6$ cells/kg to about $10 \times 10^6$ cells/kg, about $3 \times 10^6$ cells/kg to about $10 \times 10^6$ cells/kg, about $4 \times 10^6$ cells/kg to about $10 \times 10^6$ cells/kg, about $5 \times 10^6$ cells/kg to about $10 \times 10^6$ cells/kg, $2 \times 10^6$ cells/kg to about $6 \times 10^6$ cells/kg, $2 \times 10^6$ cells/kg to about $7 \times 10^6$ cells/kg, $2 \times 10^6$ cells/kg to about $8 \times 10^6$ cells/kg, $3 \times 10^6$ cells/kg to about $6 \times 10^6$ cells/kg, $3 \times 10^6$ cells/kg to about $7 \times 10^6$ cells/kg, $3 \times 10^6$ cells/kg to about $8 \times 10^6$ cells/kg, $4 \times 10^6$ cells/kg to about $6 \times 10^6$ cells/kg, $4 \times 10^6$ cells/kg to about $7 \times 10^6$ cells/kg, $4 \times 10^6$ cells/kg to about 8×10⁶ cells/kg, 5×10⁶ cells/kg to about 6×10⁶ cells/kg, 5×10⁶ cells/kg to about 7×10⁶ cells/kg, 5×10⁶ cells/kg to about 8×10⁶ cells/kg, or 6×10⁶ cells/kg to about 8×10⁶ cells/kg, including all intervening doses of cells.

One of ordinary skill in the art would recognize that multiple administrations of the compositions contemplated in particular embodiments may be required to effect the desired therapy. For example, a composition may be administered 1, 2, 3, 4, 5, 6, 7, 8, 9, or 10 or more times over a span of 1 week, 2 weeks, 3 weeks, 1 month, 2 months, 3 months, 4 months, 5 months, 6 months, 1 year, 2 years, 5, years, 10 years, or more. Modified immune effector cells, CLL-1 VHH DARIC components, and bridging factor may be administered in the same or different compositions; in one or more compositions at the same time; or more than one composition at different times. Modified immune effector cells, CLL-1 VHH DARIC components, and bridging factor may be administered through the same route of administration or different routes.

In certain embodiments, it may be desirable to administer activated T cells to a subject and then subsequently redraw blood (or have an apheresis performed), activate T cells therefrom, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, 100 cc, 150 cc, 200 cc, 250 cc, 300 cc, 350 cc, or 400 cc or more. Not to be bound by theory, using this multiple blood draw/multiple reinfusion protocol may serve to select out certain populations of T cells.

In one embodiment, a method of treating a subject diagnosed with a cancer, comprises removing immune effector cells from the subject, modifying the immune effector cells by introducing one or more vectors encoding one or more CLL-1 VHH DARIC components into the cell and producing a population of modified immune effector cells, and administering the population of modified immune effector cells to the same subject. In a preferred embodiment, the immune effector cells comprise T cells.

In one embodiment, a method of treating a subject diagnosed with a cancer, comprises removing immune effector cells from the subject, modifying the immune effector cells by introducing one or more vectors encoding an anti-CLL-1 VHH CAR into the cell and producing a population of modified immune effector cells, and administering the population of modified immune effector cells to the same subject. In a preferred embodiment, the immune effector cells comprise T cells.

The methods for administering the cell compositions contemplated in particular embodiments include any method which is effective to result in reintroduction of ex vivo modified immune effector cells or reintroduction of modified progenitors of immune effector cells that upon introduction into a subject differentiate into mature immune effector cells. One method comprises modifying peripheral blood T cells ex vivo by introducing one or more vectors encoding one or more CLL-1 VHH DARIC components or an anti-CLL-1 VHH CAR into the cell and returning the transduced cells into the subject.

All publications, patent applications, and issued patents cited in this specification are herein incorporated by reference as if each individual publication, patent application, or issued patent were specifically and individually indicated to be incorporated by reference.

Although the foregoing embodiments have been described in some detail by way of illustration and example for purposes of clarity of understanding, it will be readily apparent to one of ordinary skill in the art in light of the teachings contemplated herein that certain changes and modifications may be made thereto without departing from the spirit or scope of the appended claims. The following examples are provided by way of illustration only and not by way of limitation. Those of skill in the art will readily recognize a variety of noncritical parameters that could be changed or modified in particular embodiments to yield essentially similar results.

EXAMPLES

Example 1

CLL-1 VHH Daric T Cells Exhibit Anti-Tumor Responses

Anti-CLL-1 VHH DARIC binding and signaling components were designed, constructed, and verified. CLL-1 specific VHH DARIC lentiviral vectors were constructed comprising an MNDU3 promoter operably linked to a polynucleotide encoding: a DARIC signaling component (CD8α-signal peptide, an FRB variant (T82L), a CD8α transmembrane domain, an intracellular 4-1BB costimulatory domain, and a CD3 zeta signaling domain); a P2A sequence; and a DARIC binding component (an Igx-signal peptide, a CLL-1 specific VHH binding domain, a G4S linker, an FKBP12 domain, and a CD4 derived transmembrane domain with a truncated intracellular domain (FIG. 1B). See, e.g., SEQ ID NOs: 20-25. T cells transduced with anti-CLL-1 DARIC lentiviral vectors express the membrane bound polypeptides shown in FIG. 1A. An anti-CLL-1 scFv CAR was used as a control.

Figure 2:
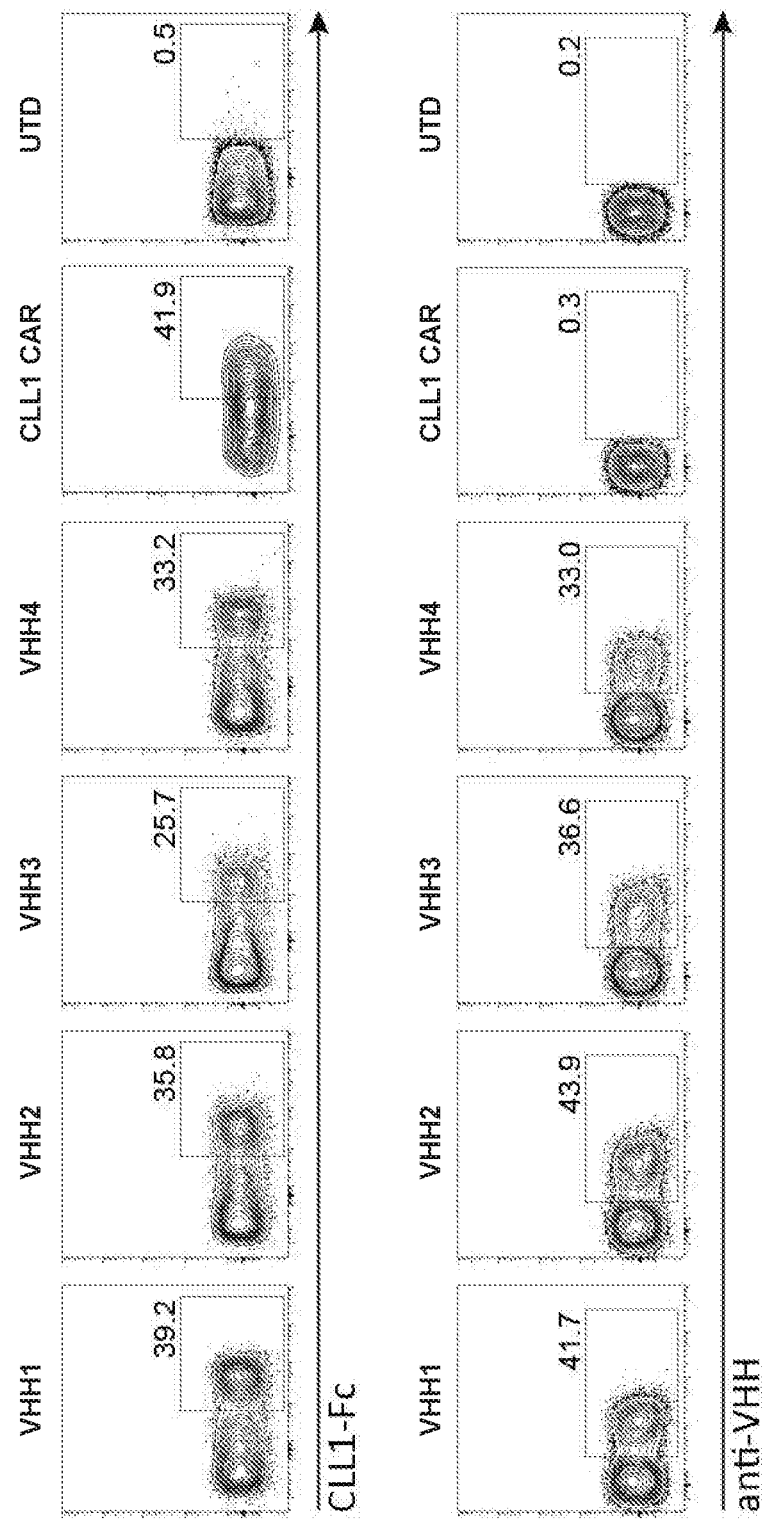
FIG. 2 shows the expression of CLL-1 VHH DARIC in transduced T cells, as detected by CLL-1-Fc binding (top row) and by anti-VHH staining (bottom row).
Figure 3:
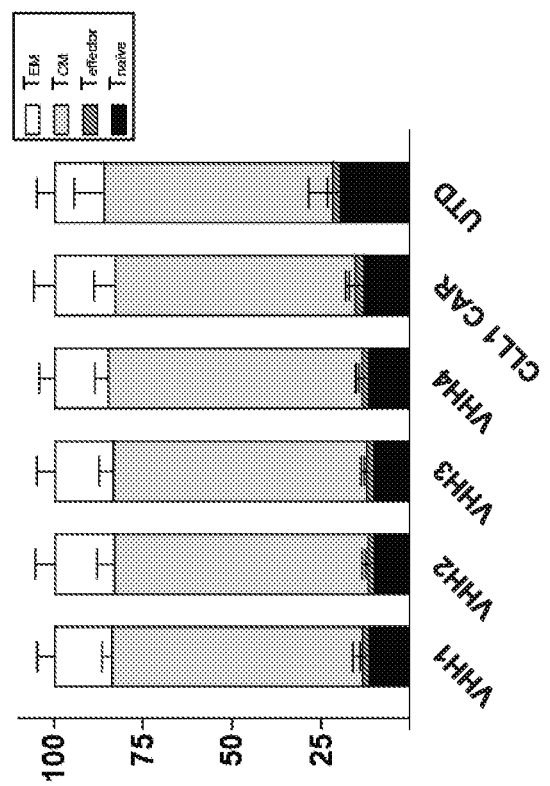
FIG. 3 shows the phenotype of T cells transduced with CLL-1 VHH DARIC or controls.

T cells from three donors were each transduced with one of four LVVs encoding different CLL-1 specific VHH DARICs or an anti-CLL-1 scFv CAR and expanded for 10 days. Untransduced T cells, T cells transduced with an anti-CLL-1 scFv CAR, or anti-CLL-1 VHH DARIC T cells were stained with recombinant CLL-1-Fc reagent. Control CAR and CLL-1 VHH DARIC T cells were positively stained with the CLL-1-Fc staining (FIG. 2, top panel). However, only the anti-CLL-1 VHH DARIC T cells, but not control CAR T cells, stained positively when analyzed with a monoclonal antibody specific for the VHH domain (FIG. 2, bottom panel). Both control CAR T cells and anti-CLL-1 VHH DARIC T cells had a similar T cell phenotype, as determined, in part, by CD62L and CD45RA staining (FIG. 3).

Figure 4:
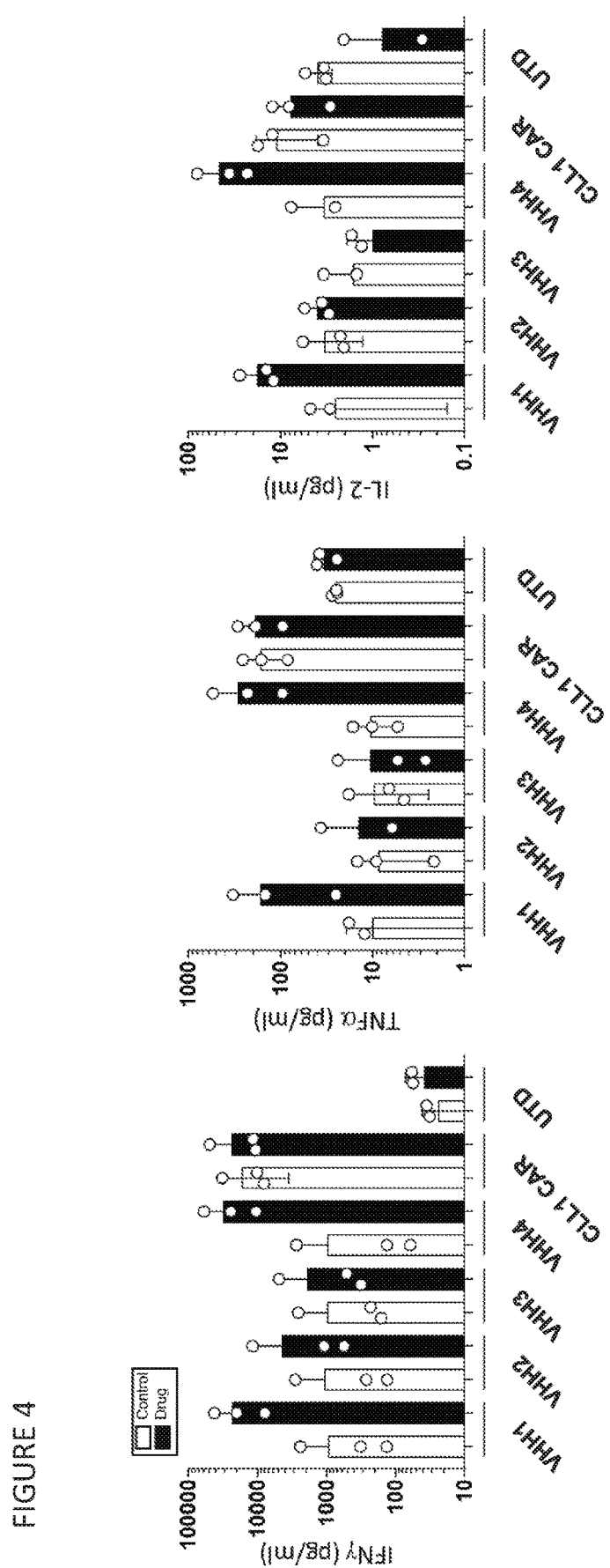
FIG. 4 shows cytokine (IFNγ, TNFα, and IL-2) secretion from CLL-1 VHH DARIC or control cells cultured with CLL-1+ THP-1 cells at an E:T ratio of 1:1 in the presence or absence of AP21967 for 24 hours.

Untransduced T cells, T cells transduced with an anti-CLL-1 scFv CAR, or anti-CLL-1 VHH DARIC T cells were co-cultured with CLL-1⁺ THP-1 cells at an E:T ratio of 1:1 in the presence or absence of AP21967 for 24 hours. Anti-CLL-1 scFv CAR control cells had strong cytokine production both in the presence or absence of rapalog. Anti-CLL-VHH DARIC T cells exhibited a robust cytokine response only when cultured with THP-1 cell in the presence of AP21967 (FIG. 4). Minimal cytokine production was detected in untransduced controls.

Example 2

CLL-1 VHH Daric T Cells Specifically Respond to Aml Cell Lines

Figure 5:
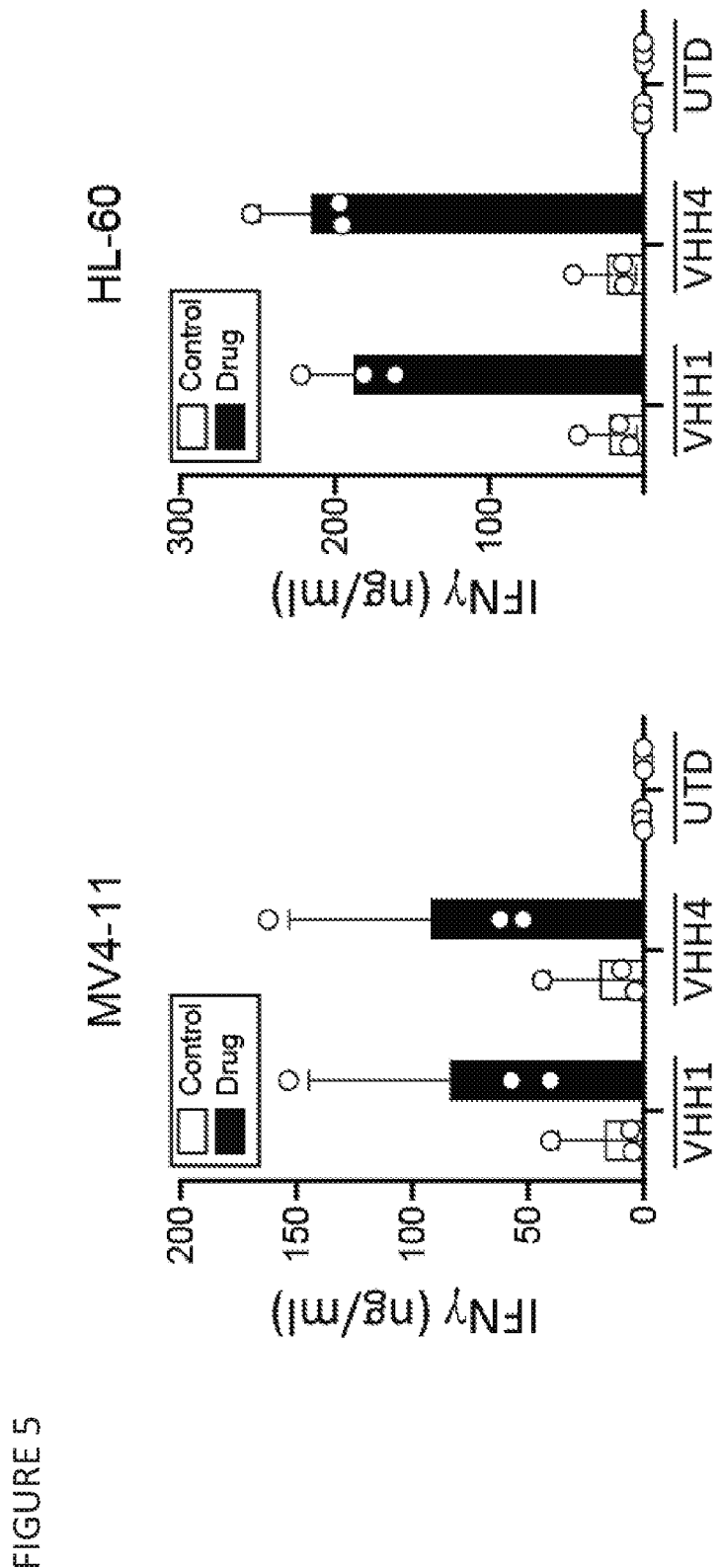
FIG. 5 shows IFNγ secretion from UTD T cells or CLL-1 VHH DARIC T cells co-cultured with CLL-1 expressing MV4-11 or HL60 AML cell lines at an E:T ratio of 1:1 in the presence or absence of AP21967 for 24 hours.

Anti-CLL-1 VHH DARIC T cells were generated as described in Example 1. T cells from three donors were transduced with LVVs encoding different anti-CLL-1 VHH DARICs and expanded for 10 days. Controls included untransduced (UTD) T cells. Anti-CLL-1 VHH DARIC T cells were co-cultured with CLL-1 expressing MV4-11 or HL60 AML cell lines at an E:T ratio of 1:1 in the presence or absence of AP21967 for 24 hours. in response to MV4-11 or HL60 target cells in the presence of AP21967. FIG. 5.

Example 3

CLL-1 VHH Daric T Cells Specifically Recognize Cll-1 Antigen

Anti-CLL-1 VHH DARIC T cells were generated as described in Example 1. T cells from three donors were transduced with LVVs encoding different anti-CLL-1 VHH DARICs and expanded for 10 days. Controls included UTD T cells. The AML cell line THP-1 was modified to knock-out CLL-1 expression (CLL-1-KO cells). FIG. 6A. Anti-CLL-1 VHH DARIC T cells were co-cultured with THP-1 cells or CLL-1-KO cells at an E:T ratio of 1:1 in the presence or absence of AP21967 for 24 hours. Anti-CLL-1 VHH DARIC T cells produced cytokine when co-cultured with THP-1 cells in the presence of AP21967 (FIG. 6B-C).

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A non-natural cell comprising:
   (a) a first polypeptide comprising: an FRB multimerization domain polypeptide or variant thereof; a CD8α transmembrane domain or a CD4 transmembrane domain; a CD137 co-stimulatory domain; and/or a CD3Q primary signaling domain; and
   (b) a second polypeptide comprising: an anti-CLL-1 VHH antibody that has an amino acid sequence set forth in any one of SEQ ID NOs: 8, 2-7, and 9-13; an FKBP multimerization domain polypeptide or variant thereof; and a CD4 transmembrane domain or a CD8α transmembrane domain;
   wherein a bridging factor promotes the formation of a polypeptide complex on the non-natural cell surface with the bridging factor associated with and disposed between the multimerization domains of the first and second polypeptides.

2. The non-natural cell of claim 1, wherein the FKBP multimerization domain is FKBP12 and/or wherein the FRB polypeptide is FRB T2098L.

3. The non-natural cell of claim 1, wherein the FRB multimerization domain and the FKBP multimerization domain localize extracellularly when the first polypeptide and the second polypeptide are expressed.

4. The non-natural cell of claim 1, wherein the bridging factor is selected from the group consisting of: AP21967, sirolimus, everolimus, novolimus, pimecrolimus, ridaforolimus, tacrolimus, temsirolimus, umirolimus, and zotarolimus.

5. The non-natural cell of claim 1, wherein the first polypeptide comprises a signal peptide, a CD8α transmembrane domain; a CD137 co-stimulatory domain; and a CD3ζ primary signaling domain.

6. The non-natural cell of claim 1, wherein the second polypeptide comprises a signal peptide, a CD4 transmembrane domain and/or a costimulatory domain.

7. The non-natural cell of claim 6, wherein the costimulatory domain of the second polypeptide is a costimulatory domain isolated from OX40 or TNFR2.

8. The non-natural cell of claim 1, wherein the second polypeptide comprises the sequence set forth in any one of SEQ ID NOs: 14-19.

9. A polynucleotide encoding the first and second polypeptides of claim 1.

10. A vector comprising the polynucleotide of claim 9.

11. The vector of claim 10, wherein the vector is a lentiviral vector.

12. The non-natural cell of claim 1, wherein the cell is:
   a) a hematopoietic cell
   b) a T cell, an αβ T cell, or a γδ T cell;
   c) a CD3+, CD4+, and/or CD8+ cell;
   d) an immune effector cell;
   e) a cytotoxic T lymphocyte (CTL), a tumor infiltrating lymphocyte (TIL), or a helper T cell; or
   f) a natural killer (NK) cell or natural killer T (NKT) cell.

13. A composition comprising a cell according to claim 12.

14. A method of treating a subject having acute myelogenous leukemia (AML), comprising administering to the subject an effective amount of the composition of claim 13.

15. A fusion polypeptide comprising:
   (a) a first polypeptide comprising: an FRB multimerization domain polypeptide or variant thereof; a CD8α transmembrane domain or a CD4 transmembrane domain; a CD137 co-stimulatory domain; and/or a CD3ζ primary signaling domain;
   (b) a polypeptide cleavage signal; and
   (c) a second polypeptide comprising: an anti-CLL-1 VHH antibody that has an amino acid sequence set forth in any one of SEQ ID NOs: 2-13; an FKBP multimerization domain polypeptide or variant thereof; and a CD4 transmembrane domain or a CD8α transmembrane domain.

16. The non-natural cell of claim 15, wherein the fusion polypeptide comprises the sequence set forth in any one of SEQ ID NOs: 20-25.

17. The non-natural cell of claim 15, wherein the fusion polypeptide comprises the sequence set forth in any one of SEQ ID NOs: 26-37.

18. A polynucleotide encoding the fusion polypeptide of claim 15.

19. A vector comprising the polynucleotide of claim 18.

20. The vector of claim 19, wherein the vector is a lentiviral vector.

* * * * *